US009757458B2

United States Patent
Chang et al.

(10) Patent No.: US 9,757,458 B2
(45) Date of Patent: Sep. 12, 2017

(54) CROSSLINKING OF CD22 BY EPRATUZUMAB TRIGGERS BCR SIGNALING AND CASPASE-DEPENDENT APOPTOSIS IN HEMATOPOIETIC CANCER CELLS

(71) Applicant: Immunomedics, Inc., Morris Plains, NJ (US)

(72) Inventors: Chien-Hsing Chang, Downingtown, PA (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 14/861,636

(22) Filed: Sep. 22, 2015

(65) Prior Publication Data

US 2016/0000915 A1 Jan. 7, 2016

Related U.S. Application Data

(63) Continuation-in-part of application No. 14/243,512, filed on Apr. 2, 2014, which is a continuation-in-part of application No. 13/693,476, filed on Dec. 4, 2012, now Pat. No. 9,192,664.

(60) Provisional application No. 61/566,828, filed on Dec. 5, 2011, provisional application No. 61/609,075, filed on Mar. 9, 2012, provisional application No. 61/682,508, filed on Aug. 13, 2012, provisional application No. 61/718,226, filed on Oct. 25, 2012, provisional application No. 61/808,005, filed on Apr. 3, 2013, provisional application No. 61/832,558, filed on Jun. 7, 2013, provisional application No. 61/941,100, filed on Feb. 18, 2014, provisional application No. 62/054,581, filed on Sep. 24, 2014.

(51) Int. Cl.

| A61K 39/395 | (2006.01) |
|---|---|
| A61K 45/06 | (2006.01) |
| C07K 14/56 | (2006.01) |
| C07K 16/28 | (2006.01) |
| C07K 16/30 | (2006.01) |
| C07K 16/46 | (2006.01) |
| A61K 39/00 | (2006.01) |

(52) U.S. Cl.
CPC ............. *A61K 45/06* (2013.01); *C07K 14/56* (2013.01); *C07K 16/2803* (2013.01); *C07K 16/2833* (2013.01); *C07K 16/2887* (2013.01); *C07K 16/3007* (2013.01); *C07K 16/468* (2013.01); *A61K 2039/505* (2013.01); *C07K 2317/24* (2013.01); *C07K 2317/31* (2013.01); *C07K 2317/54* (2013.01); *C07K 2317/55* (2013.01); *C07K 2317/73* (2013.01); *C07K 2317/732* (2013.01); *C07K 2317/734* (2013.01); *C07K 2317/77* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| 4,036,945 A | 7/1977 | Haber |
|---|---|---|
| 4,046,722 A | 9/1977 | Rowland |
| 4,331,647 A | 5/1982 | Goldenberg |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Hawthorne |
| 4,916,213 A | 4/1990 | Scannon et al. |
| 4,918,163 A | 4/1990 | Young |

(Continued)

FOREIGN PATENT DOCUMENTS

| EP | 0332865 | 9/1989 |
|---|---|---|
| EP | 0510949 | 10/1992 |

(Continued)

OTHER PUBLICATIONS

US 6,558,648, 05/2003, Griffiths et al. (withdrawn)
Leonard et al., Oncogene. May 28, 2007;26(25):3704-13.*
Watanabe et al., "The duration of signaling through CD40 directs biological ability of dendritic cells to induce antitumor immunity", J Immunol. Dec. 1, 2003;171(11):5828-36.

(Continued)

*Primary Examiner* — Michael Szperka
(74) *Attorney, Agent, or Firm* — Richard A. Nakashima

(57) ABSTRACT

Extensive crosslinking of CD22 by plate-immobilized epratuzumab induced intracellular changes in Daudi cells similar to ligating B-cell antigen receptor (BCR) with a sufficiently high amount of anti-IgM. Either treatment leads to phosphorylation of CD22, CD79a and CD79b, along with their translocation to lipid rafts, both of which were needed to induce caspase-dependent apoptosis. Immobilization also induced stabilization of F-actin, phosphorylation of Lyn, ERKs and JNKs, generation of reactive oxygen species (ROS), decrease in mitochondria membrane potential ($\Delta\psi_m$), upregulation of pro-apoptotic Bax, and downregulation of anti-apoptotic Bcl-xl and Mcl-1. Several of the in vitro effects of immobilized epratuzumab, including apoptosis, drop in $\Delta\psi_m$, and generation of ROS, were observed with soluble epratuzumab in Daudi cells co-cultivated with human umbilical vein endothelial cells. The in vivo mechanism of non-ligand-blocking epratuzumab may, in part, involve the unmasking of CD22 to facilitate the trans-interaction of B cells with vascular endothelium.

33 Claims, 26 Drawing Sheets

(56) References Cited

U.S. PATENT DOCUMENTS

| | | | |
|---|---|---|---|
| 4,925,922 A | 5/1990 | Byers et al. | |
| 4,932,412 A | 6/1990 | Goldenberg | |
| 4,946,778 A | 8/1990 | Ladner et al. | |
| 5,057,313 A | 10/1991 | Shih et al. | |
| 5,106,955 A | 4/1992 | Endo et al. | |
| 5,134,075 A | 7/1992 | Hellstrom et al. | |
| 5,171,665 A | 12/1992 | Hellstrom et al. | |
| 5,196,337 A | 3/1993 | Ochi et al. | |
| 5,204,095 A | 4/1993 | Goodall et al. | |
| 5,229,275 A | 7/1993 | Goroff | |
| 5,443,953 A | 8/1995 | Hansen et al. | |
| 5,484,892 A | 1/1996 | Tedder et al. | |
| 5,525,338 A | 6/1996 | Goldenberg | |
| 5,565,215 A | 10/1996 | Gref et al. | |
| 5,567,610 A | 10/1996 | Borrebaeck et al. | |
| 5,593,676 A | 1/1997 | Bhat et al. | |
| 5,618,920 A | 4/1997 | Robinson et al. | |
| 5,620,708 A | 4/1997 | Amkraut et al. | |
| 5,633,425 A | 5/1997 | Lonberg et al. | |
| 5,679,640 A | 10/1997 | Gaeta et al. | |
| 5,686,072 A | 11/1997 | Uhr et al. | |
| 5,693,762 A | 12/1997 | Queen et al. | |
| 5,698,178 A | 12/1997 | Goldenberg | |
| 5,702,727 A | 12/1997 | Amkraut et al. | |
| 5,716,595 A | 2/1998 | Goldenberg | |
| 5,736,119 A | 4/1998 | Goldenberg et al. | |
| 5,750,105 A | 5/1998 | Newman et al. | |
| 5,776,456 A | 7/1998 | Anderson et al. | |
| 5,789,554 A | 8/1998 | Leung et al. | |
| 5,792,845 A | 8/1998 | O'Reilly et al. | |
| 5,795,967 A | 8/1998 | Aggarwal et al. | |
| 5,798,554 A | 8/1998 | Grimaldi et al. | |
| 5,874,540 A | 2/1999 | Hansen et al. | |
| 5,922,302 A | 7/1999 | Goldenberg et al. | |
| 6,051,228 A | 4/2000 | Aruffo et al. | |
| 6,051,230 A | 4/2000 | Thorpe et al. | |
| 6,077,499 A | 6/2000 | Griffiths et al. | |
| 6,096,289 A | 8/2000 | Goldenberg | |
| 6,165,440 A | 12/2000 | Esenaliev | |
| 6,183,744 B1* | 2/2001 | Goldenberg | A61K 39/39558 424/130.1 |
| 6,187,287 B1 | 2/2001 | Leung et al. | |
| 6,254,868 B1 | 7/2001 | Leung et al. | |
| 6,306,393 B1 | 10/2001 | Goldenberg | |
| 6,331,175 B1 | 12/2001 | Goldenberg | |
| 6,379,698 B1 | 4/2002 | Leamon | |
| 6,387,350 B2 | 5/2002 | Goldenberg | |
| 6,395,276 B1 | 5/2002 | Rybak et al. | |
| 6,530,944 B2 | 3/2003 | West et al. | |
| 6,562,318 B1 | 5/2003 | Filler | |
| 6,653,104 B2 | 11/2003 | Goldenberg | |
| 7,018,809 B1 | 3/2006 | Carter | |
| 7,074,403 B1 | 7/2006 | Goldenberg et al. | |
| 7,387,779 B2 | 6/2008 | Kalluri | |
| 7,641,901 B2 | 1/2010 | Goldenberg et al. | |
| 7,772,373 B2 | 8/2010 | Hansen et al. | |
| 7,820,161 B1 | 10/2010 | Curd et al. | |
| 7,837,995 B2* | 11/2010 | Goldenberg | A61K 39/395 424/130.1 |
| 7,910,103 B2 | 3/2011 | Goldenberg | |
| 7,931,903 B2 | 4/2011 | Hansen et al. | |
| 7,939,073 B2* | 5/2011 | Goldenberg | A61K 39/395 424/130.1 |
| 8,158,573 B2 | 4/2012 | McBride et al. | |
| 8,202,509 B2 | 6/2012 | McBride et al. | |
| 8,287,864 B2 | 10/2012 | Goldenberg et al. | |
| 8,349,332 B2 | 1/2013 | Chang et al. | |
| 8,420,086 B2* | 4/2013 | Govindan | A61K 47/48384 424/133.1 |
| 8,425,912 B2 | 4/2013 | Govindan et al. | |
| 8,444,956 B2 | 5/2013 | McBride et al. | |
| 8,481,003 B2 | 7/2013 | Griffiths et al. | |
| 8,591,892 B2 | 11/2013 | Alinari et al. | |
| 8,709,382 B2 | 4/2014 | D'Souza et al. | |
| 8,741,300 B2 | 6/2014 | Govindan et al. | |
| 8,871,216 B2 | 10/2014 | Chang et al. | |
| 8,906,378 B2 | 12/2014 | Chang et al. | |
| 2002/0018749 A1 | 2/2002 | Hudson et al. | |
| 2004/0076683 A1 | 4/2004 | Hoarau et al. | |
| 2005/0079184 A1 | 4/2005 | Chang et al. | |
| 2007/0140966 A1 | 6/2007 | Chang et al. | |
| 2009/0270268 A1* | 10/2009 | Funaro | A61K 45/06 506/9 |
| 2010/0330089 A1 | 12/2010 | Damle et al. | |
| 2011/0020344 A1* | 1/2011 | Dimitrov | C07K 16/2803 424/134.1 |
| 2011/0070227 A1* | 3/2011 | Novotney-Barry | C07K 16/2803 424/133.1 |
| 2011/0256053 A1 | 10/2011 | Chang et al. | |

FOREIGN PATENT DOCUMENTS

| | | |
|---|---|---|
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 00/74718 | 12/2000 |

OTHER PUBLICATIONS

Yu et al., "Synthetic glycan ligand excludes CD22 from antigen receptor-containing lipid rafts", Biochem Biophys Res Commun. Sep. 7, 2007;360(4):759-64.

Ponticelli et al., "Monoclonal Antibodies for Systemic Lupus Erythematosus (SLE)", Pharmaceuticals 2010, 3(1), 300-322.

Rossi et al., "Trogocytosis of multiple B-cell surface markers by CD22 targeting with epratuzumab", Blood. Oct. 24, 2013;122(17):3020-9.

Rossi et al., "Anti-CD22/CD20 Bispecific antibody with enhanced trogocytosis for treatment of Lupus", PLoS One. May 19, 2014;9(5):e98315.

Rossi et al., "Optimization of multivalent bispecific antibodies and immunocytokines with improved in vivo properties", Bioconjug Chem. Jan. 16, 2013;24(1):63-71.

Taylor, R., "Gnawing at Metchnikoff's paradigm", Blood. Oct. 24, 2013;122(17):2922-4.

Tieng et al., "B-cell-directed therapies in systemic lupus erythematosus", Semin Arthritis Rheum. Dec. 2008;38 (3):218-27.

Levine et al., "IgM antibody-related polyneuropathies: B-cell depletion chemotherapy using Rituximab", Neurology 52 (8):1701-4 (1999).

Li et al., "The epitope specificity and tissue reactivity of four murine monoclonal anti-CD22 antibodies", Cell Immunol. 118(1):85-99 (1989).

Lonberg et al., "Antigen-specific human antibodies from mice comprising four distinct genetic modifications", Nature 368:856-9 (1994).

Longo, D. L "Immunotherapy for non-Hodgkin's lymphoma", Curr. Opin. Oncol. 8(5):353-9 (1996).

Losman et al., "Baboon anti-idiotype antibodies mimic a carcinoembryonic antigen epitope", Int J Cancer. Aug. 15, 1990;46(2):310-4.

Lundberg, B. "Preparation of drug-carrier emulsions stabilized with phosphatidylcholine-surfactant mixtures", J. Pharm. Sci. 83(1):72-5 (1994).

Lundberg et al., "Submicron lipid emulsions containing amphipathic polyethylene glycol for use as drug-carriers with prolonged circulation time", Int. J. Pharm. 134:119-127 (1996).

(56) References Cited

OTHER PUBLICATIONS

Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade-non-Hodgkin's lymphoma", Blood. Sep. 15, 1997;90(6):2188-95.
Mason et al., "Value of monoclonal anti-CD22 (p. 135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19 (6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6)1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and Immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2)131-44 (1998).
Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86 (24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.

Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79 (6):1979-83 (1982).
Saltzman et al., "Transport rates of proteins in porous materials with known microgeometry", Biophys. J. 55 (1)163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sharkey et al., "Epratuzumab-SN-38: A New Antibody-Drug Conjugate for the Therapy of Hematologic Malignancies", Mol Cancer Ther. Dec. 16, 2011. [Epub ahead of print].
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B-B cell interactions", J Exp Med. Jan. 1, 1991;173(1):137-46.
Wilson et al., "Genomic structure and chromosomal mapping of the human CD22 gene", J Immunol. Jun. 1, 1993;150 (11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.
Youinou et al., "B lymphocytes on the front line of autoimmunity", Autoimmun Rev. Mar. 2006;5(3):215-21.
Aozasa et al., "The occurrence of monocytoid B-lymphocytes in autoimmune disorders", Mod Pathol. Mar. 1993;6(2)121-4.
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Beers et al., The Merck Manual of Diagnosis and Therapy, Ch. 180, p. 1474-1476; 17th Ed., Whitehouse Station, NJ, Merck Research Labs (1999).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.

(56) References Cited

OTHER PUBLICATIONS

Baum et al., "Initial clinical results with technetium-99m-labeled LL2 monoclonal antibody fragment in the radioimmunodetection of B-cell lymphomas", Cancer. Feb. 1, 1994;73(3 Suppl):896-9.

Belisle et al., "Epitope specificity of the anti-B-cell lymphoma monoclonal antibody, LL2", Proc Am Assoc Cancer Res 1993; 34:481, Abstr #2873.

Bendig, M., "Humanization of Rodent Monoclonal Antibodies by CDR Grafting", Academic Press Inc., New York, NY, vol. 8, (1995), pp. 83-93.

Beum et al., "Binding of rituximab, trastuzumab, cetuximab, or mAb T101 to cancer cells promotes trogocytosis mediated by THP-1 cells and monocytes", J Immunol. Dec. 1, 2008;181(11):8120-32.

Bhat et al., "Human antilipid A monoclonal antibodies bind to human B cells and the i antigen on cord red blood cells", J Immunol. Nov. 1, 1993;151(9):5011-21.

Brozek et al., "Anti-DR antibodies inhibit in vitro production of human rheumatoid factor", J Clin Lab Immunol. Mar. 1990;31(3):105-9.

Carter et al., "Humanization of an anti-p185HER2 antibody for human cancer therapy", Proc. Natl. Acad. Sci. USA 39(10):4285-9 (1992).

Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.

Coloma et al., "Design and production of novel tetravalent bispecific antibodies", Nat. Biotechnol. 15(2):159-63 (1997).

Dillman et al., "Antibodies as cytotoxic therapy", J Clin Oncol. Jul. 1994;12(7):1497-515.

Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).

Ellis et al., "Engineered anti-CD38 monoclonal antibodies for immunotherapy of multiple myeloma", J Immunol. Jul. 15, 1995;155(2):925-37.

Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).

Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.

French et al., "Response of B-cell lymphoma to a combination of bispecific antibodies and saporin", Leuk. Res. 20(7):607-17 (1996).

Ghetie et al., "Evaluation of ricin a chain-containing immunotoxins directed against CD19 and CD22 antigens on normal and malignant human B-cells as potential reagents for in vivo therapy", Cancer Res. 48(9):2610-7 (1988).

Goldenberg et al., "Targeting, dosimetry, and radioimmunotherapy of B-cell lymphomas with iodine-131-labeled LL2 monoclonal antibody", J Clin Oncol. Apr. 1991;9(4):548-64.

Goldenberg, D. M. "New Developments in Monoclonal Antibodies for Cancer Detection and Therapy", CA Cancer J. Clin. 44(1):43-64 (1994).

Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and in Combination with Veltuzumab, a Humanized Anti-CD20 MAb", Blood (ASH Annual Meeting Abstracts) 2010 116: Abstract 3941.

Goldenberg et al., "B cell therapy with the anti-CD22 monoclonal antibody epratuzumab: comment on the editorial by St. Clair and Tedder", Arthritis Rheum. Jul. 2006;54(7):2344; author reply 2344-5.

Gondo et al., "HLA class II antigen associated invariant chain gene expression in malignant lymphoma", Br. J. Haematol. 67(4):413-7 (1987).

Green et al., "Antigen-specific human monoclonal antibodies from mice engineered with human Ig heavy and light chain YACs", Nature Genetics 7:13-21 (1994).

Grossbard et al., "Monoclonal antibody-based therapies of leukemia and lymphoma", Blood. Aug. 15, 1992;80(4):863-78.

Gussow et al., "Humanization of monoclonal antibodies", Methods Enzymol. 1991;203:99-121.

Hansen et al., "Internalization and catabolism of radiolabelled antibodies to the MHC class-II invariant chain by B-cell lymphomas", Biochem. J. 1996, 320:293-300.

Hashida et al., "More useful maleimide compounds for the conjugation of Fab' to horseradish peroxidase through thiol groups in the hinge", J Appl Biochem. Feb.-Apr. 1984;6(1-2):56-63.

Hekman et al. "Initial experience with treatment of human B cell lymphoma with anti-CD19 monoclonal antibody", Cancer Immunol. Immunother. 1991;32(6):364-72.

Hess et al., "Specificity of effector T lymphocytes in autologous graft-versus-host disease: role of the major histocompatibility complex class II invariant chain peptide", Blood 89(6):2203-9 (1997).

Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.

Hudrisier et al., "Capture of target cell membrane components via trogocytosis is triggered by a selected set of surface molecules on T or B cells", J Immunol. Mar. 15, 2007;178(6):3637-47.

Imuran patient information leaflet, GlaxoSmithKline 7076598/5093, Oct. 2004.

Inaoki et al., "CD19-regulated signaling thresholds control peripheral tolerance and autoantibody production in B lymphocytes", J Exp Med. Dec. 1, 1997;186(11):1923-31.

Jones et al., "Replacing the complementarity-determining regions in a human antibody with those from a mouse" Nature 321(6069):522-5 (1986).

Juweid et al., "99Tcm-LL1: a potential new bone marrow imaging agent", Nucl. Med. Commun. 18(2):142-8 (1997).

Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).

Kaminski et al., "Radioimmunotherapy of B-cell lymphoma with [131I]anti-B1 (anti-CD20) antibody", N. Engl. J. Med. 329(7):459-65 (1993).

Kiener et al., "Stimulation of CD40 with purified soluble gp39 induces proinflammatory responses in human monocytes", J Immunol. Nov. 15, 1995;155(10):4917-25.

Kiesel et al., "Removal of cells from a malignant B-cell line from bone marrow with immunomagnetic beads and with complement and immunoglobulin switch variant mediated cytolysis", Leuk. Res. 11(12):1119-25 (1987).

Kohler et al., "Continuous cultures of fused cells secreting antibody of predefined specificity", Nature 256:495-7 (1975).

Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).

Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).

Leung et al., "Chimerization and humanization of a B-cell Lymphoma specific antibody, LL2", Proc Am Assoc Cancer Res 1993; 34:481, Abstr #2872.

Leung et al., "Chimerization of LL2, a Rapidly Internalizing Antibody Specific for B Cell Lymphoma", Hybridoma 13 (6):469-476 (1994).

Leung et al., "Construction and characterization of a humanized, internalizing, b-cell (CD22)-specific, leukemia/lymphma antibody, LL2", Mol. Immunol. 32(17/18):1413-1427 (1995).

Abdu-Allah et al., "Design, synthesis, and structure-affinity relationships of novel series of sialosides as CD22- specific inhibitors", J Med Chem. Nov. 13, 2008;51(21):6665-81.

(56) References Cited

OTHER PUBLICATIONS

Abdu-Allah et al., "CD22-antagonists with nanomolar potency: the synergistic effect of hydrophobic groups at C-2 and C-9 of sialic acid scaffold", Bioorg Med Chem. Mar. 15, 2011;19(6):1966-71.

Advani et al., "SWOG S0910: a phase 2 trial of clofarabine/cytarabine/epratuzumab for relapsed/refractory acute lymphocytic leukaemia", Br J Haematol. May 2014;165(4):504-9.

Al Rayes et al., "Profile of epratuzumab and its potential in the treatment of systemic lupus erythematosus", Drug Des Devel Ther. Nov. 17. 2014;8:2303-10.

Carnahan et al., "Epratuzumab, a humanized monoclonal antibody targeting CD22: characterization of in vitro properties", Clin Cancer Res. Sep. 1, 2003;9(10 Pt 2):3982S-905.

Carnahan et al., "Epratuzumab, a CD22-targeting recombinant humanized antibody with a different mode of action from rituximab", Mol Immunol. Feb. 2007;44(6):1331-41.

Chan et al., "Defective negative regulation of antigen receptor signaling in Lyn-deficient B lymphocytes", Curr Biol. May 7, 1998;8(10):545-53.

Chang et al., "Extensive crosslinking of CD22 by epratuzumab triggers BCR signaling and caspase-dependent apoptosis in human lymphoma cells", MAbs. 2015;7(1):199-211.

Courtney et al., "Sialylated multivalent antigens engage CD22 in trans and inhibit B cell activation", Proc Natl Acad Sci U S A. Feb. 24, 2009;106(8):2500-5.

Daridon et al., "Epratuzumab targeting of CD22 affects adhesion molecule expression and migration of B-cells in systemic lupus erythematosus", Arthritis Res Ther. 2010;12(6):R204.

Doody et al., "A role in B cell activation for CD22 and the protein tyrosine phosphatase SHP", Science. Jul. 14, 1995;269(5221):242-4.

Dorner et al., "Initial clinical trial of epratuzumab (humanized anti-CD22 antibody) for immunotherapy of systemic lupus erythematosus", Arthritis Res Ther. 2006;8(3):R74.

Dorner et al., "The mechanistic impact of CD22 engagement with epratuzumab on B cell function: Implications for the treatment of systemic lupus erythematosus", Autoimmun Rev. Dec. 2015;14(12):1079-86.

Dorner et al., "Targeting CD22 as a strategy for treating systemic autoimmune diseases", Ther Clin Risk Manag. Oct. 2007;3(5):953-9.

Fleischer et al., "Epratuzumab inhibits the production of the proinflammatory cytokines IL-6 and TNF-α, but not the regulatory cytokine IL-10, by B cells from healthy donors and SLE patients", Arthritis Res Ther. Jul. 17, 2005;17:185.

Geppert et al., "Accessory cell independent proliferation of human T4 cells stimulated by immobilized monoclonal antibodies to CD3", J Immunol. Mar. 15, 1987;138(6):1660-6.

Groger et al., "Dermal microvascular endothelial cells express CD32 receptors in vivo and in vitro", J Immunol. Feb. 15, 1996, 15;156(4):1549-56.

Gupta et al., "Multiple signaling pathways induced by hexavalent, monospecific, anti-CD20 and hexavalent, bispecific, anti-CD20/CD22 humanized antibodies correlate with enhanced toxicity to B-cell lymphomas and leukemias", Blood. Oct. 28, 2010;116(17):3258-67.

Hanasaki et al., "Cytokine-induced beta-galactoside alpha-2,6-sialyltransferase in human endothelial cells mediates alpha 2,6-sialylation of adhesion molecules and CD22 ligands", J Biol Chem. Apr. 8, 1994;269(14):10637-43.

Hanasaki et al., "CD22-mediated cell adhesion to cytokine-activated human endothelial cells. Positive and negative regulation by alpha 2-6-sialylation of cellular glycoproteins", J Biol Chem. Mar. 31, 1995;270(13):7533-42.

Hoelzer, D., "Targeted therapy with monoclonal antibodies in acute lymphoblastic leukemia", Curr Opin Oncol. Nov. 2013;25(6):701-6.

Illidge et al., "Radioimmunotherapy in follicular lymphoma", Best Pract Res Clin Haematol. Jun. 2011;24(2):279-93.

Ishigami et al., "Anti-IgM antibody-induced cell death in a human B lymphoma cell line, B104, represents a novel programmed cell death", J Immunol. Jan. 15, 1992;148(2):360-8.

Jacobi et al., "Differential effects of epratuzumab on peripheral blood B cells of patients with systemic lupus erythematosus versus normal controls", Ann Rheum Dis. Apr. 2008;67(4):450-7.

Leonard et al., "Epratuzumab, a humanized anti-CD22 antibody, in aggressive non-Hodgkin's lymphoma: phase I/II clinical trial results", Clin Cancer Res. Aug. 15, 2004;10(16):5327-34.

Leonard et al., "Durable complete responses from therapy with combined epratuzumab and rituximab: final results from an international multicenter, phase 2 study in recurrent, indolent, non-Hodgkin lymphoma", Cancer. Nov. 15, 2008;113(10):2714-23.

Macauley et al., "Antigenic liposomes displaying CD22 ligands induce antigen-specific B cell apoptosis", J Clin Invest. Jul. 2013;123(7):3074-83.

Mateo et al., "D47 ligation induces caspase-independent cell death in chronic lymphocytic leukemia", Nat Med. Nov. 1999;5(11):1277-84.

Mavromatis et al., "Novel therapies for chronic lymphocytic leukemia", Blood Rev. Jun. 2004;18(2):137-48.

Micallef et al., "Epratuzumab with rituximab, cyclophosphamide, doxorubicin, vincristine, and prednisone chemotherapy in patients with previously untreated diffuse large B-cell lymphoma", Blood. Oct. 13, 2011;118 (15):4053-61.

Nitschke, L., "The role of CD22 and other inhibitory co-receptors in B-cell activation", Curr Opin Immunol. Jun. 2005;17(3):290-7.

O'Reilly et al., "Bifunctional CD22 ligands use multimeric immunoglobulins as protein scaffolds in assembly of immune complexes on B cells", J Am Chem Soc. Jun. 18, 2008;130(24):7736-45.

Pan et al., "Detection of Fcgamma receptors on human endothelial cells stimulated with cytokines tumour necrosis factor-alpha (TNF-alpha) and interferon-gamma (IFN-gamma)", Clin Exp Immunol. Jun. 1998;112(3):533-8.

Pezzutto et al., "Amplification of human B cell activation by a monoclonal antibody to the B cell-specific antigen CD22, Bp 130/140", J Immunol. Jan. 1, 1987;138(1):98-103.

Pezzutto et al., "Role of the CD22 human B cell antigen in B cell triggering by anti-immunoglobulin", J Immunol. Mar. 15, 1988;140(6):1791-5.

Qu et al., "Bispecific anti-CD20/22 antibodies inhibit B-cell lymphoma proliferation by a unique mechanism of action", Blood. Feb. 15, 2008;111(4):2211-9.

Raetz et al., "Chemoimmunotherapy reinduction with epratuzumab in children with acute lymphoblastic leukemia in marrow relapse: a Children's Oncology Group Pilot Study", J Clin Oncol. Aug. 1, 2008;26(22):3756-62.

Rao et al., "Evaluation of epratuzumab as a biologic therapy in systemic lupus erythematosus", Immunotherapy. 2014;6(11)1165-75.

Rudge et al., "Interleukin 4 reduces expression of inhibitory receptors on B cells and abolishes CD22 and Fc gamma RII-mediated B cell suppression", J Exp Med. Apr. 15, 2002;195(8):1079-85.

Sharkey et al., "Epratuzumab-SN-38: a new antibody-drug conjugate for the therapy of hematologic malignancies", Mol Cancer Ther. Jan. 2012;11(1):224-34.

Sieger et al., "CD22 ligation inhibits downstream B cell receptor signaling and Ca(2+) flux upon activation", Arthritis Rheum. Mar. 2013;65(3):770-9.

Steinfeld et al., "Epratuzumab (humanised anti-CD22 antibody) in primary Sjögren's syndrome: an open-label phase I/II study", Arthritis Res Ther. 2006;8(4):R129.

Strand et al., "Epratuzumab for patients with moderate to severe flaring SLE: health-related quality of life outcomes and corticosteroid use in the randomized controlled ALLEVIATE trials and extension study SL0006", Rheumatology (Oxford). Mar. 2014;53(3):502-11.

Tsuru et al., "Safety, pharmacokinetics, and pharmacodynamics of epratuzumab in Japanese patients with moderate-to-severe systemic lupus erythematosus: Results from a phase ½ randomized study", Mod Rheumatol. Jan. 2016;26(1):87-93.

(56) References Cited

OTHER PUBLICATIONS

Tuscano et al., "Engagement of the adhesion receptor CD22 triggers a potent stimulatory signal for B cells and blocking CD22/CD22L interactions impairs T-cell proliferation", Blood. Jun. 1, 1996;87(11):4723-30.

Wallace et al., "Epratuzumab for systemic lupus erythematosus", Lupus. Apr. 2013;22(4):400-5.

Wallace et al., "Long-term safety and efficacy of epratuzumab in the treatment of moderate-to-severe systemic lupus erythematosus: results from an open-label extension study", Arthritis Care Res (Hoboken). Aug. 28, 2015.

Wallace et al., "Efficacy and safety of epratuzumab in patients with moderate/severe flaring systemic lupus erythematosus: results from two randomized, double-blind, placebo-controlled, multicentre studies (ALLEVIATE) and follow-up", Rheumatology (Oxford). Jul. 2013;52(7)1313-22.

Wallace et al., "Efficacy and safety of epratuzumab in patients with moderate/severe active systemic lupus erythematosus: results from EMBLEM, a phase IIb, randomised, double-blind, placebo-controlled, multicentre study", Ann Rheum Dis. Jan. 2014;73(1):183-90.

Walshe et al., "Induction of cytosolic calcium flux by CD20 is dependent upon B Cell antigen receptor signaling", J Biol Chem. Jun. 20, 2008;283(25):16971-84.

\* cited by examiner

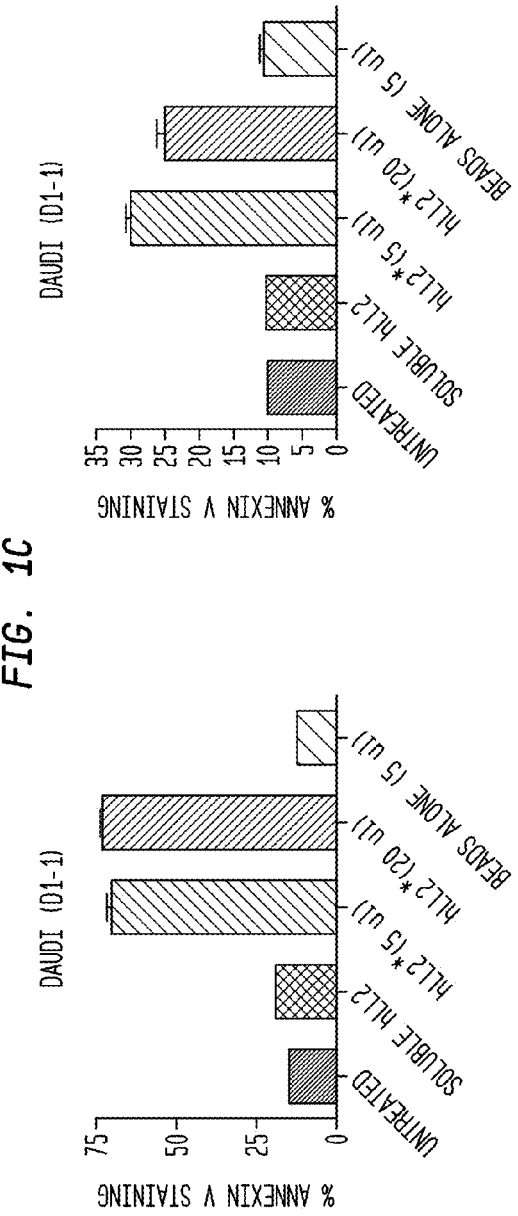
FIG. 1C
FIG. 1D
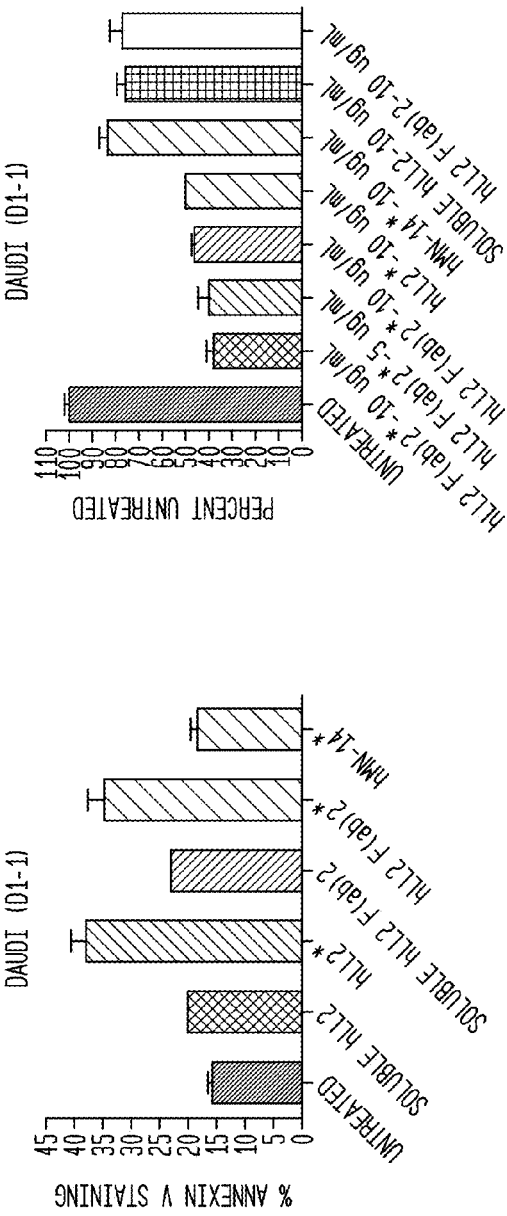

| DAUDI | % |
|---|---|
| UNTREATED | 22.9 |
| hLL2 | 23.8 |
| hLL2* | 66.1 |
| hMN-14* | 24.4 |
| HUV-EC | 21.4 |
| HUV-EC/hLL2 | 60.1 |

CROSSLINKING OF CD22 BY EPRATUZUMAB TRIGGERS BCR SIGNALING AND CASPASE-DEPENDENT APOPTOSIS IN HEMATOPOIETIC CANCER CELLS

RELATED APPLICATIONS

This application is a continuation-in-part of U.S. patent application Ser. No. 14/243,512, filed Apr. 2, 2014, which was a continuation-in-part of U.S. patent application Ser. No. 13/693,476, filed Dec. 4, 2012, which claimed the benefit under 35 U.S.C. 119(e) of Provisional U.S. Patent Application Ser. Nos. 61/566,828, filed Dec. 5, 2011; 61/609,075, filed Mar. 9, 2012; 61/682,508, filed Aug. 13, 2012; and 61/718,226, filed Oct. 25, 2012. U.S. patent application Ser. No. 14/243,512 claimed the benefit under 35 U.S.C. 119(e) of Provisional U.S. Patent Application Ser. Nos. 61/808,005, filed Apr. 3, 2013, 61/832,558, filed Jun. 7, 2013 and 61/941,100, filed Feb. 18, 2014. This application claims the benefit under 35 U.S.C. 119(e) of Provisional U.S. Patent Application Ser. No. 62/054,581, filed Sep. 24, 2014. The text of each claimed priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 22, 2015, is named IMM349US1_SL.txt and is 13,893 bytes in size.

FIELD OF THE INVENTION

This invention relates to compositions and methods of use of antibodies against human CD22. Preferably, the antibodies provide extensive cross-linking of CD22 in vitro or in vivo. More preferably, antibody based cross-linking is of use to treat hematopoietic cancer by mechanisms involving BCR signaling and/or caspase-dependent apoptosis. Other changes induced by cross-linking CD22 may include phosphorylation of CD22, CD79a and CD79b, along with their translocation to lipid rafts, both of which were essential for effecting caspase-dependent apoptosis. Still other changes induced by CD22 cross-linking by anti-CD22 antibodies may include stabilization of F-actin, phosphorylation of Lyn, ERKs and JNKs, generation of reactive oxygen species (ROS), decrease in mitochondria membrane potential ($\Delta\psi_m$), upregulation of pro-apoptotic Bax, and downregulation of anti-apoptotic Bcl-xl and Mcl-1. These changes suggest that the in vivo mechanism of action of anti-CD22 antibody therapy may involve the unmasking of CD22 to facilitate the trans-interaction of B cells with vascular endothelium.

BACKGROUND

CD22 is a 135-kD type I transmembrane sialoglycoprotein of the immunoglobulin (Ig) superfamily. CD22 expression is specific to B cells can be detected in the cytoplasm of pro-B and pre-B cells, as well as on the surface of IgM$^+$ B cells upon the appearance of IgD, but not on terminally-differentiated plasma cells (Tedder et al., 1997, Ann Rev Immunol 15:481-504). CD22 is strongly expressed on follicular, mantle and marginal-zone B cells, but is weakly present in germinal B cells (Dorner & Goldenberg, 2007, Ther Clin Risk Manag 3:954-59). CD22 is an inhibitory co-receptor that downmodulates B-cell receptor (BCR) signaling by setting a signaling threshold that prevents over-stimulation of B cells (Nitschke, 2005, Curr Opin Immunol 17:290-97).

Structurally, CD22 in its extracellular region comprises 7 immunoglobulin-like domains, of which the two N-terminal domains are involved in ligand binding (Law et al., 1995, J Immunol 155:3368-76). The cytoplasmic tail of CD22 contains 6 conserved tyrosine (Y) residues, four of which ($Y^{762}$, $Y^{796}$, $Y^{822}$, and $Y^{842}$) in hCD22 are considered to be localized within the immunoreceptor tyrosine-based inhibition motifs (ITIM) (Wilson et al., 1991, J Exp Med 173:137-46; Ravetch & Lanier, 2000, Science 290:84-9; Sato et al., 1998, Semin Immunol 10:287-97). These tyrosine residues also fit in the specific internalization motifs of YXXØ (where Ø denotes a hydrophobic residue) (Bonifacino et al., 2003, Ann Rev Biochem 72:395-447), which mediate the recruitment of CD22 to clathrin-coated pits and are required for the internalization of CD22 (John et al., 2003, J Immunol 170"3534-43). Whereas endocytosed CD22 has been documented to be degraded intracellularly (Shan & Press, 1995, J Immunol 154:4466-75), a recent report contended that CD22 instead is constitutively recycled back to the cell surface (O'Reilly et al., 2011, J Immunol 186:1554-63). Functionally, CD22 recognizes α2,6-linked sialic acids on glycoconjugates in both cis (on the same cell) and trans (on different cells) interactions, and modulates B cells via interaction with CD79a and CD79b, the signaling components of the BCR complex (Razi & Varki, 1998 95:7469-74; Engels et al., 1993, J Immunol 150:4719-32; Leprince et al., 1993, Proc Natl Acad Sci USA 90:3236-40). Crosslinking the BCR with cognate antigens or appropriate antibodies against membrane immunoglobulin (mIg) on the cell surface induces translocation of the aggregated BCR complex to lipid rafts (Petri et al., 2000, J Immunol 165:1220-27), where CD79a, CD79b and CD22, among others, are phosphorylated by Lyn (Smith et al., 1998, J Exp Med 187:807-11), which in turn triggers various downstream signaling pathways, culminating in proliferation, survival, or death (Niiro et al., 2002, Nat Rev Immunol 2:945-56).

Antibodies against CD22, such as epratuzumab (hLL2), have been used for treatment of a variety of cancers and autoimmune diseases, including but not limited to acute lymphoblastic leukemia (Hoelzer et al., 2013, Curr Opin Oncol 25:701-6), chronic lymphocytic leukemia (Macromatis & Cheson, 2004, Blood Rev 18:137-48), non-Hodgkin's lymphoma (Leonard et al., 2004, Clin Cancer Res 10:5327-34; Dorner & Goldenberg, 2007), follicular lymphoma (Illidge & Morchhauser, 2011, Best Pract Res Clin Haematol 24:279-93), diffuse large B-cell lymphoma (Micallef et al., 2011, Blood 118:4053-61), mantle cell lymphoma (Sharkey et al., 2012, Mol Cancer Ther 11:224-34), systemic lupus erythematosus (Dorner & Goldenberg, 2007; Strand et al., 2014, Rheumatology 53:502-11; Wallace & Goldenberg, 2013, Lupus 22:400-5; Wallace et al., 2013, Rheumatology 52:1313-22; Wallace et al., 2014, Ann Rheum Dis 73:183-90), and primary Sjögren's syndrome (Steinfeld et al., 2006, Arthritis Res Ther 8:R129; Dorner & Goldenberg, 2007). Because CD22 regulates B-cell functions and survival, it is an important link for modulating humoral immunity and proliferation of B-cell lymphomas and a target for therapeutic antibodies in cancer and autoimmune disease (Dorner & Goldenberg, 2007).

Epratuzumab (hLL2), a humanized monoclonal antibody specific for human CD22 (Leung et al., 1995, Mol Immunol 32:1413-27), is currently under clinical investigation for the treatment of non-Hodgkin lymphoma (NHL) (Leonard et al., 2004, Clin Cancer Res 10:5327-34; Leonard et al., 2009, Cancer 113:2714-23), pediatric and adult acute lymphoblastic leukemia (Raetz et al., 2008, J Clin Oncol 26:3756-62; Advani et al., 2014, Br J Haematol 165:504-9), systemic lupus erythematosus (SLE) (Wallace et al., 2013, Lupus 22:400-5; Wallace et al., 2013, Rheumatology 52:1313-22; Strand et al., Rheumatology 53:502-11), and has shown promise in patients with primary Sjögren's syndrome in a phase I/II study (Steinfeld et al., 2006, Arthritis Res Ther 8:R129). Research on anti-CD22 antibodies, which can be either blocking or nonblocking (Tuscano et al., 1996, Blood 87:4723-30), has also led to intriguing observations that CD22 may positively or negatively affect BCR-mediated signaling pathways, with the ultimate outcome depending on the characteristics of the B cells (differentiation stage, expression of BCR isotype, and being malignant, abnormal, or normal) (Tuscano et al., 1996, Blood 87:4723-30; Pezzutto et al, 1987, J Immunol 138:98-103; Pezzutto et al., 1988, J Immunol 140:1791-95; Nitschke et al., 2005, Curr Opin Immunol 17:290-97). Thus, fully understanding the role of CD22 in B-cell malignancies, as well as B-cell-implicated autoimmune diseases, is of considerable importance for improving CD22-targeted therapies.

As a single agent, epratuzumab is well-tolerated, depleting circulating B cells transiently in NHL patients (Leonard et al., 2009, Cancer 113:2714-23), and by an average of 35% at 18 weeks in SLE patients (Dorner et al., 2006, Arthritis Res Ther 8:R74). When evaluated in vitro, epratuzumab displayed modest antibody-dependent cellular cytotoxicity, but no complement-dependent cytotoxicity (Carnahan et al., 2007, Mol Immunol 44:1331-41), and was shown to inhibit the proliferation of B cells from patients with SLE, but not from normal donors, under all culture conditions (Jacobi et al., 2008, Ann Rheum Dis 67:450-57). Additional studies with B cells from SLE patients indicated that (i) binding of epratuzumab was particularly enhanced on $CD27^-$ compared to $CD27^+$ B cells (Daridon et al., 2010, Arthritis Res Ther 12:R204); (ii) a decrease of CD62L and β7 integrin and an increase of β1 integrin in the cell surface expression, as well as an enhanced migration towards CXCL12, were noted for $CD27^-$ B cells preferentially (Daridon et al., 2010); and (iii) the in vivo effects of epratuzumab in SLE patients included an immediate and sustained (up to 18 weeks) decrease in CD22 surface expression on circulating $CD27^-$ and $CD27^+$ B cells (Daridon et al., 2010). More recently, pre-incubation with F(ab')$_2$ of epratuzumab was reported to inhibit calcium mobilization and phosphorylation of Syk and PLCγ2 in normal human B cells after BCR stimulation (Sieger et al., 2013, Arthritis Rheum 65:770-79), and the ability of epratuzumab-based agents to effectively mediate Fc-dependent trogocytosis of multiple B-cell surface markers by FcγR-bearing cells, was established (Rossi et al., 2013, Blood 122:3020-29; Rossi et al., 2014, PLoS ONE 9:e98315).

In cell lines and xenografts of human Burkitt lymphoma, soluble epratuzumab, although capable of phosphorylating CD22 (Carnahan et al., 2003, Clin Cancer Res 9:3982s-90s) and translocating CD22 to lipid rafts (Qu et al, 2008, Blood 111:2211-19), as demonstrated in vitro, was not cytotoxic or cytostatic (Carnahan et al., 2007, Mol Immunol 44:1331-41; Qu et al., 2008), and displayed only minimal toxicity even when crosslinked by goat anti-human IgG Fcγ (GAH) (Carnahan et al., 2007). On the other hand, in vitro cytotoxicity of epratuzumab comparable to that achievable with anti-IgM (10 μg/mL) could be consistently demonstrated in Ramos and D1-1, a subclone of Daudi selected for a high expression of membrane IgM (mIgM), when the antibody was immobilized to plastic plates, or added in combination with suboptimal amounts of anti-IgM (for example, 1 μg/mL or less) along with GAH (Carnahan et al., 2007). Despite all of this knowledge, how epratuzumab kills or modulates normal and malignant B cells in patients, and inhibits the growth of lymphoma lines in vitro upon immobilization, remains poorly understood. A need exists in the field for improved methods of use of anti-CD22 antibodies, based on their mechanism(s) of action of anti-cancer and/or anti-autoimmune disease activity.

SUMMARY

The present invention concerns compositions and methods of use of antibodies against CD22. In preferred embodiments, use of the antibodies provides extensive cross-linking of CD22 on B cells, which in turn induces phosphorylation of CD22, CD79a and CD79b, along with their translocation to lipid rafts, stabilization of F-actin, phosphorylation of Lyn, ERKs and JNKs, generation of reactive oxygen species (ROS), decrease in mitochondria membrane potential ($\Delta\psi_m$), upregulation of pro-apoptotic Bax, and downregulation of anti-apoptotic Bcl-xl and Mcl-1. These in turn result in BCR signaling and/or caspase-dependent apoptosis. Such mechanisms are of use for treating hematopoietic cancer, B-cell related autoimmune disease and/or immune system dysfunction, such as GVHD or organ transplant rejection.

The anti-CD22 antibody also induces trogocytosis of BCR-related antigens, resulting in decreased levels of CD19, CD20, CD21, CD22, CD79b, CD44, CD62L and β7-integrin on the surface of affected B cells. B cell antigens, particularly CD19, inhibit B cell activation in response to T cell-dependent antigens and has a therapeutic effect on autoimmune and immune dysfunction diseases, which are mediated at least in part by B cell activation.

One example of a preferred anti-CD22 antibody is epratuzumab, which induces trogocytosis without incurring direct cytotoxicity to B cells, thus providing an unexpected and substantial advantage in treating autoimmune diseases, such as systemic lupus erythematosus (SLE), ANCA-associated vasculitides, and other autoimmune diseases. However, other anti-CD22 antibodies that may be used are publicly available and/or known in the art. Such known and/or publicly available antibodies include, but are not limited to, inotuzumab (Pfizer, Groton, Conn.), CAT-3888 (Cambridge Antibody Technology Group, Cambridge, England), CAT-8015 (Cambridge Antibody Technology Group, Cambridge, England), HB22.7 (Duke University, Durham, N.C.) and RFB4 (e.g., Invitrogen, Grand Island, N.Y.; Santa Cruz Biotechnology, Santa Cruz, Calif.).

Exemplary autoimmune or immune dysfunction diseases include acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, fibrosing alveolitis, graft-versus-host disease (GVHD), organ transplant rejection, sepsis, septicemia and inflammation.

Exemplary hematopoietic cancers include non-Hodgkin's lymphoma, B-cell acute and chronic lymphoid leukemias, Burkitt lymphoma, Hodgkin's lymphoma, mantle cell lymphoma, hairy cell leukemia, multiple myeloma and Waldenstrom's macroglobulinemia.

An antibody of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. Techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences. As discussed below, techniques for production of human antibodies are also well known.

The antibody may also be multivalent, or multivalent and multispecific. The antibody may include human constant regions of IgG1, IgG2, IgG3, or IgG4. Preferably, the allotype of the antibody may be selected to minimize host immunogenic response to the administered antibody, as discussed in more detail below. A preferred allotype is a non-G1m1 allotype (nG1m1), such as G1m3, G1m3,1, G1m3,2 or G1m3,1,2. The non-G1m1 allotype is preferred for decreased antibody immunoreactivity. Surprisingly, repeated subcutaneous administration of concentrated nG1m1 antibody was not found to induce significant immune response, despite the enhanced immunogenicity of subcutaneous administration.

The anti-CD22 antibody, or antigen-binding fragments thereof, may be administered as a naked antibody or fragment, either alone or in combination with one or more therapeutic agents. In other embodiments, the antibody or fragment thereof may be conjugated to one or more therapeutic agents to form an immunoconjugate. Therapeutic agents may be selected from the group consisting of a drug, prodrug, immunomodulator, cytokine, chemokine, pro-apoptotic agent, anti-angiogenic agent, tyrosine kinase inhibitor, Bruton kinase inhibitor, sphingosine inhibitor, enzyme, hormone, photoactive agent, siRNA and RNAi.

The drug to be used may be selected from the group consisting of an anthracycline, a camptothecin, a tubulin inhibitor, a maytansinoid, a calicheamycin, an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a vinca alkaloid, a substituted urea, a methyl hydrazine derivative, an adrenocortical suppressant, a hormone antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, a pro-apoptotic agent, and a combination thereof.

Specific drugs of use may be selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyanomorpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839.

Immunomodulators of use may be selected from the group consisting of erythropoietin, thrombopoietin, tumor necrosis factor-α (TNF), granulocyte-colony stimulating factor (G-CSF), granulocyte macrophage-colony stimulating factor (GM-CSF), interferon-α, interferon-β, interferon-γ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, angiostatin, thrombospondin, endostatin and lymphotoxin (LT).

Toxins of use may be selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

A radionuclide of use may include $^{14}C$, $^{13}N$, $^{15}O$, $^{32}P$, $^{33}P$, $^{47}SC$, $^{51}Cr$, $^{57}Co$, $^{58}Co$, $^{59}Fe$, $^{62}Cu$, $^{67}Cu$, $^{67}Ga$, $^{67}Ga$, $^{75}Br$, $^{75}Se$, $^{75}Se$, $^{76}Br$, $^{77}As$, $^{77}Br$, $^{80m}Br$, $^{89}Sr$, $^{90}Y$, $^{95}Ru$, $^{97}Ru$, $^{99}Mo$, $^{99m}Tc$, $^{103m}Rh$, $^{103}Rh$, $^{105}Rh$, $^{105}Ru$, $^{107}Hg$, $^{109}Pd$, $^{109}Pt$, $^{111}Ag$, $^{111}In$, $^{113m}In$, $^{119}Sb$, $^{121m}Te$, $^{122m}Te$, $^{125}I$, $^{125m}Te$, $^{126}I$, $^{131}I$, $^{133}I$, $^{142}Pr$, $^{143}Pr$, $^{149}Pm$, $^{152}Dy$, $^{153}Sm$, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{255}$Fm or $^{227}$Th.

Exemplary tyrosine kinase inhibitors include, but are not limited to canertinib, dasatinib, erlotinib, gefitinib, imatinib, lapatinib, leflunomide, nilotinib, pazopanib, semaxinib, sorafenib, sunitinib, sutent and vatalanib. A specific class of tyrosine kinase inhibitor is the Bruton tyrosine kinase inhibitor. Bruton tyrosine kinase (Btk) has a well-defined role in B-cell development. Bruton kinase inhibitors include, but are not limited to, PCI-32765 (ibrutinib), PCI-45292, GDC-0834, LFM-A13 and RN486.

These and other known therapeutic modalities may be used in combination with the anti-CD22 antibodies disclosed herein.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 1C. Evaluation of growth-inhibition and apoptosis in D1-1 and Ramos cells. Apoptosis as determine by Annexin V staining following the indicated treatments of D1-1 and Ramos cells for 24 and 48 h, respectively. Error bars represent standard deviation (SD), where n=3. Significant differences compared to untreated or nonspecific antibody are indicated with ˆ (P<0.005) and # (P<0.05).

FIG. 1D. Evaluation of growth-inhibition and apoptosis in D1-1 and Ramos cells. Plate-immobilized F(ab')$_2$ of epratuzumab (hLL2 F(ab')$_2$*) effectively induced apoptosis (left panel) and inhibited proliferation (right panel) in D1-1 cells as determined by the annexin V assay at 24 h and the MTS assay after 4 days, respectively. Error bars represent standard deviation (SD), where n=3. Significant differences compared to untreated or nonspecific antibody are indicated with ˆ (P<0.005) and # (P<0.05).

DETAILED DESCRIPTION

Definitions

Figure 1A:
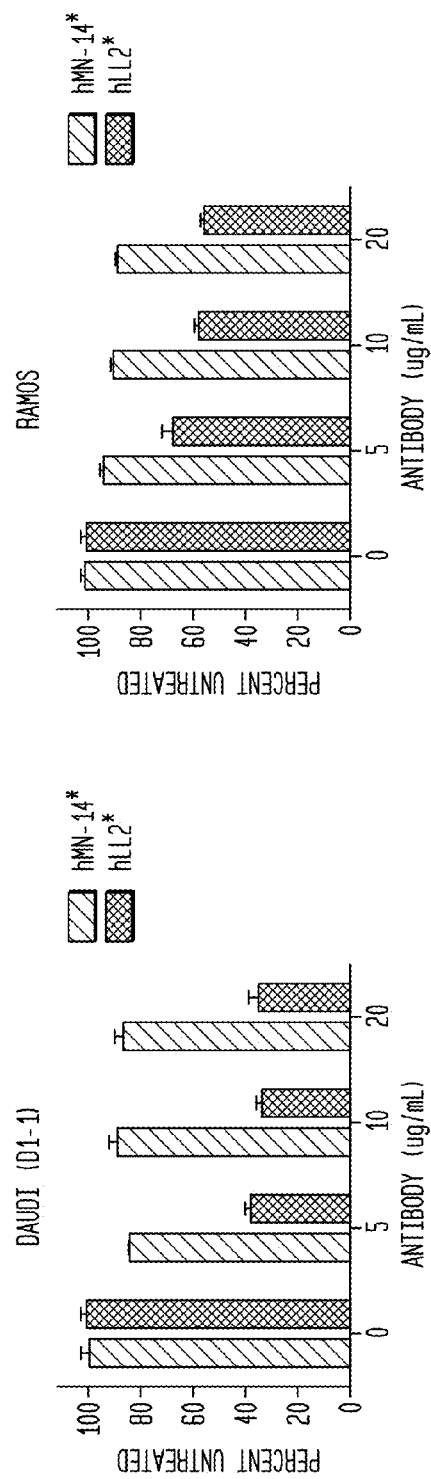
FIG. 1A. Evaluation of growth-inhibition and apoptosis in D1-1 and Ramos cells. Cell viability determined by the MTS assay after 4-day incubation for the Dried-I format of epratuzumab (hLL2*) or labetuzumab (hMN-14*). Error bars represent standard deviation (SD), where n=3. Significant differences compared to untreated or nonspecific antibody are indicated with ˆ (P<0.005) and # (P<0.05).

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

The term about is used herein to mean plus or minus ten percent (10%) of a value. For example, "about 100" refers to any number between 90 and 110.

An antibody, as used herein, refers to a full-length (i.e., naturally occurring or formed by normal immunoglobulin gene fragment recombinatorial processes) immunoglobulin molecule (e.g., an IgG antibody) or an antigen-binding portion of an immunoglobulin molecule, such as an antibody fragment. An antibody or antibody fragment may be conjugated or otherwise derivatized within the scope of the claimed subject matter. Such antibodies include but are not limited to IgG1, IgG2, IgG3, IgG4 (and IgG4 subforms), as well as IgA isotypes. In preferred embodiments, antibodies and antibody fragments are selected to bind to human antigens.

An antibody fragment is a portion of an antibody such as $F(ab')_2$, $F(ab)_2$, Fab', Fab, Fv, scFv (single chain Fv), single domain antibodies (DABs or VHHs) and the like, including the half-molecules of IgG4 cited above (van der Neut Kolfschoten et al. (Science 2007; 317(14 September):1554-1557). A commercially available form of single domain antibody is referred to as a nanobody (ABLYNX®, Ghent, Belgium). Regardless of structure, an antibody fragment of use binds with the same antigen that is recognized by the intact antibody. The term "antibody fragment" also includes synthetic or genetically engineered proteins that act like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"). The Fv fragments may be constructed in different ways to yield multivalent and/or multispecific binding forms. In the case of multivalent, they have more than one binding site against the specific epitope, whereas with multispecific forms, more than one epitope (either of the same antigen or against one antigen and a different antigen) is bound.

A naked antibody is generally an entire antibody that is not conjugated to a therapeutic agent. This is so because the Fc portion of the antibody molecule provides effector or immunological functions, such as complement fixation and ADCC (antibody-dependent cell cytotoxicity), which set mechanisms into action that may result in cell lysis. However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with disease progression. Naked antibodies include both polyclonal and monoclonal antibodies, and fragments thereof, that include murine antibodies, as well as certain recombinant antibodies, such as chimeric, humanized or human antibodies and fragments thereof. As used herein, "naked" is synonymous with "unconjugated," and means not linked or conjugated to a therapeutic agent.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A humanized antibody is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A human antibody is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, the Examples section of each of which is incorporated herein by reference.

A therapeutic agent is a molecule or atom that is useful in the treatment of a disease. Examples of therapeutic agents include, but are not limited to, antibodies, antibody fragments, conjugates, drugs, cytotoxic agents, proapoptotic agents, toxins, nucleases (including DNAses and RNAses), hormones, immunomodulators, chelators, boron compounds, photoactive agents or dyes, radioisotopes or radionuclides, oligonucleotides, interference RNA, peptides, anti-angiogenic agents, chemotherapeutic agents, cyokines, chemokines, prodrugs, enzymes, binding proteins or peptides or combinations thereof.

An immunoconjugate is an antibody, antibody fragment or other antibody moiety conjugated to a therapeutic agent.

As used herein, the term antibody fusion protein is a recombinantly-produced antigen-binding molecule in which one or more natural antibodies, single-chain antibodies or antibody fragments are linked to another moiety, such as a protein or peptide, a toxin, a cytokine, a hormone, etc. In certain preferred embodiments, the fusion protein may comprise two or more of the same or different antibodies, antibody fragments or single-chain antibodies fused together, which may bind to the same epitope, different epitopes on the same antigen, or different antigens.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation.

Trogocytosis Induced by Anti-CD22

In certain embodiments, the subject anti-CD22 antibody induces trogocytosis of multiple surface markers, which include, but are not limited to, CD19, CD21, CD20, CD22 and CD79b on normal, lupus, and malignant B cells via monocytes, NK cells and granulocytes. Preferably, the anti-CD22 antibody displays little or negligible direct cytotoxicity to normal B cells based on an in vitro cell proliferation assay that shows less than 20% growth inhibition when compared with untreated control, yet reduces CD19, CD21, CD20, CD22, and CD79b to 20% or more of the untreated control via trogocytosis in the presence of peripheral blood mononuclear cells (PBMCs) or purified FcγR-positive cells, such as NK cells, monocytes and granulocytes. A preferred anti-CD22 antibody is epratuzumab, which induces trogocytosis without incurring direct cytotoxicity to B cells, thus providing an unexpected and substantial advantage in treating autoimmune diseases, such as systemic lupus erythematosus (SLE), ANCA-associated vasculitides, and other autoimmune diseases.

The trogocytosis induced by anti-CD22 antibody reduces levels of regulators of antigen-specific B-cell receptor (BCR), such as CD19, CD20, CD21, CD22 and CD79b on the surface of affected B cells. Reduction in these BCR regulators, particularly CD19, inhibits B cell activation in response to T cell-dependent antigens and has a therapeutic effect on autoimmune and immune dysfunction diseases, which are mediated at least in part by B cell activation. The efficacy of anti-CD22 antibodies for therapeutic use in autoimmune and/or immune dysfunction diseases is correlated with the trogocytosis-mediated decrease in the levels of BCR regulators on the cell surface, particularly that of CD19.

Antibodies against CD22 are known in the art and any such known antibody might be used in the claimed compositions and methods. An exemplary anti-CD22 antibody is hLL2 (epratuzumab), disclosed for example in U.S. Pat. No. 5,789,554, the Examples section of which is incorporated herein by reference. The hLL2 antibody is a humanized anti-CD22 antibody comprising light chain CDR sequences CDR1 (KSSQSVLYSANHKYLA, SEQ ID NO:1), CDR2 (WASTRES, SEQ ID NO:2), and CDR3 (HQYLSSWTF, SEQ ID NO:3) and the heavy chain CDR sequences CDR1 (SYWLH, SEQ ID NO:4), CDR2 (YINPRNDYTEYNQN-FKD, SEQ ID NO:5), and CDR3 (RDITTFY, SEQ ID NO:6), along with framework (FR) and constant region sequences of human antibodies. Other known anti-CD22 antibodies of potential use include, but are not limited to, inotuzumab (Pfizer, Groton, Conn.), CAT-3888 (Cambridge Antibody Technology Group, Cambridge, England), CAT-8015 (Cambridge Antibody Technology Group, Cambridge, England), HB22.7 (Duke University, Durham, N.C.) and RFB4 (e.g., Invitrogen, Grand Island, N.Y.; Santa Cruz Biotechnology, Santa Cruz, Calif.).

CD22 Masking

CD22 is an inhibitory coreceptor on the surface of B cells that attenuates BCR signaling and thereby B cell activation (Courtney et al., 2009, Proc Natl Acad Sci USA 106:2500-05). CD22 function is modulated by interaction with extracellular glycan ligands, mediated through its N-terminal Ig domain (Collins et al., 2006, J Immunol 177:2994-3003). The preferred ligand for CD22 consists of α2,6-linked sialic acid-bearing glycans (CD22L), expressed on B and T cells (Lajaunias et al., 2003, Arthritis & Rheumatism 48:1612-21). The extracellular domain of CD22 shows sequence similarity with the Siglec (sialic acid-binding Ig-like lectin) subgroup of the Ig superfamily and is implicated in adhesion of B cells to various cell types, such as lymphocytes, monocytes, erythrocytes and endothelial cells (Lajaunias et al., 2003). It is generally accepted that binding to CD22 is blocked or "masked" by various CD22L-containing glycoproteins (which include CD22 itself, anti-IgM, CD45, etc.) located on the same cell (cis interaction) (see, e.g., Collins et al., 2004, Proc Natl Acad Sci USA 101:6104-09). CD22 that has been masked by cis interaction is not available for binding to different cells (trans interaction), such as T cells, endothelial cells, selected cancer cells, etc. that also contain CD22L-glycoproteins (Collins et al., 2004). It has been suggested that cis ligands are important modulators of the activity of CD22 as a regulator of B cell signaling (Collins et al., 2004). The trans interactions appear to be involved in B cell interactions with other cell types, such as activation of T cells in vitro (Collins et al., 2004). In mixed lymphocyte costimulatory assays, antibodies that inhibited CD22 binding to CD22L also inhibited T cell activation (Collins, 2004). Conversely, activation of B cells is reported to result in unmasking of CD22, which facilitates trans interactions.

hLL2 (epratuzumab) is a non-blocking anti-CD22 antibody, i.e., one that does not directly interfere with binding of CD22 to CD22L. The present disclosure indicates that exposure to epratuzumab pulls CD22 away from its endogenous, cis-binding ligands (such as BCR-IgM) and thus promotes its trans-interaction with other cells that bear CD22L. However, this effect can only be induced by extensive crosslinking of CD22 via immobilized hLL2 in vitro or likely adhering to endothelium in vivo. In essence, there are three levels of engaging CD22 by anti-CD22, bivalent, multivalent (via anti-Fc), and extensive crosslinking (requiring immobilization), which result in increasing perturbation of CD22, BCR and actin cytoskeleton. Our data indicate that the in vitro immobilization of epratuzumab on an artificial plate can be mimicked by a monolayer of endothelial cells, which suggest that unmasking of CD22 by epratuzumab or other non-blocking anti-CD22 antibodies are significant for in vivo therapeutic effect in hematopoietic cancers and autoimmune diseases such as SLE.

Preparation of Monoclonal Antibodies

An antibody of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. Techniques for humanization of murine antibodies by replacing murine framework and constant region sequences with corresponding human antibody framework and constant region sequences are well known in the art and have been applied to numerous murine anticancer antibodies. Antibody humanization may also involve the substitution of one or more human framework amino acid residues with the corresponding residues from the parent murine framework region sequences. As discussed below, techniques for production of human antibodies are also well known.

The compositions, formulations and methods described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)). General techniques for cloning murine immunoglobulin variable domains have been disclosed, for example, by the publication of Orlandi et al., Proc. Nat'l Acad. Sci. USA 86: 3833 (1989).

Chimeric Antibodies

A chimeric antibody is a recombinant protein that contains the variable domains including the CDRs derived from one species of animal, such as a rodent antibody, while the remainder of the antibody molecule; i.e., the constant domains, is derived from a human antibody. Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and $IgG_1$ constant region domains. This publication also provides the nucleotide sequences of the LL2 light and heavy chain variable regions, $V_k$ and $V_H$, respectively.

Humanized Antibodies

A chimeric monoclonal antibody can be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)). Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

Human Antibodies

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., Molecular Cloning, A laboratory manual, 2$^{nd}$ Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., Hybridoma, 13:469

(1994)). The expression vectors can be co-transfected into an appropriate cell and supernatant fluids monitored for production of a chimeric, humanized or human antibody. Alternatively, the $V_\kappa$ and $V_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:8) and veltuzumab (SEQ ID NO:7).

```
Veltuzumab heavy chain constant region sequence
                                          (SEQ ID NO: 7)
ASTKGPSVFPLAPPPSKSTSGGTAALGCLVKDYFPEPVTVSWNSGALTSG

VHTFPAVLQSSGLYSLSSVVTVPSSSLGTQTYICNVNHKPSNTKVDKRVE

PKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSR
```

```
W QQGNVFSCSVMHEALHNHYTQKSLSLSPGK

Rituximab heavy chain constant region sequence
                                          (SEQ ID NO: 8)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | | | |
|---|---|---|---|---|---|---|---|
| | Complete allotype | 214 (allotype) | | 356/358 (allotype) | | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1 m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies

In various embodiments, the claimed methods and compositions may utilize any of a variety of antibodies known in the art. For example, therapeutic use of anti-CD22 antibodies may be supplemented with one or more antibodies against other disease-associated antigens. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), MN-15 (anti-CEACAM6), Mu-9 (anti-colon-specific antigen-p), Immu 31 (an anti-alpha-fetoprotein), TAG-72 (e.g., CC49), R1 (anti-IGF-1R), Tn, J591 or HuJ591 (anti-PSMA (prostate-specific membrane antigen), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), GA101 (anti-CD20; obinutuzumab) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,151,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 5,789,554), hMu-9 (U.S. Pat. No. 7,387,772), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575), the text of each recited patent or application is incorporated herein by reference with respect to the Figures and Examples sections.

Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); OKT3 (anti-CDR3); anti-CD40L (UCB, Brussels, Belgium); natalizumab (anti-α4 integrin) and omalizumab (anti-IgE).

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. Nos. 4,704,692, 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, 2$^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797; Hwang and Foote, 2005, Methods 36:3-10; Clark, 2000, Immunol Today 21:397-402; J Immunol 1976 117:1056-60; Ellison et al., 1982, Nucl Acids Res 13:4071-79; Stickler et al., 2011, Genes and Immunity 12:213-21).

Multispecific and Multivalent Antibodies

Methods for producing bispecific antibodies include engineered recombinant antibodies which have additional cysteine residues so that they crosslink more strongly than the more common immunoglobulin isotypes. (See, e.g., FitzGerald et al, Protein Eng. 10(10):1221-1225, (1997)). Another approach is to engineer recombinant fusion proteins linking two or more different single-chain antibody or antibody fragment segments with the needed dual specificities. (See, e.g., Coloma et al., Nature Biotech. 15:159-163, (1997)). A variety of bispecific antibodies can be produced using molecular engineering. In one form, the bispecific antibody may consist of, for example, an scFv with a single binding site for one antigen and a Fab fragment with a single binding site for a second antigen. In another form, the bispecific antibody may consist of, for example, an IgG with two binding sites for one antigen and two scFv with two binding sites for a second antigen. In alternative embodiments, multispecific and/or multivalent antibodies may be produced as DOCK-AND-LOCK™ (DNL™) complexes as described below. Extensive cross-linking of CD22 may be induced, for example, by administration of bispecific or multispecific antibodies with multiple binding sites for CD22.

In certain embodiments, the anti-CD22 antibody may be administered to a patient as part of a combination of antibodies. Bispecific antibodies are preferred to administration of combinations of separate antibodies, due to cost and convenience. However, where combinations of separate antibodies provide improved safety or efficacy, the combination may be utilized. The antibodies may bind to different epitopes of the same antigen or to different antigens. Preferably, the antigens are selected from the group consisting of BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, CD56, CCD57, CD59, CD64, CD71, CD79a, CD79b, CD117, CD138, FMC-7 and HLA-DR. However, antibodies against other antigens of use for therapy of cancer, autoimmune diseases or immune dysfunction diseases are known in the art, as discussed below, and antibodies against any such disease-associated antigen known in the art may be utilized.

Dock-and-Lock™ (DNL™)

In preferred embodiments, a bivalent or multivalent antibody is formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα or RIIβ (Newlon et al., Nat. Struct. Biol. 1999; 6:222). As discussed below, similar portions of the amino acid sequences of other regulatory subunits are involved in dimerization and docking, each located at or near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265;21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527, 787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL™ constructs, different AD or DDD sequences may be utilized. Exemplary DDD and AD sequences are provided below.

DDD1

(SEQ ID NO: 9)
SHIQIPPGLTELLQGYTVEVLRQQPPDLVEFAVEYFTRLREARA

-continued

```
DDD2
                                     (SEQ ID NO: 10)
CGHIQIPPGLTELLQGYTVEVLRQQPPDLVEFAVEYFTRLREARA

AD1
                                     (SEQ ID NO: 11)
QIEYLAKQIVDNAIQQA

AD2
                                     (SEQ ID NO: 12)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                     (SEQ ID NO: 13)
SLRECELYVQKHNIQALLKDSIVQLCTARPERPMAFLREYFERLEKEEAK

DDD3C
                                     (SEQ ID NO: 14)
MSCGGSLRECELYVQKHNIQALLKDSIVQLCTARPERPMAFLREYFERLE

KEEAK

AD3
                                     (SEQ ID NO: 15)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                     (SEQ ID NO: 16)
SLRECELYVQKHNIQALLKDVSIVQLCTARPERPMAFLREYFEKLEKEEAK

PKA RIβ
                                     (SEQ ID NO: 17)
SLKGCELYVQLHGIQQVLKDCIVHLCISKPERPMKFLREHFEKLEKEENRQ

ILA

PKA RIIα
                                     (SEQ ID NO: 18)
SHIQIPPGLTELLQGYTVEVGQQPPDLVDFAVEYFTRLREARRQ

PKA RIIβ
                                     (SEQ ID NO: 19)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256, 395; Stickney et al., Cancer Res. 51:6650, 1991; Yuan et al., Cancer Res. 51:3119, 1991; U.S. Pat. Nos. 6,077,499; 7,011, 812; 7,300,644; 7,074,405; 6,962,702; 7,387,772; 7,052, 872; 7,138,103; 6,090,381; 6,472,511; 6,962,702; and 6,962, 702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-$NH_2$ (SEQ ID NO:20), wherein DOTA is 1,4,7,10-tetraazacyclododecane1,4,7,10-tetraacetic acid and HSG is the histamine succinyl glycyl group. Alternatively, DOTA may be replaced by NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Preparation of Immunoconjugates

In some embodiments, a therapeutic or diagnostic agent may be covalently attached to an anti-CD22 antibody or antibody fragment to form an immunoconjugate. Where the immunoconjugate is to be administered in concentrated form by subcutaneous, intramuscular or transdermal delivery, the skilled artisan will realize that only non-cytotoxic agents may be conjugated to the antibody. Where a second antibody or fragment thereof is administered by a different route, such as intravenously, either before, simultaneously with or after the subcutaneous, intramuscular or transdermal delivery, then the type of diagnostic or therapeutic agent that may be conjugated to the second antibody or fragment thereof is not so limited, and may comprise any diagnostic or therapeutic agent known in the art, including cytotoxic agents.

In some embodiments, a diagnostic and/or therapeutic agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.). For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.).

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.). Examples of such substituted cyclooctynes include difluorinated cyclooctynes, 4-dibenzocyclooctynol and azacyclooctyne (Id.). An alternative copper-free reaction involved strain-promoted alkyne-nitrone cycloaddition to give N-alkylated isoxazolines (Id.). The reaction was reported to have exceptionally fast reaction kinetics and was used in a one-pot three-step protocol for site-specific modification of peptides and proteins (Id.). Nitrones were prepared by the condensation of appropriate aldehydes with N-methylhydroxylamine and the cycloaddition reaction took place in a mixture of acetonitrile and water (Id.). These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetyl-mannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.). Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.). The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.). The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vκ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Therapeutic and Diagnostic Agents

In certain embodiments, the anti-CD22 antibodies or fragments thereof may be used in combination with one or more therapeutic and/or diagnostic agents. Therapeutic agents may be selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a tyrosine kinase inhibitor, a Bruton kinase inhibitor, a sphingosine inhibitor, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents, and combinations thereof.

Exemplary drugs may include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), a prodrug form of 2-pyrrolinodoxorubicine (P2PDox), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Immunomodulators may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -λ or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, -λ and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, kit-ligand or FLT-3, angiostatin, thrombospondin, endostatin, tumor necrosis factor and lymphotoxin.

Chemokines of use include RANTES, MCAF, MIP1-alpha, MIP1-Beta and IP-10.

Radioactive isotopes include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Fm-255 and Th-227. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb and the like.

A variety of tyrosine kinase inhibitors are known in the art and any such known therapeutic agent may be utilized. Exemplary tyrosine kinase inhibitors include, but are not limited to canertinib, dasatinib, erlotinib, gefitinib, imatinib, lapatinib, leflunomide, nilotinib, pazopanib, semaxinib, sorafenib, sunitinib, sutent and vatalanib. A specific class of tyrosine kinase inhibitor is the Bruton tyrosine kinase inhibitor. Bruton tyrosine kinase (Btk) has a well-defined role in B-cell development. Bruton kinase inhibitors include, but are not limited to, PCI-32765 (ibrutinib), PCI-45292, GDC-0834, LFM-A13 and RN486.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (P1GF) peptides and antibodies, anti-vascular growth factor antibodies (such as anti-VEGF and anti-P1GF), anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, interferon-lambda, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

The therapeutic agent may comprise an oligonucleotide, such as a siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bc12 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Administration

The subject antibodies and immunoglobulins in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active ingredients (i.e., the labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection, more preferably by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising antibodies can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The formulation thereof should be in a solution having a suitable pharmaceutically acceptable buffer such as phosphate, TRIS (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

The dosage of an administered antibody for humans will vary depending upon such factors as the patient's age, weight, height, sex, general medical condition and previous medical history. Typically, it is desirable to provide the recipient with a dosage of antibody that is in the range of from about 1 mg to 600 mg as a single infusion or single or multiple injections, although a lower or higher dosage also may be administered. Typically, it is desirable to provide the recipient with a dosage that is in the range of from about 50 mg per square meter ($m^2$) of body surface area or 70 to 85 mg of the antibody for the typical adult, although a lower or higher dosage also may be administered. Examples of dosages of antibodies that may be administered to a human subject are 1 to 1,000 mg, more preferably 1 to 70 mg, most preferably 1 to 20 mg, although higher or lower doses may be used. Dosages may be repeated as needed, for example, once per week for 4-10 weeks, preferably once per week for 8 weeks, and more preferably, once per week for 4 weeks. It may also be given less frequently, such as every other week for several months, or more frequently, such as twice weekly or by continuous infusion.

More recently, subcutaneous administration of veltuzumab has been given to NHL patients in 4 doses of 80, 160 or 320 mg, repeated every two weeks (Negrea et al., 2011, Haematologica 96:567-73). Only occasional, mild to moderate and transient injection reactions were observed, with no other safety issues (Id.). The objective response rate (CR+CRu+PR) was 47%, with a CR/CRu (complete response) rate of 24% (Id.). Interestingly, the 80 mg dosage group showed the highest percentage of objective response (⅔, 67%), with one of three patients showing a complete response (Id.). Four out of eight objective responses continued for 60 weeks (Id.). All serum samples evaluated for HAHA were negative (Id.). Although the low sample population reported in this study precludes any definitive conclusions on optimal dosing, it is apparent that therapeutic response was observed at the lowest dosage tested (80 mg).

In certain alternative embodiments, the antibody may be administered by transdermal delivery. Different methods of transdermal delivery are known in the art, such as by transdermal patches or by microneedle devices, and any such known method may be utilized. In an exemplary embodiment, transdermal delivery may utilize a delivery device such as the 3M hollow Microstructured Transdermal System (hMTS) for antibody based therapeutics. The hMTS device comprises a 1 $cm^2$ microneedle array consisting of 18 hollow microneedles that are 950 microns in length, which penetrate approximately 600-700 microns into the dermal layer of the skin where there is a high density of lymphatic channels. A spring-loaded device forces the antibody composition from a fluid reservoir through the microneedles for delivery to the subject. Only transient erythema and edema at the injection site are observed (Burton et al., 2011, Pharm Res 28:31-40). The hMTS device is not perceived as a needle injector, resulting in improved patient compliance.

In preferred embodiments where the antibody is administered subcutaneously, intramuscularly or transdermally in a concentrated formulation, the volume of administration is preferably limited to 3 ml or less, more preferably 2 ml or less, more preferably 1 ml or less. The use of concentrated antibody formulations allowing low volume subcutaneous, intramuscular or transdermal administration is preferred to the use of more dilute antibody formulations that require specialized devices and ingredients (e.g., hyaluronidase) for subcutaneous administration of larger volumes of fluid, such as 10 ml or more. The subcutaneous, intramuscular or transdermal delivery may be administered as a single administration to one skin site or alternatively may be repeated one or more times, or even given to more than one skin site in one therapeutic dosing session. However, the more concentrated the formulation, the lower the volume injected and the fewer injections will be needed for each therapeutic dosing.

Methods of Use

In preferred embodiments, the anti-CD22 antibodies are of use for therapy of cancer. Examples of cancers include, but are not limited to, carcinoma, lymphoma, blastoma, glioma, melanoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, neuroblastoma, cervical cancer, ovarian cancer, liver cancer, bladder cancer, hepatoma, breast cancer, colon cancer, rectal cancer, endometrial cancer or uterine carcinoma, salivary gland carcinoma, kidney or renal cancer, prostate cancer, vulval cancer, thyroid cancer, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: acute childhood lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalamic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lymphoproliferative disorders, macroglobulinemia, male breast cancer, malignant mesothelioma, malignant thymoma, medulloblastoma, melanoma, mesothelioma, metastatic occult primary squamous neck cancer, metastatic primary squamous neck cancer, metastatic squamous neck cancer, multiple myeloma, multiple myeloma/plasma cell neoplasm, myelodysplastic syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatic squamous neck cancer, oropharyngeal cancer, osteo-/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcomas, salivary gland cancer, sarcoidosis sarcomas, Sezary syndrome, skin cancer, small cell lung cancer, small intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethral cancer, uterine cancer, uterine sarcoma, vaginal cancer, visual pathway and hypothalamic glioma, vulvar cancer, Waldenstrom's macroglobulinemia, Wilms' tumor, and any other hyperproliferative disease, besides neoplasia, located in an organ system listed above.

The methods and compositions described and claimed herein may be used to detect or treat malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected and/or treated include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

The exemplary conditions listed above that may be treated are not limiting. The skilled artisan will be aware that antibodies or antibody fragments are known for a wide variety of conditions, such as autoimmune disease, graft-versus-host-disease, organ transplant rejection, cardiovascular disease, neurodegenerative disease, metabolic disease, cancer, infectious disease and hyperproliferative disease.

Exemplary autoimmune diseases include acute idiopathic thrombocytopenic purpura, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, juvenile diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

Kits

Various embodiments may concern kits containing components suitable for treating diseased tissue in a patient. Exemplary kits may contain at least one concentrated antibody or fragment thereof as described herein. A device capable of delivering the kit components by injection, for example, a syringe for subcutaneous injection, may be included. Where transdermal administration is used, a delivery device such as hollow microneedle delivery device may be included in the kit. Exemplary transdermal delivery devices are known in the art, such as 3M's hollow Microstructured Transdermal System (hMTS), and any such known device may be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Alternatively, the concentrated antibody may be delivered and stored as a liquid formulation. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

Crosslinking of CD22 by Anti-CD22 Antibody Triggers BCR Signaling and Caspase-Dependent Apoptosis in Hematopoietic Cancer Cells The anti-CD22 antibody epratuzumab has demonstrated therapeutic activity in patients with non-Hodgkin lymphoma, acute lymphoblastic leukemia, systemic lupus erythematosus, and Sjögren's syndrome, but its mechanism of affecting normal and malignant B cells remains incompletely understood. We reported previously that epratuzumab displayed in vitro cytotoxicity to CD22-expressing Burkitt lymphoma cell lines (Daudi and Ramos) only when immobilized on plates or combined with a crosslinking antibody plus a suboptimal amount of anti-IgM (1 μg/mL). Herein, we show that, in the absence of additional anti-IgM ligation, extensive crosslinking of CD22 by plate-immobilized epratuzumab induced intracellular changes in Daudi cells similar to ligating B-cell antigen receptor (BCR) with a sufficiently high amount of anti-IgM (10 μg/mL).

Specifically, either treatment led to phosphorylation of CD22, CD79a and CD79b, along with their translocation to lipid rafts, both of which were essential for effecting caspase-dependent apoptosis. Moreover, such immobilization induced stabilization of F-actin, phosphorylation of Lyn, ERKs and JNKs, generation of reactive oxygen species (ROS), decrease in mitochondria membrane potential ($\Delta\psi_m$), upregulation of pro-apoptotic Bax, and downregulation of anti-apoptotic Bcl-xl and Mcl-1. The physiological relevance of immobilized epratuzumab was implicated by noting that several of its in vitro effects, including apoptosis, drop in $\Delta\psi_m$, and generation of ROS, could be observed with soluble epratuzumab in Daudi cells co-cultivated with human umbilical vein endothelial cells. These results suggest that the in vivo mechanism of non-ligand-blocking epratuzumab may, in part, involve the unmasking of CD22 to facilitate the trans-interaction of B cells with vascular endothelium.

In the studies disclosed below, we further explored the molecular events associated with the cytotoxicity of epratuzumab in vitro, examining epratuzumab presented in soluble or immobilized form in various combinations, as summarized in Table 2. We showed in Daudi and D1-1 cells that epratuzumab by non-covalent adsorption on microtiter plates (the Dried-I format, Table 2) induces phosphorylation of CD22, CD79a and CD79b, as well as their translocation to lipid rafts, which are instrumental for cell death via caspase-dependent apoptosis. Such plate-immobilized epratuzumab likewise induced substantial apoptosis and growth inhibition in Ramos cells. Treatment of D1-1 cells with the Dried-I format also revealed multiple intracellular changes that included sustained phosphorylation of ERK and JNK MAP kinases, decrease in $\Delta\psi_m$, generation of ROS, activation of caspases, as well as upregulation and down-regulation of pro- and anti-apoptotic proteins, respectively. Interestingly, several of the in vitro effects observed with the Dried-I format, including apoptosis, drop in $\Delta\psi_m$, and generation of ROS, could be observed with the Dried-II format (Table 2) comprising co-cultivation of Daudi cells over a monolayer of human umbilical vein endothelial cells (HUV-EC) in the presence of soluble epratuzumab (20 μg/mL). These findings indicate a physiological relevance of immobilized epratuzumab, and suggest that the in vivo mechanism of non-ligand-blocking epratuzumab may, in part, involve the unmasking of CD22 to facilitate the trans-interaction of B cells with vascular endothelium.

Abbreviations used herein include: Anti-IgM, F(ab')$_2$ fragment of affinity-purified goat anti-human IgM, Fc$_{5\mu}$ fragment; BCR, B-cell antigen receptor; BSA, bovine serum albumin; CM-H$_2$DCF-DA, 2',7'-dichlorodihydrofluorescein diacetate; $\Delta\psi_m$, mitochondria membrane potential; DNP, 2,4-dinitrophenyl; EC, endothelial cells; ERKs, extracellular signal-regulated kinases; FBS, fetal bovine serum; FITC-DNase I, fluorescein isothiocyanate-conjugated DNase I; 488-annexin V, Alexa Fluor 488-conjugated annexin V; GAH, F(ab')$_2$ fragment of affinity-purified goat anti-human IgG Fcγ fragment-specific; HUV-EC, human umbilical vein endothelial cells; ITIM, immunoreceptor tyrosine-based inhibition motif; JNKs, c-Jun N-terminal kinases; JP, jasplakinolide; LatB, latrunculin B; Lyn, Lck/Yes novel tyrosine kinase; MAP kinases, mitogen-activated protein kinases; mIgM, membrane IgM; MTS, (3-(4,5-dimethylthiazol-2-yl)-5-(3-carboxymethoxyphenyl)-2-(4-sulfophenyl)-2H-tetrazolium; PARP, poly ADP ribose polymerase; PBS, phosphate-buffered saline; PLCγ2, phospholipase C, isotype gamma 2; Rhodamine-anti-IgG, rhodamine-conjugated F(ab')$_2$ fragment of affinity-purified goat anti-human IgG, F(ab')$_2$ fragment-specific; ROS, reactive oxygen species; 7-AAD, 7-aminoactinomycin D; Syk, spleen tyrosine kinase; TMRE, tetramethylrhodamine, ethyl ester Materials and Methods Cell lines, antibodies, and reagents. All cell lines, except D1-1 (a subclone of Daudi with a higher expression of BCR than D-1-7), were obtained from the American Type Culture Collection (Manassas, Va.) and have been authenticated by Promega (Madison, Wis.) using Short Tandem Repeat (STR) analysis. Phospho-specific antibodies for ERK, JNK, PLCγ2, and Lyn were obtained from Cell Signaling (Danvers, Mass.), as were antibodies specific for β-actin, Bcl-xL, Mcl-1, Caspase-3, Caspase-9, and PARP. The sources of other antibodies were as follows: Santa Cruz Biotech (Santa Cruz, Calif.) for CD22, CD79a, CD79b, Bcl-2, and Bax; Millipore (Billerica, Mass.) for anti-tyrosine (4G10); and Jackson ImmunoResearch (West Grove, Pa.) for F(ab')$_2$ fragment of affinity purified goat anti-human IgM, Fc$_{5\mu}$ (anti-IgM), F(ab')$_2$ fragment of affinity purified goat anti-human IgG Fcγ fragment-specific (GAH), and rhodamine-conjugated F(ab')$_2$ fragment of affinity-purified goat anti-human IgG, F(ab')$_2$ fragment-specific (rhodamine-anti-IgG). The anti-CEACAM5 antibody, labetuzumab (hMN-14), was supplied by Immunomedics and served as an isotype control. Cell culture media and supplements, fluorescein isothiocyanate-conjugated DNase I (FITC-DNase I), Alexa Fluor 488 conjugated annexin V (488-annexin V), tetramethylrhodamine/ethyl ester (TMRE), and 2',7'-dichlorodihydrofluorescein diacetate (CM-H$_2$DCF-DA), were supplied by Invitrogen (Grand Island, N.Y.). Rhodamin phalloidin was obtained from Cytoskeleton, Inc. (Denver, Colo.). One Solution Cell Proliferation assay reagent was obtained from Promega (Madison, Wis.). Phosphosafe and RIPA buffers were procured from EMD chemicals (Billerica, Mass.). Latrunculin B (LatB), Jasplakinolide (JP), and all other chemicals were obtained from Sigma-Aldrich (St. Louis, Mo.).

Immobilization of epratuzumab. To prepare the Dried-I format, epratuzumab in the form of IgG or F(ab')$_2$ at the indicated concentrations in bicarbonate buffer (50 mM; pH 9.6) was added to non-tissue-culture flat-bottom or U-bottom plates as specified, and incubated at 4° C. overnight, followed by washing with 2×RPMI-1640 medium containing 5% fetal bovine serum (FBS) on the next day before use. Control antibodies were immobilized in the same fashion. To prepare the Dried-II format, 2 mL of HUV-EC-C cells (1.5×10$^4$/mL) were added to 6-well, tissue-culture-treated flat-bottom plates, incubated overnight, and washed before use. To prepare the Particulate-I format, epratuzumab (50 µg) was conjugated to 200 µL of carboxyl polystyrene particles (3.0 to 3.4 µm, 5% w/v; Spherotech, Lake Forest, Ill.) in 1 mL of 2-(N-morpholino)ethanesulfonic acid buffer containing 20 mg of 1-ethyl-3-(3-dimethylaminopropyl) carbodiimide for 30 min according to the manufacturer's protocol. Conjugated particles were washed 3× with PBS and reconstituted with 200 µL of PBS containing 0.05% bovine serum albumin (BSA) for use as the stock solution.

To prepare the Particulate-II format, FAST FLOW Immobilized rProtein A (40 to 165 µm; Repligen, Waltham, Mass.) was incubated with 100 µL of epratuzumab (1 mg/mL) and supernatants were analyzed to estimate the amounts of epratuzumab noncovalently linked to the SEPHAROSE® beads. The resulting epratuzumab-bound beads were washed 3× with phosphate-buffered saline (PBS) and reconstituted in 100 µL of the RPMI-1640 medium.

Cell culture and cytotoxicity assay. Cell lines were cultured in RPMI-1640 medium supplemented with 10% heat-inactivated FBS, L-glutamine (2 mM), penicillin (200 U/mL), and streptomycin (100 µg/mL) in a humidified incubator at 37° C. with 5% CO$_2$. To evaluate the functional activity of epratuzumab in the Dried-I format, different amounts of IgG (starting from 20 µg/mL with 5-fold serial dilution to 0.01 ng/mL) were immobilized in non-tissue-culture-treated, U-bottom, 96-well plates overnight. Daudi cells (1×10$^4$ cells per well) were seeded and incubated for 3 days. For D1-1 and Ramos cells, IgG or F(ab')$_2$ of epratuzumab at 5, 10, and 20 µg/mL was immobilized in 48-well plates overnight. After washing, cells were seeded (1×10$^4$ cells per well) and incubated for 4 days. The number of viable cells was then determined using the MTS assay per the manufacturer's protocol, and plotted as percent of the untreated. Activity of soluble epratuzumab and anti-IgM also was evaluated in parallel.

Annexin V binding assay. Cells in 6-well plates (2×10$^5$ cells/well) were treated for 24 or 48 h with epratuzumab immobilized to polystyrene beads (Particulate-I) or plates (Dried-I), washed, resuspended in 100 µL of annexin-binding buffer, stained with 5 µL of 488-annexin V and 0.5 µL of 7-aminoactinomycin D (7-AAD) for 20 min, added 400 µL of annexin-binding buffer, and analyzed by flow cytometry (FACSCALIBUR™; Becton Dickinson, San Jose, Calif.). Alternatively, cells were resuspended in 100 µL of annexin-binding buffer, stained with 5 µL of 488-annexin V for 20 min, added 400 µL of annexin-binding buffer containing 7-AAD, and analyzed. When required, cells were pretreated with the indicated inhibitors for 2 h before adding the test article.

Immunoblot analysis. Daudi, D1-1 or Ramos cells (2×10$^7$ cells) were added to plates coated with epratuzumab (10 µg/mL) and incubated for the indicated times. Cells were washed with PBS, lysed in ice-cold PHOSPHOSAFE™ buffer, and the lysates clarified by centrifugation at 13,000× g. Protein samples (25 µg/lane) were resolved by SDS-PAGE on 4-20% gradient tris-glycine gels, followed by transfer onto nitrocellulose membranes, and probed with appropriate antibodies.

Immunoprecipitation. D1-1 cells (5×10$^6$ cell/well) in 6-well plates were incubated with test articles for the indicated times. After lysing the cells in ice-cold RIPA buffer, immunoprecipitation was performed using phospho-tyrosine antibody (4G10; 1:200 dilution). Samples (20 µL) were separated by SDS-PAGE and transferred onto a nitro-cellulose membrane, followed by probing with the indicated antibodies.

Isolation of lipid rafts. Lipid rafts were prepared as described previously (Sieger et al., 2013, Arthritis Rheum 65:770-79). Briefly, cells (5×10$^7$) were untreated or treated for 2 h with various test articles and lysed in 1 mL of cell lysis buffer (Cell Signaling, Danvers, Mass.) containing 1% Triton and 1% protease inhibitor cocktail on ice for 30 min. The lysates were transferred to ultracentrifuge tubes, mixed with 1 mL of 80% sucrose in lysis buffer, overlaid with 5 mL of 35% sucrose and 4.5 mL of 5% sucrose, then centrifuged at 50,000 rpm (200,000×g) for 3 h at 4° C. Fractions of 1 mL were collected from the top, the protein concentration of each fraction determined with the Bio-Rad protein assay kit, and 20 μg sample of each fraction was resolved by 12-20% SDS-PAGE, followed by immunoblots with appropriate antibodies.

Measurement of $\Delta\psi_m$ and ROS. Daudi or D1-1 cells ($2\times10^5$ cells/well) were incubated for 48 h with test articles as indicated), washed, stained with either TMRE (50 nM) or CM-$H_2$DCF-DA (1 μM) for 30 min in the dark at 37° C., washed 3× with PBS, and analyzed by flow cytometry for $\Delta\psi_m$ or ROS, respectively, as described previously (Gupta et al., 2010, Blood 116:3258-67).

Immunofluorescence microscopy. Daudi cells ($2\times10^6$ per sample), were pretreated with test articles as indicated at 37° C. for 1 h, incubated with or without LatB for 5 min, washed, fixed, permeabilized with 4% formalin and 0.1% Triton-100, and stained with Rhodamin-phalloidin and FITC-DNase I for 30 min in the dark at room temperature. Cells were then washed, resuspended in mounting solution containing DAPI, and examined by fluorescent microscopy.

Calcium mobilization assay. Daudi cells were loaded with Fluo-3 AM and Fura Red AM dye for 30 min at room temperature in the dark. For measurement of intracellular calcium flux, cells were washed 2× with an assay buffer comprising HBSS (1.25 mM $CaCl_2$, 10 mM HEPES, 1% BSA), and resuspended in the same buffer, from which 1 mL ($2\times10^6$ cells) was dispensed into each vial and incubated with a test antibody (20 μg/mL) or the Dried-I format of immobilized epratuzumab (20 μg/mL) as indicated, for 1 h at 37° C. All samples were kept on ice until analysis. Baseline fluorescence from each sample was monitored for 1 min before stimulating with anti-IgM (25 μg/mL), and the signal collected for the next 8 min. To monitor calcium influx, cells were washed with HBSS buffer (no $Ca^{2+}$, 10 mM HEPES, 1% BSA, 1.5 mM EGTA), baseline was recorded for 1 min before stimulating with anti-IgM (25 μg/mL). After 4 min, 5 mM $CaCl_2$ was added to the sample and the signal continuously monitored for another 6 min. The ratio of the geometric mean fluorescence intensity of fluo-3 (Em 530/30 nm) to Fura Red (Em 610/20 nm) was plotted against time and analyzed by Flowjo software.

Statistical analysis. Data obtained from in vitro studies were plotted using Prism software (version 4.03). Comparisons of mean values between two treatments were determined by Student's t-test, assuming a normal distribution for the data. A two-tailed t-test was used when comparing different samples. $P<0.05$ was considered statistically significant.

Results

Figure 1B:
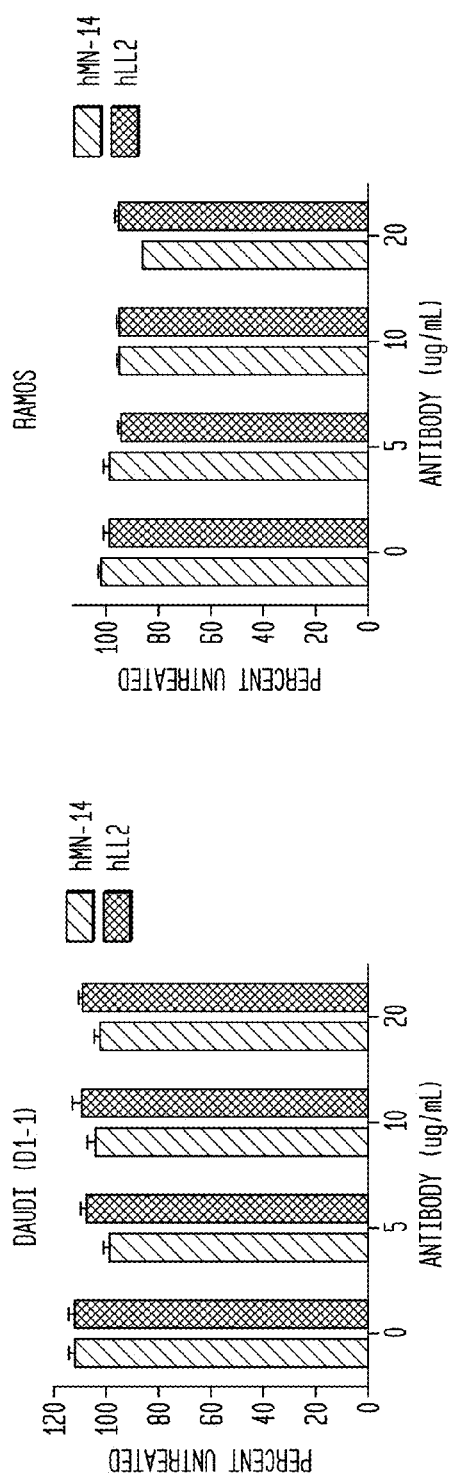
FIG. 1B. Evaluation of growth-inhibition and apoptosis in D1-1 and Ramos cells. Cell viability determined by the MTS assay after 4-day incubation for the Wet-I format of epratuzumab (hLL2) or labetuzumab (hMN-14). Error bars represent standard deviation (SD), where n=3. Significant differences compared to untreated or nonspecific antibody are indicated with ˆ (P<0.005) and # (P<0.05).

Inhibition of proliferation and induction of apoptosis. To evaluate the effect on cell proliferation, varying amounts of epratuzumab were coated on non-tissue-culture, U-bottom plates, and the results of the MTS cell viability assay indicate that at 5 μg/mL, immobilized epratuzumab of the Dried-I format could inhibit about 60% proliferation of D1-1 cells compared to untreated cells ($P<0.005$), with little change found at higher concentrations of 10 and 20 μg/mL (FIG. 1A). In Ramos cells, which express a lower level of CD22 than D1-1, epratuzumab achieved about 45% growth-inhibition when coated at 10 μg/mL compared to untreated cells ($P<0.005$). Immobilized labetuzumab (anti-CEACAM5), serving as an isotype control of the Dried-I format, did not induce appreciable growth-inhibition in either cell line (FIG. 1A). Soluble epratuzumab (the Wet-I format), even at the highest concentration (20 μg/mL) tested, did not induce growth-inhibition in both cell lines (FIG. 1B), indicating the requirement for immobilization.

Evidence that immobilization of epratuzumab was required to induce apoptosis was provided by the Particulate-I format (Table 2) of bead-conjugated epratuzumab (FIG. 1C), which, at both 5- and 20-μL doses, caused about 75% apoptosis in D1-1 cells following a 24-h incubation, as compared to approximately 20% ($P<0.005$) for the three controls (cells with no treatment, cells treated with soluble epratuzumab, and cells treated with unconjugated beads). The same particulate epratuzumab also resulted in about 30% apoptosis in Ramos cells, which was significant ($P<0.005$) compared with the three controls (10% apoptosis). Similar results were obtained with the Dried-I format of epratuzumab F(ab')$_2$ in D1-1 cells, as shown in FIG. 1D for apoptosis (left panel; $P<0.05$ vs. controls) and growth inhibition (right panel; $P<0.025$ vs. controls), indicating a lack of Fc involvement in the cytotoxicity of plate-immobilized epratuzumab.

Figure 2A:
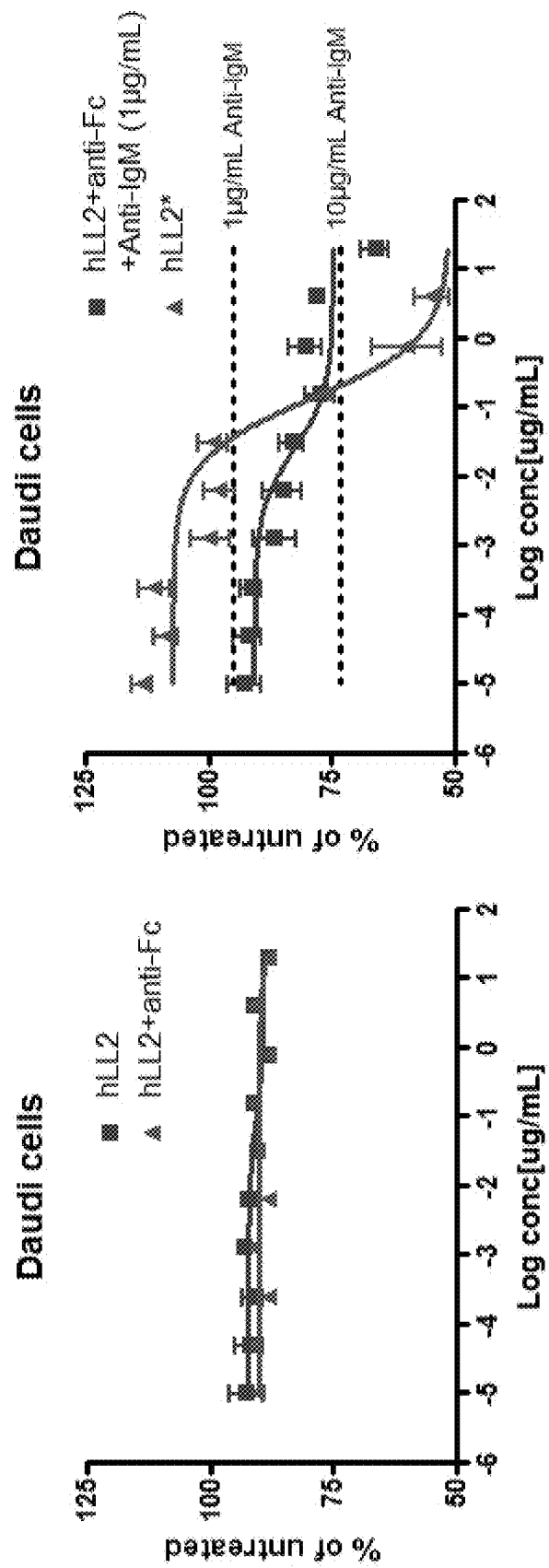
FIG. 2A. Cytotoxicity of epratuzumab in various formats to Daudi cells. Epratuzumab presented as the Dried-I (hLL2*) or Wet-III (hLL2+GAH+anti-IgM) format, right panel, but not the Wet-I (hLL2) or Wet-IIB (hLL2+GAH) format, left panel, induced dose-dependent cytotoxicity in Daudi cells, as measured by the MTS assay.
Figure 2B:
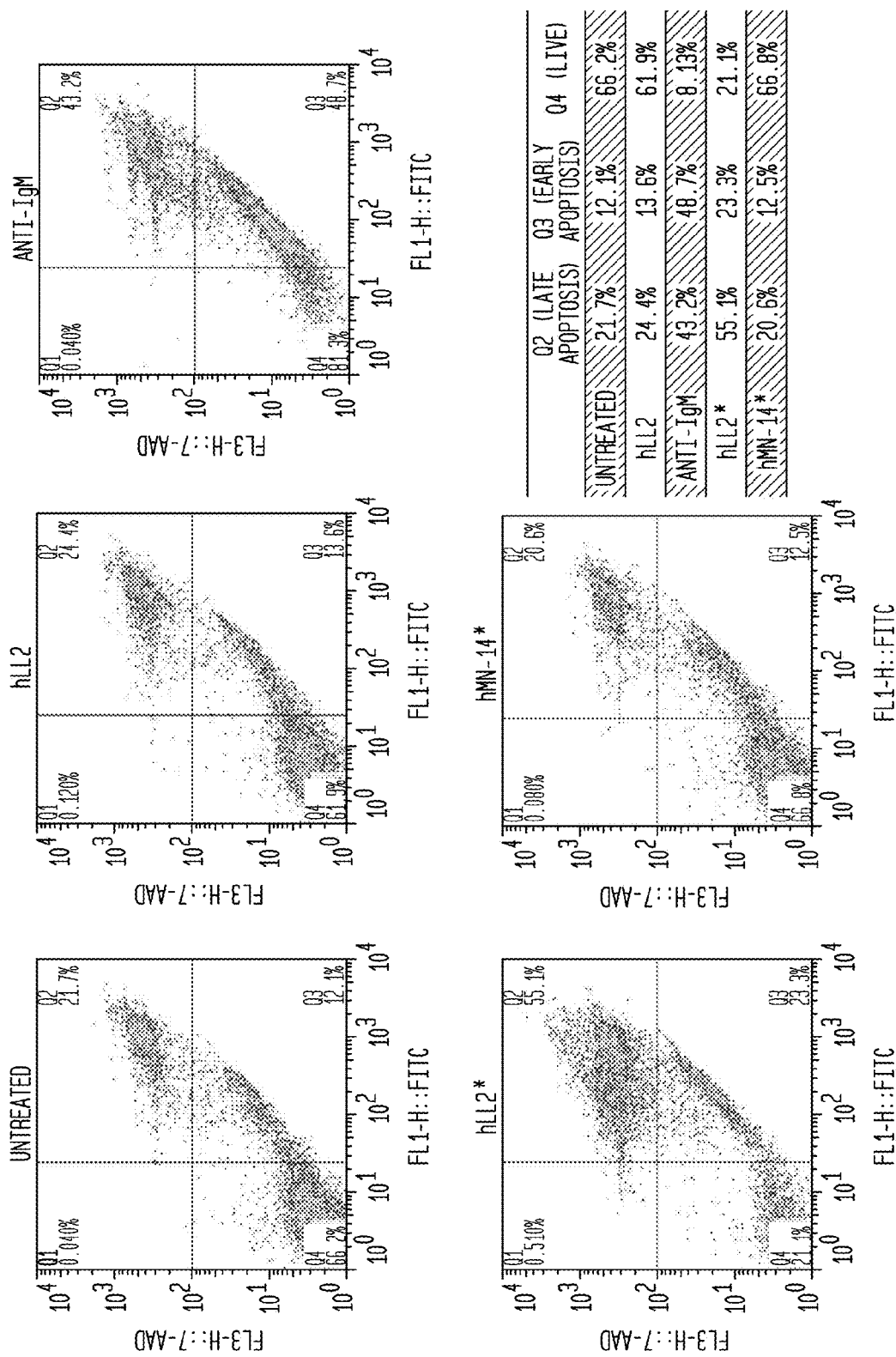
FIG. 2B. Cytotoxicity of epratuzumab in various formats to Daudi cells. The Dried-I format of epratuzumab (hLL2*) induced apoptosis comparable to the positive control of anti-IgM as determined by the Annexin V assay.
Figure 2C:
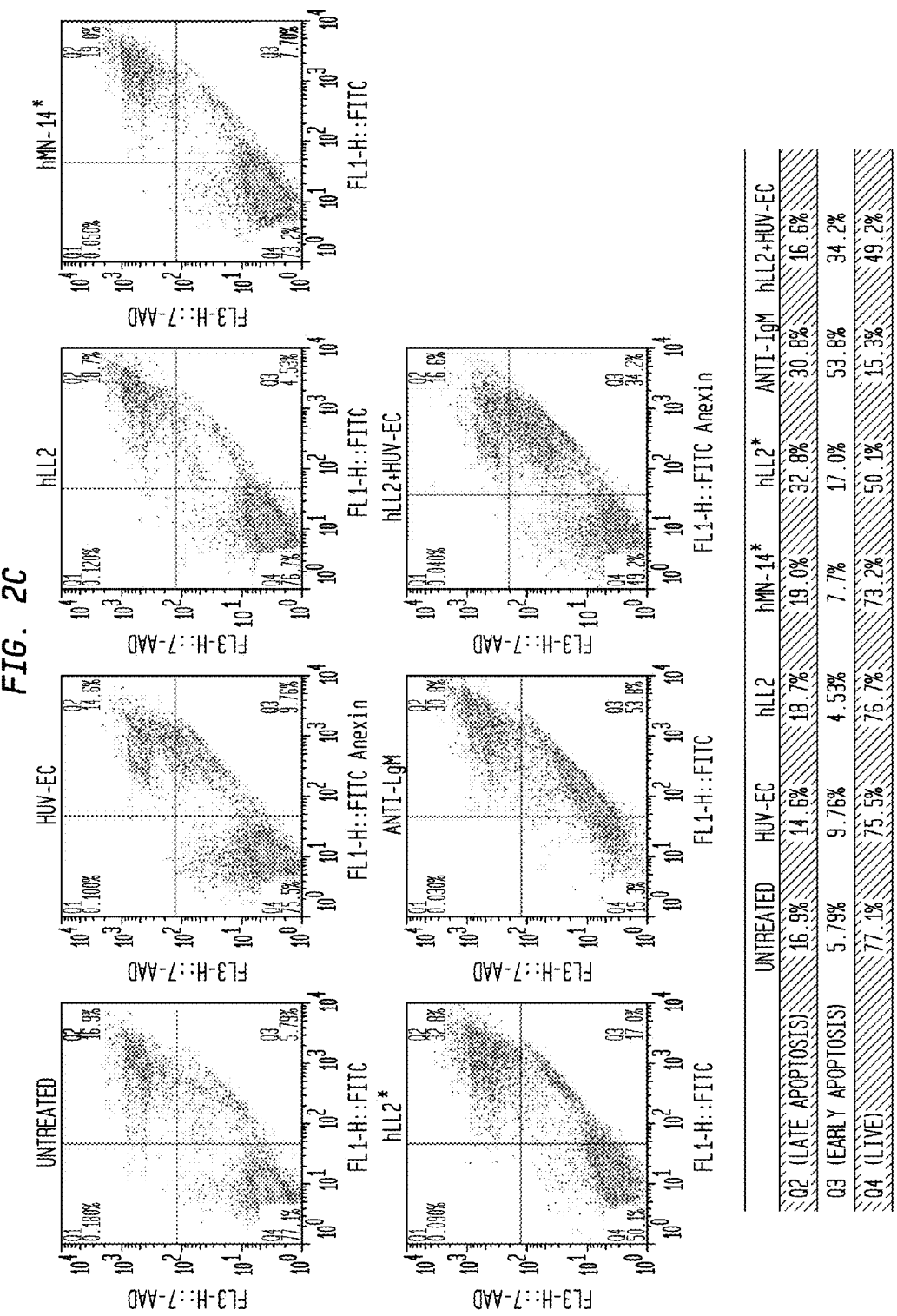
FIG. 2C. Cytotoxicity of epratuzumab in various formats to Daudi cells. The Dried-I format and the Dried-II format, in which soluble epratuzumab was added to a monolayer of HUV-EC, induced apoptosis in Daudi cells to a similar extent (~50%).

Further experiments in Daudi cells demonstrated that the in vitro cytotoxicity of epratuzumab, as determined by the MTS assay, could be observed dose-dependently with the Dried-I or the Wet-III format (FIG. 2A, right panel), but not with the Wet-I or the Wet-IIB format (FIG. 2A, left panel), and confirmed that the Dried-I format induced apoptosis comparable to the positive control of anti-IgM as determined by the Annexin V assay (FIG. 2B). More importantly, we have discovered that the Dried-II format, which employed plates coated with a monolayer of HUV-EC, was capable of inducing apoptosis in Daudi cells in the presence of soluble epratuzumab to a similar extent (~50%), when compared with the Dried-I format (FIG. 2C).

Figure 3A:
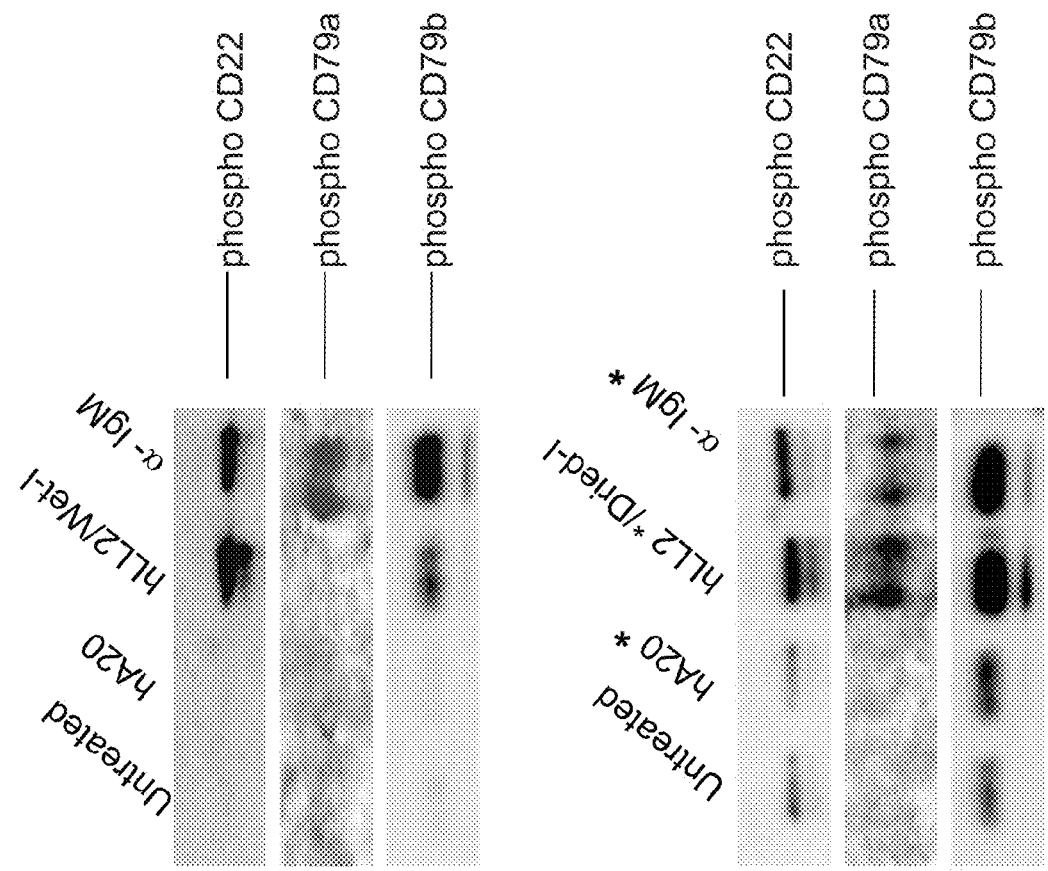
FIG. 3A. Phosphorylation of CD79a, CD79b, CD22 and their translocation into lipid rafts. Western blot analyses of phosphorylated CD79a, CD79b, and CD22 in D1-1 cells treated for 2 h with the Wet-I format of soluble (upper panel) or the Dried-I format of immobilized (lower panel) antibodies, and FIG. 3B. Phosphorylation of CD79a, CD79b, CD22 and their translocation into lipid rafts. Western blot analyses of phosphorylated CD79a, CD79b, and CD22 in D1-1 cells treated for 2 h with various formats of soluble epratuzumab, including Wet-I (lane 4; hLL2, 7.5 µg/mL), Wet-IIA (lane 5; hLL2, 7.5 µg/mL; GAH, 10 µg/mL), and Wet-III (lane 7; hLL2, 7.5 µg/mL; GAH, 10 µg/mL; anti-IgM, 1 µg/mL). In lane 6, the amounts of anti-hFc and anti-IgM were the same as those in lane 7, but hLL2 was too low (10 ng/mL) to induce a notable effect.

Phosphorylation of CD22, CD79a and CD79b. To elucidate the differential effect induced on D1-1 or Ramos cells by soluble (in various Wet-based formats) and immobilized (the Dried-I format) epratuzumab, we evaluated their roles in phosphorylating CD22, CD79a, and CD79b, and compared the results with those of anti-IgM. As shown in FIG. 3A (left panel) for D1-1 cells, soluble anti-IgM at 10 μg/mL induced phosphorylation of CD22, CD79a and CD79b, while soluble epratuzumab (lane: hLL2/Wet-I) induced notable phosphorylation of CD22 and some CD79b, but not CD79a. In contrast, FIG. 3A (right panel) shows immobilized epratuzumab (lane: hLL2*/Dried-I), and immobilized anti-IgM (lane: anti-IgM*) as well, induced phosphorylation of CD22, CD79a and CD79b to a similar extent. However, whereas the Wet-III format of epratuzumab (FIG. 3B, lane 7), comprising a mixture of hLL2 (7.5 μg/mL), GAH (10 μg/mL) and anti-IgM (1 μg/mL), induced the phosphorylation of CD22, CD79a, and CD79b as soluble anti-IgM at 10 μg/mL (FIG. 3B, lane 8), omitting one or two components from the Wet-III format (FIG. 3B, lanes 2-5), or the provision of only a very small amount of hLL2 (10 ng/mL) to GAH and anti-IgM (FIG. 3B, lane 6), failed to induce phosphorylation of all three molecules. These results correlate the observed cytotoxicity of anti-IgM (10 μg/mL) and epratuzumab presented in the Dried-I or Wet-III format with their ability to simultaneously phosphorylate CD22, CD79a, and CD79b in target cells.

Figure 3B:
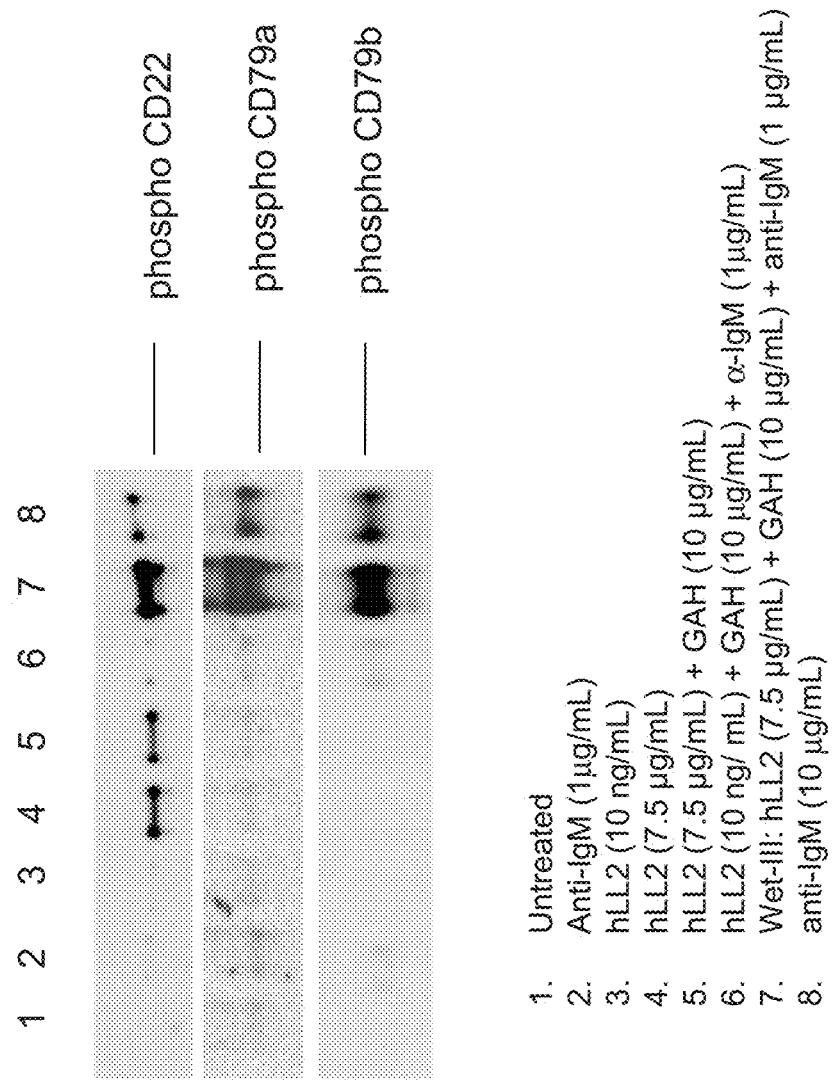
FIG. 3C. Phosphorylation of CD79a, CD79b, CD22 and their translocation into lipid rafts. CD22 was detected in the lipid rafts (fractions 3-6) following treatment of D1-1 cells with anti-IgM (10 µg/mL) and both the Wet-I (hLL2, 20 µg/mL) and Dried-I (hLL2*, 20 µg/mL) formats of epratuzumab; right panel, CD79a was translocated to the lipid rafts (fractions 4-7) by either anti-IgM (10 µg/mL) or the Dried-I format of epratuzumab (hLL2*, 20 µg/mL), but not soluble epratuzumab.
FIG 3D. CD79b was translocated to the lipid rafts (fractions 4-7) by either anti-IgM (10µg/mL) or the Dried-I format of epratuzumab (hLL2*, 20 µg/mL), but not soluble epratuzumab (hLL2).
FIG. 3E. Phosphorylation of CD79a, CD79b, CD22 and their translocation into lipid rafts. Anti-IgM (lane 6) and epratuzumab of the Dried-I (lane 3) or Wet-III (lane 4) format, but not the Wet-I (lane 2) or Wet-IIA (lane 5) format, induced redistribution of CD22, CD79a, and CD79b to the lipid rafts.
Figure 3C:
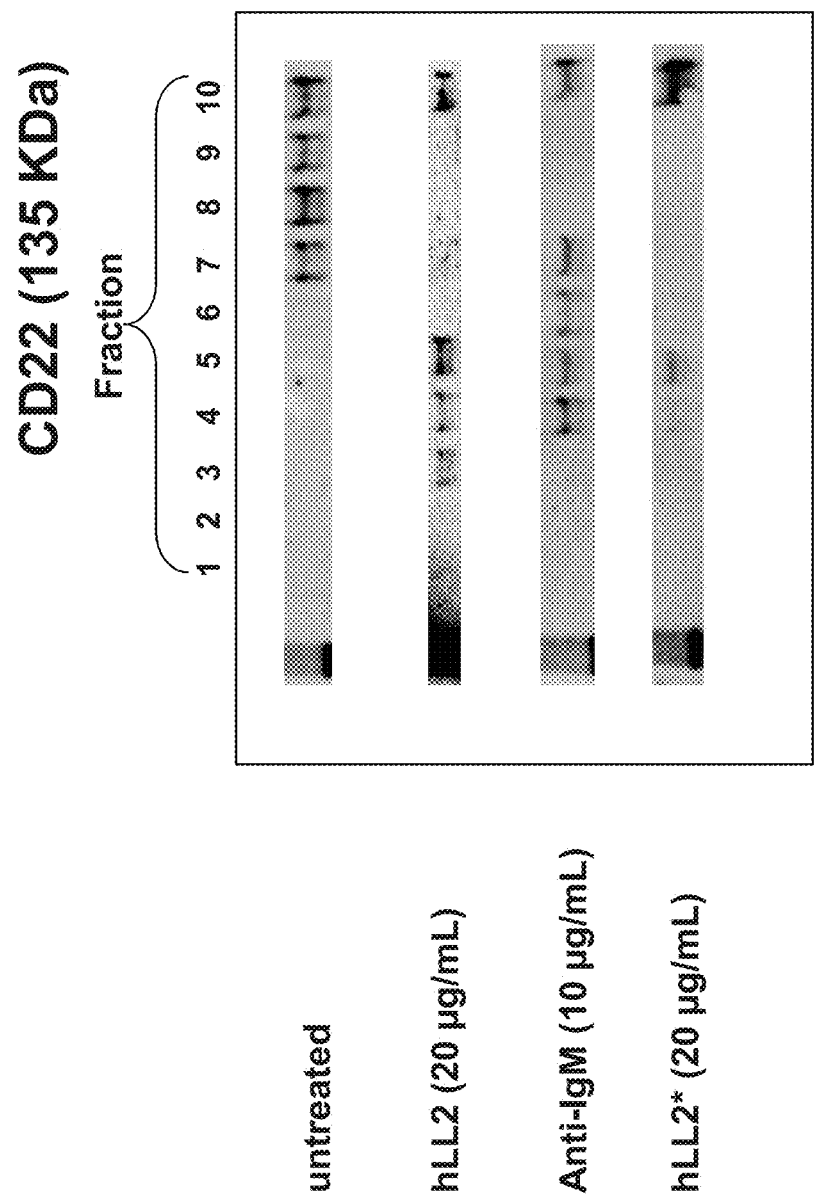
Figure 3D:
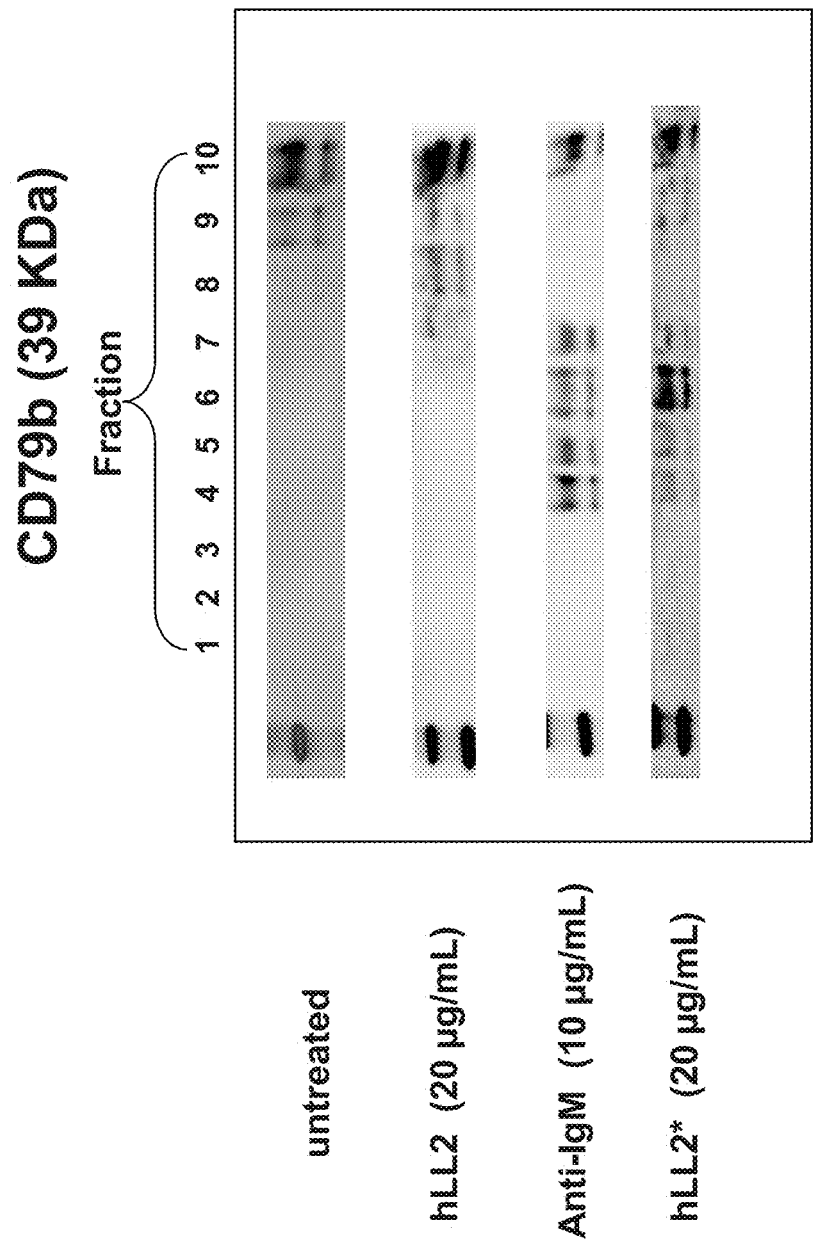
Figure 3E:
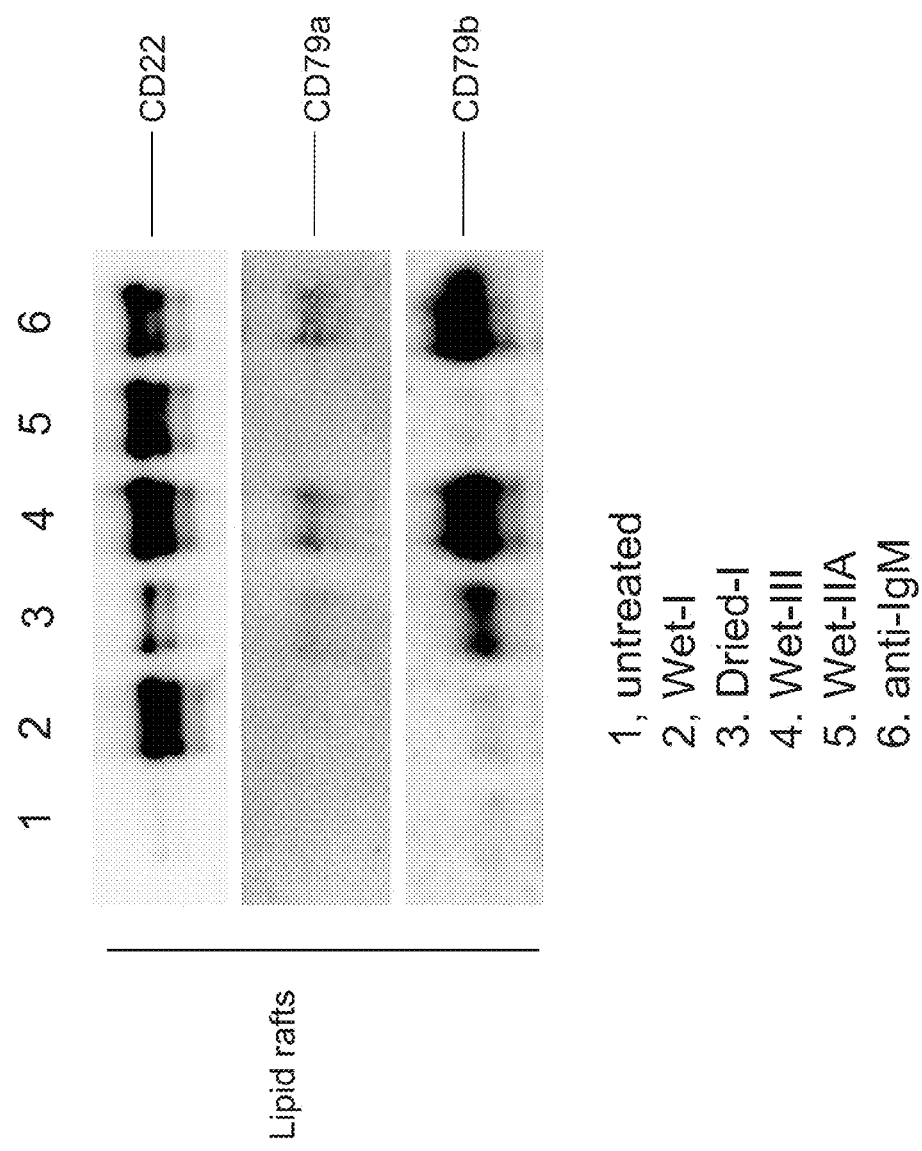
Figure 8:
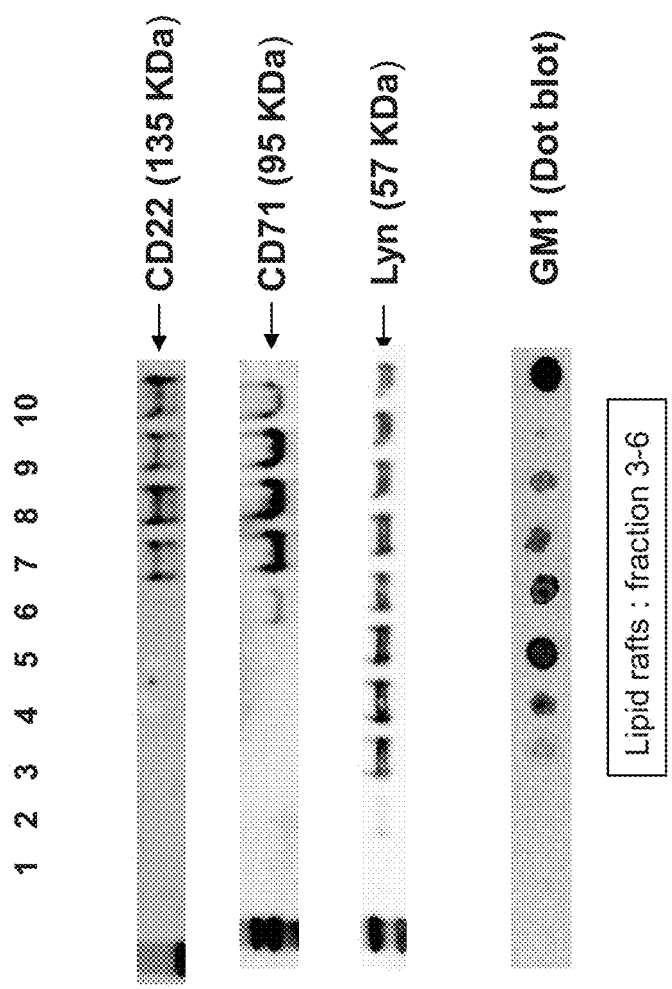
FIG. 8. Location of lipid rafts. Untreated Daudi cells ($5\times10^7$) were lysed in 1 mL of cell lysis buffer (Cell Signaling) containing 1% Triton and 1% protease inhibitor cocktail on ice for 30 min. The lysates were subjected to discontinuous sucrose density gradient ultracentrifugation as described in the Materials and Methods and 1-mL fractions were collected for analysis of CD22, CD71, Lyn, and Ganglioside M1 (GM1), by appropriate antibodies following SDS-PAGE. Fractions of 3-6 were identified as lipid rafts by the dot blot analysis of GM1, a known lipid raft marker. CD71, a non-lipid raft marker, was found in fractions 7 and higher, as was CD22 in the absence of ligation by epratuzumab. The distribution of Lyn to the lipid rafts was also detected.

Translocation of CD22 and CD79 to lipid rafts. Treatment of Daudi cells with anti-IgM (10 μg/mL) or epratuzumab either in the Dried-I format (FIG. 3C, left panel; sample: hLL2*) or the Wet-I format (FIG. 3C, left panel; sample: hLL2) all resulted in the redistribution of CD22 to the lipid rafts (fractions 3-6, FIG. 8). However, redistribution of CD79b to lipid rafts (FIG. 3C, right panel) was observed only with anti-IgM or the Dried-I format (sample: hLL2*), but not with the Wet-I format (sample: hLL2). Additional experiments also revealed that only CD22, not CD79a or CD79b, could be detected in lipid rafts from cells treated with soluble epratuzumab either in the Wet-I (FIG. 3D, lane 2) or the Wet-IIA format (FIG. 3D, lane 5). These results confirm the ability of soluble epratuzumab (the Wet-I format) to stabilize the localization of CD22 in lipid rafts (Qu et al., 2008, Blood 111:2211-19), and suggest that the cytotoxicity of epratuzumab requires the concurrent translocation of CD22, CD79a, and CD79b to lipid rafts.

Figure 4A:
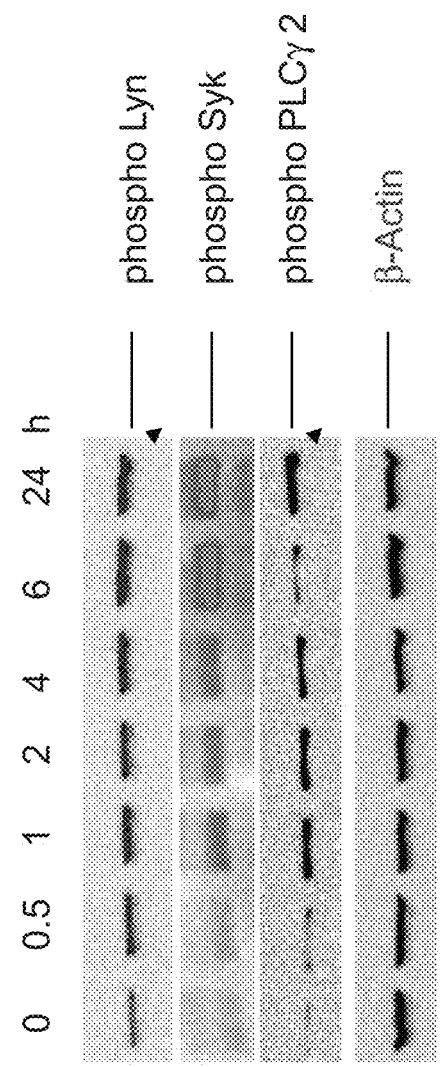
FIG. 4A. Phosphorylation of BCR-mediated signals, modulation of MAP kinases, and evidence of caspase-dependent apoptosis. D1-1 cells were incubated with the Dried-I format of epratuzumab for the indicated times and cell lysates probed for phosphorylated Lyn, Syk, or PLCγ2.
Figure 4B:
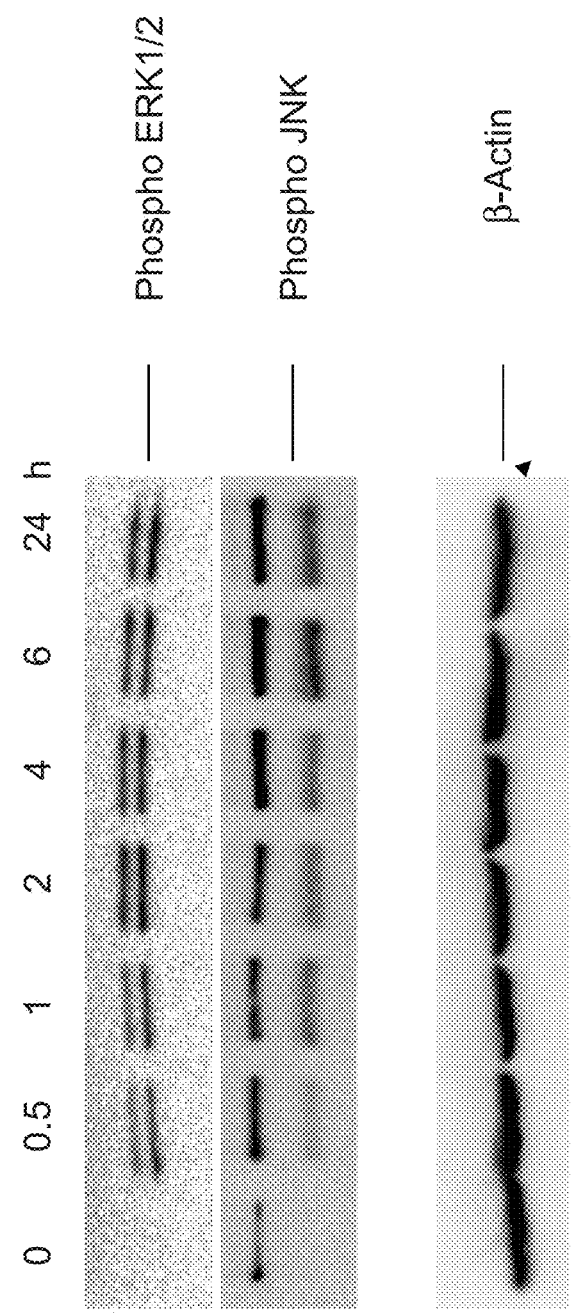
FIG. 4B. Phosphorylation of BCR-mediated signals, modulation of MAP kinases, and evidence of caspase-dependent apoptosis. The cell lysates of D1-1 cells obtained as described in the legend to FIG. 4A were probed for phosphorylated ERKs and JNK.
Figure 4C:
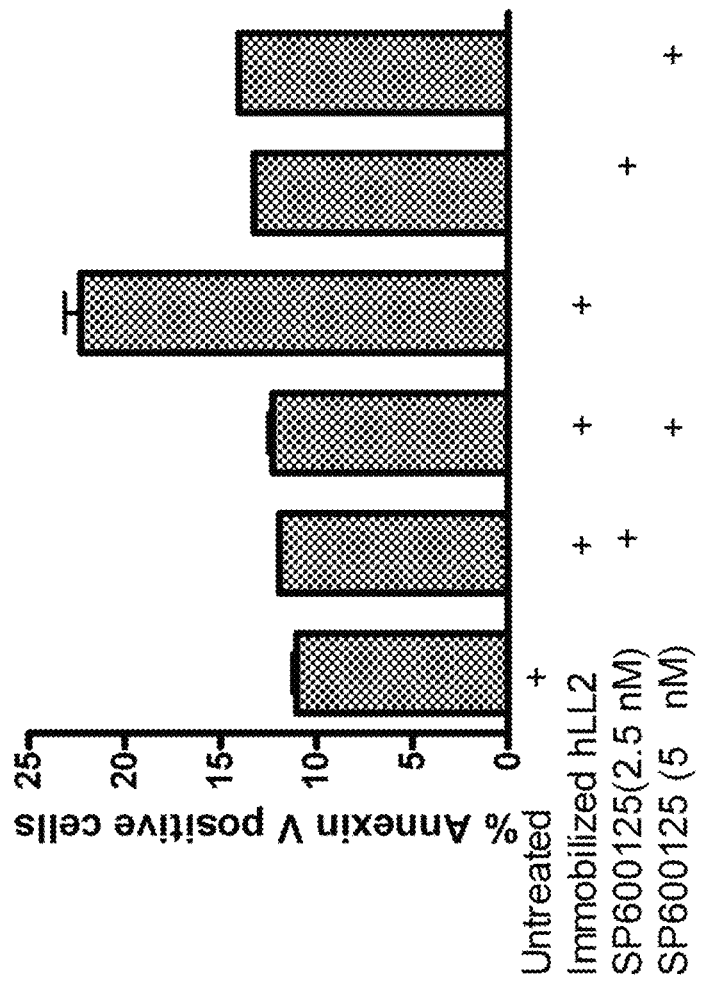
FIG. 4C. Phosphorylation of BCR-mediated signals, modulation of MAP kinases, and evidence of caspase-dependent apoptosis. SP600125, a chemical inhibitor for JNK, protected D1-1 cells from apoptosis induced by plate-immobilized epratuzumab.

Activation of BCR-mediated signals and modulation of MAP kinases. The Dried-I format of epratuzumab induced in D1-1 cells rapid and prolonged phosphorylation of Lyn, Syk, and PLCγ2, as shown in FIG. 4A. Changes of intracellular signals induced by the Dried-I format also included a rapid (detectable within 30 min) and continuous (over a period of 24 h) activation of both ERKs and JNKs (FIG. 4B). A functional role of JNK was established by showing SP600125, a known inhibitor of JNK, given at low doses (2.5 and 5 nM) to D1-1 cells 2 h before treatment with plate-immobilized epratuzumab, could effectively prevent apoptosis when determined at 24 h (FIG. 4C).

Figure 4D:
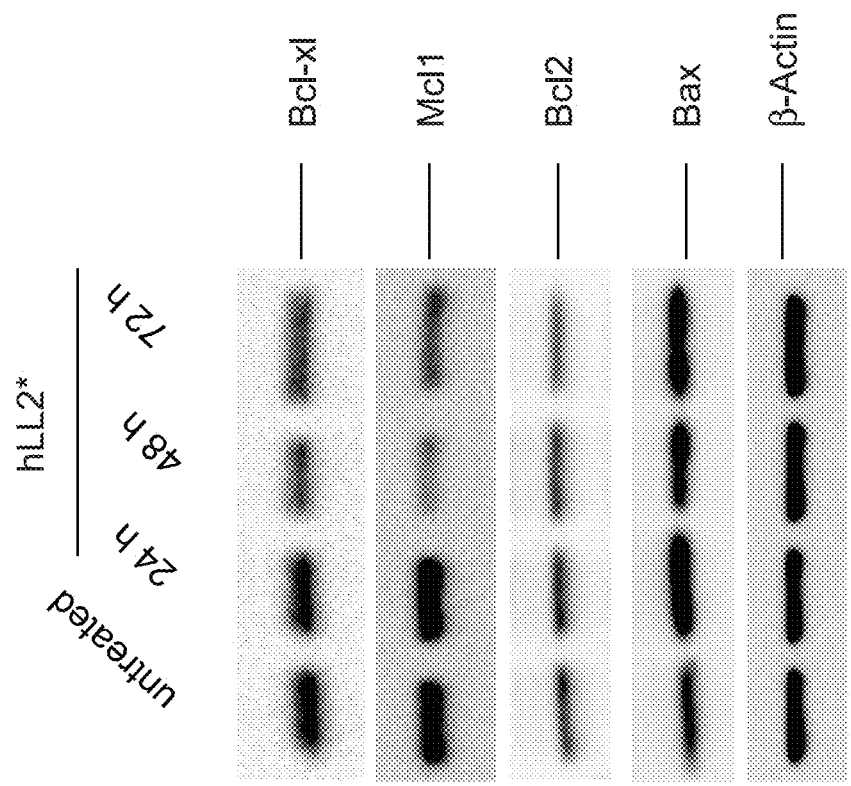
FIG. 4D. Phosphorylation of BCR-mediated signals, modulation of MAP kinases, and evidence of caspase-dependent apoptosis. Western blot analysis of selective anti- and pro-apoptotic proteins following treatment of D1-1 cells with plate-immobilized epratuzumab for 24, 48 and 72 h. The untreated sample at 72 h is shown.
Figure 4E:
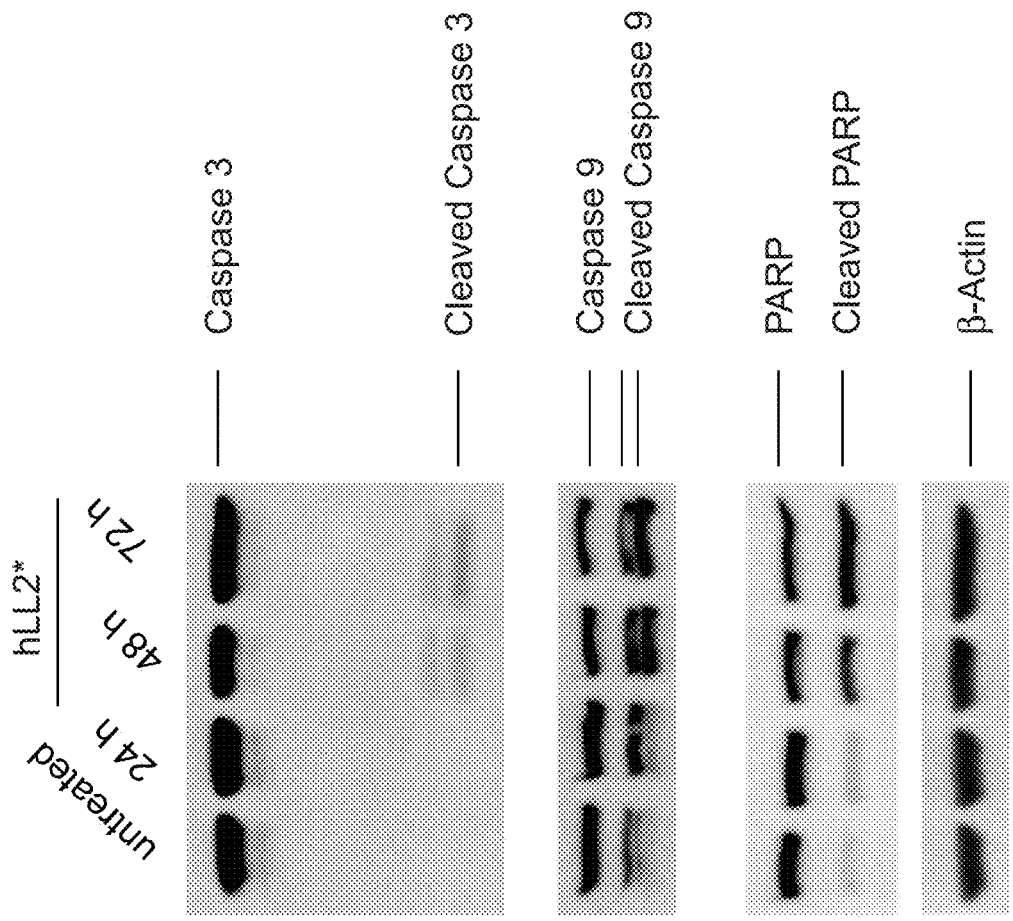
FIG. 4E. Phosphorylation of BCR-mediated signals, modulation of MAP kinases, and evidence of caspase-dependent apoptosis. Plate-immobilized epratuzumab (hLL2*) induced cleavages of caspase 3, caspase 9 and PARP, which were evident at 48 and 72 h. The untreated sample at 72 h is shown. (F) Z-VAD-fmk inhibited apoptosis in D1-1 cells induced by plate-immobilized epratuzumab.
Figure 4F:
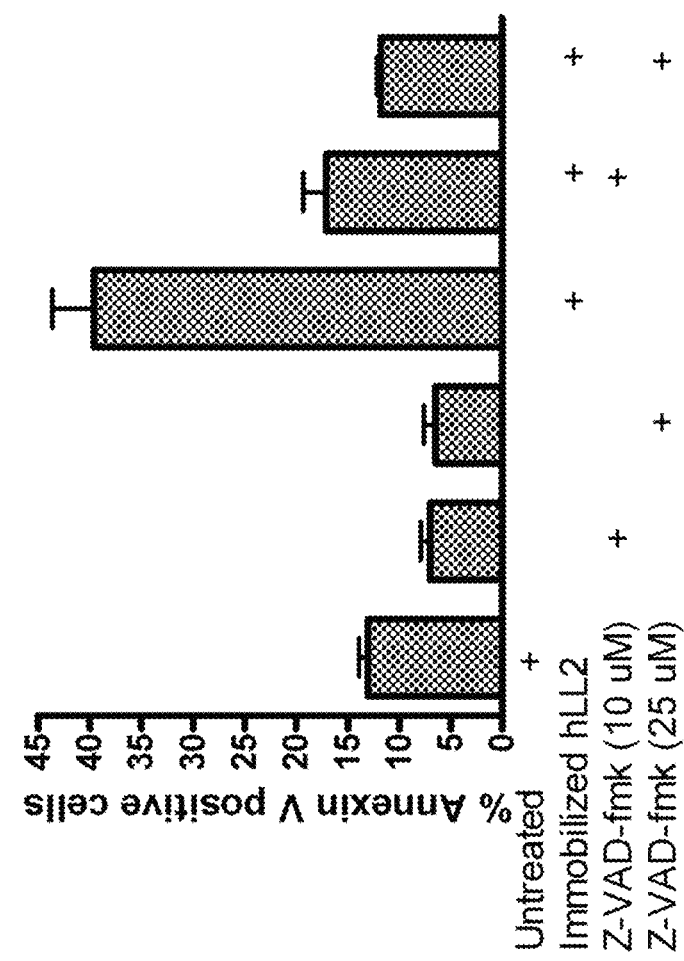
FIG. 4F. Z-VAD-fmk inhibited apoptosis in D1-1 cells induced by plate-immobilized epratuzumab (hLL2*).

Caspase-mediated apoptosis. The effect of the Dried-I format on the basal levels of selective pro-apoptotic and anti-apoptotic proteins, was evaluated in D1-1 cells following treatment for 24, 48 and 72 h. As shown in FIG. 4D, the Dried-I format (sample: hLL2*) downregulated anti-apoptotic Bcl-xL and Mcl-1, while increasing the expression level of pro-apoptotic Bax; the results pertaining to Bcl-2 were less certain, however. The observed cleavage of caspase 3, caspase 9 and poly ADP ribose polymerase (PARP), as shown in FIG. 4E, indicates the Dried-I format orchestrates a caspase-dependent apoptosis in D1-1 cells, which could be reduced from about 40% to a level similar to the untreated cells (about 15%) by the pan-caspase inhibitor, Z-VAD-fmk, at 10 or 25 µM (P<0.02), as shown in FIG. 4F. It is noted that untreated controls shown in FIG. 4D and FIG. 4E were taken at the 72-h time-point, and there was no change in untreated samples when examined at either 24 h or 48 h.

Figure 5A:
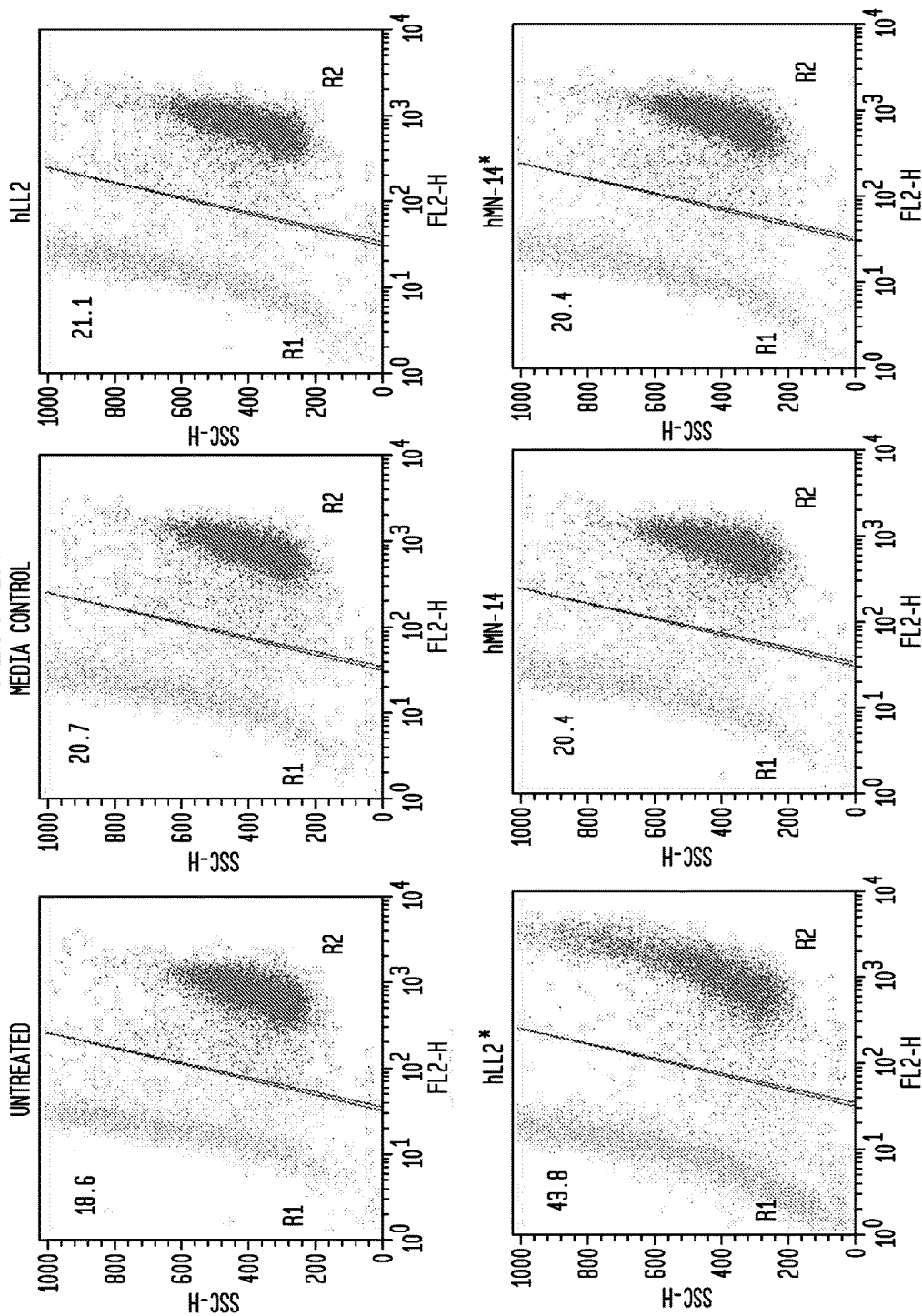
FIG. 5A. Effect on $\Delta\psi_m$ and ROS. Treatment of D1-1 cells with the Dried-I format of epratuzumab induced a decrease in $\Delta\psi_m$.
Figure 5B:
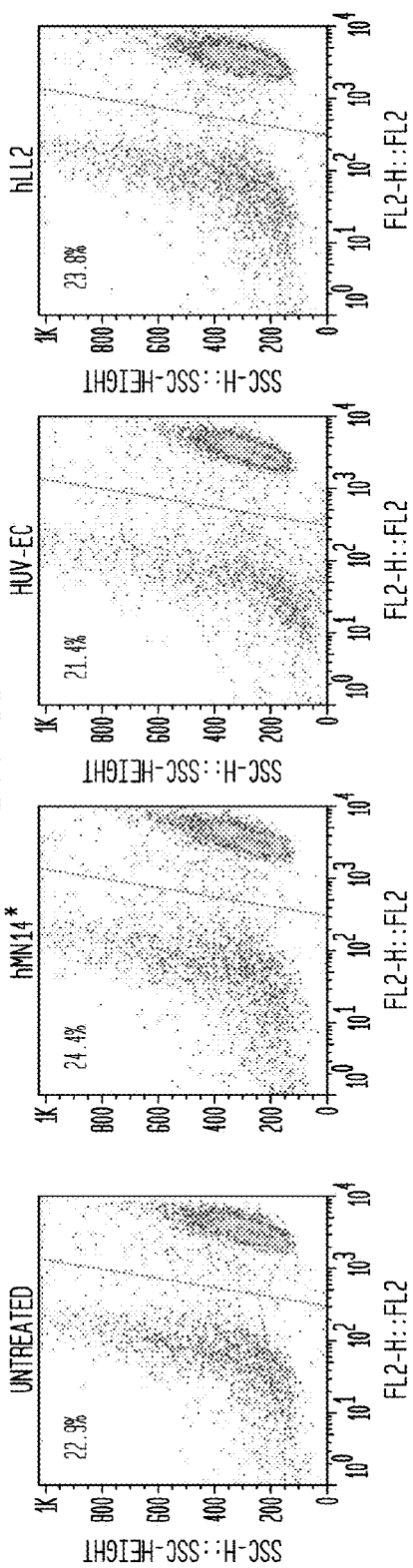
FIG. 5B. Effect on $\Delta\psi_m$ and ROS. Treatment of Daudi cells with the Dried-II format also induced a decrease in $\Delta\psi_m$, similar to that observed in D1-1 cells with the Dried-I format.
Figure 5B:
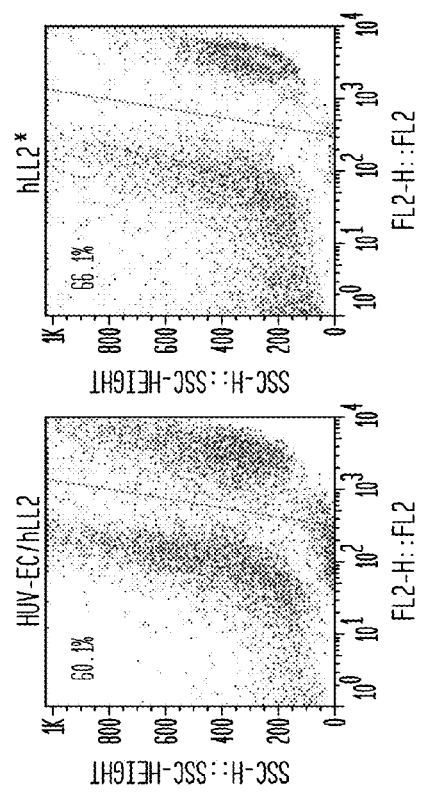
Figure 5C:
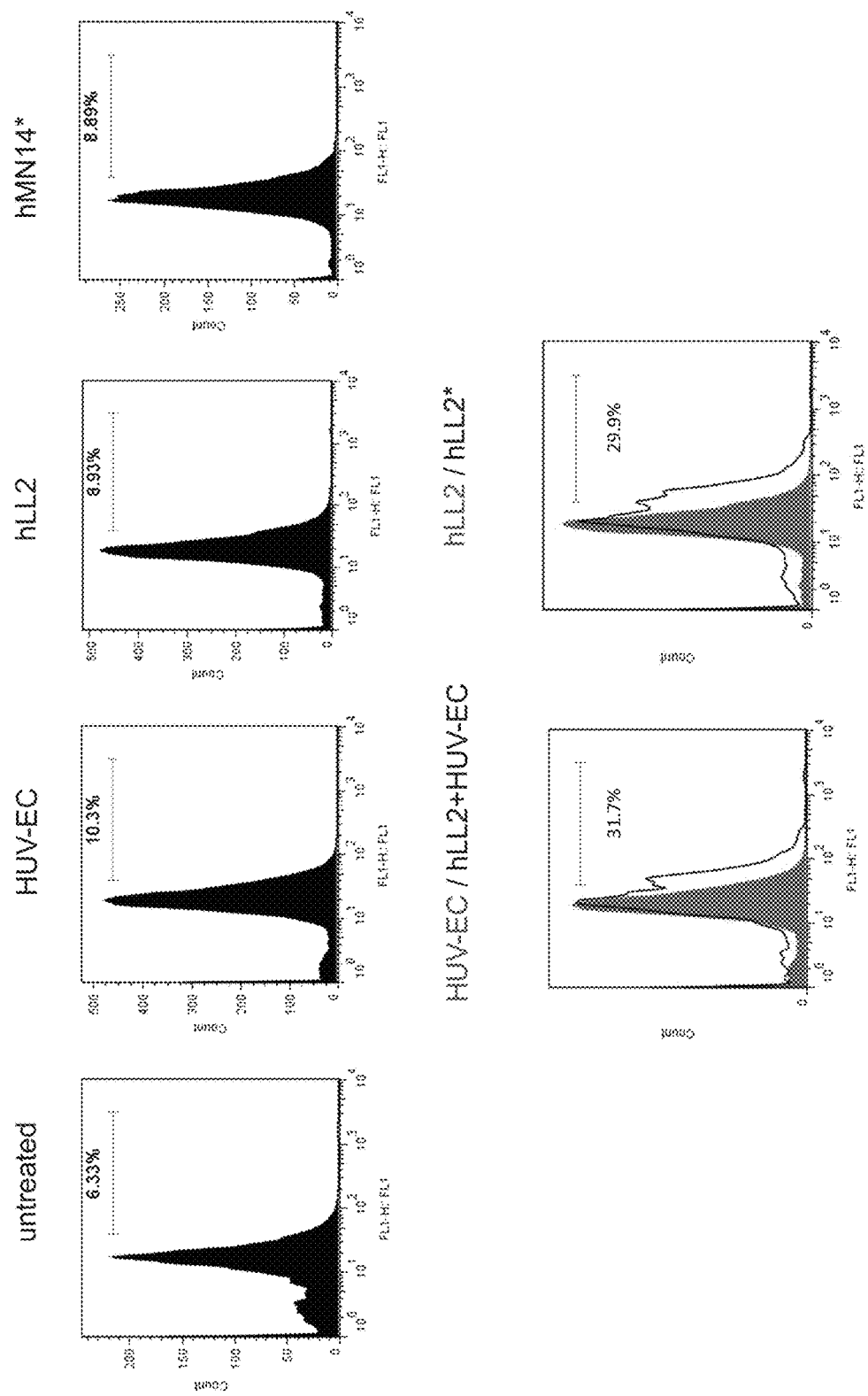
FIG. 5C. Effect on $\Delta\psi_m$ and ROS. Both the Dried-I and the Dried-II formats of epratuzumab increased the generation of ROS in Daudi cells.

Decrease in $\Delta\psi_m$ and generation of ROS. In FIG. 5A, the Dried-I format (sample: hLL2*) was shown to induce mitochondrial membrane depolarization, manifested as a decrease in $\Delta\psi_m$, in about 45% of D1-1 cells, whereas no more than 20% of cells with comparable changes could be detected in the five controls. Similar results were observed for the Dried-I format in Ramos cells (data not shown) and in about 60% of Daudi cells treated with the Dried-I format (FIG. 5B, subpanel: hLL2*) or the Dried-II format (FIG. 5B, subpanel: HUV-EC/hLL2), which replaced plate-immobilized epratuzumab with soluble epratuzumab and plate-coated HEV-EC. To corroborate such findings, both the Dried-I (FIG. 5C, subpanel: hLL2*) and the Dried-II (FIG. 5C. subpanel: HUV-EC/hLL2) formats increased the generation of ROS in about 30% of the cells, as compared to about 6% in the untreated control, and about 9 to 10% in cells incubated with the Wet-I format (FIG. 5C, subpanel: hLL2), isotype control of the Dried-I format (FIG. 5C, subpanel: hMN-14*) or HEV-EC in the absence of epratuzumab (FIG. 5C, subpanel: HUV-EC).

Figure 6A:
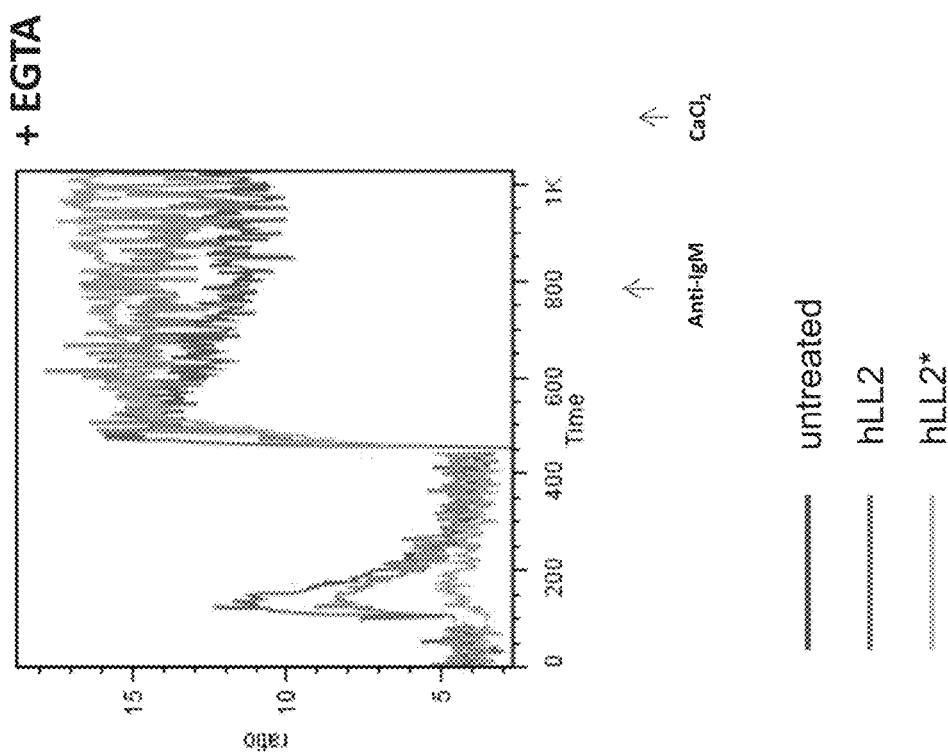
FIG. 6A. Decrease in intracellular calcium release and perturbation of actin dynamics. Pretreatment of Daudi cells with soluble (Wet-I) or immobilized (Dried-I) epratuzumab for 1 h reduced the mobilization of intracellular calcium ions following stimulation with anti-IgM, but did not affect the subsequent entry of extracellular calcium.
Figure 6B:
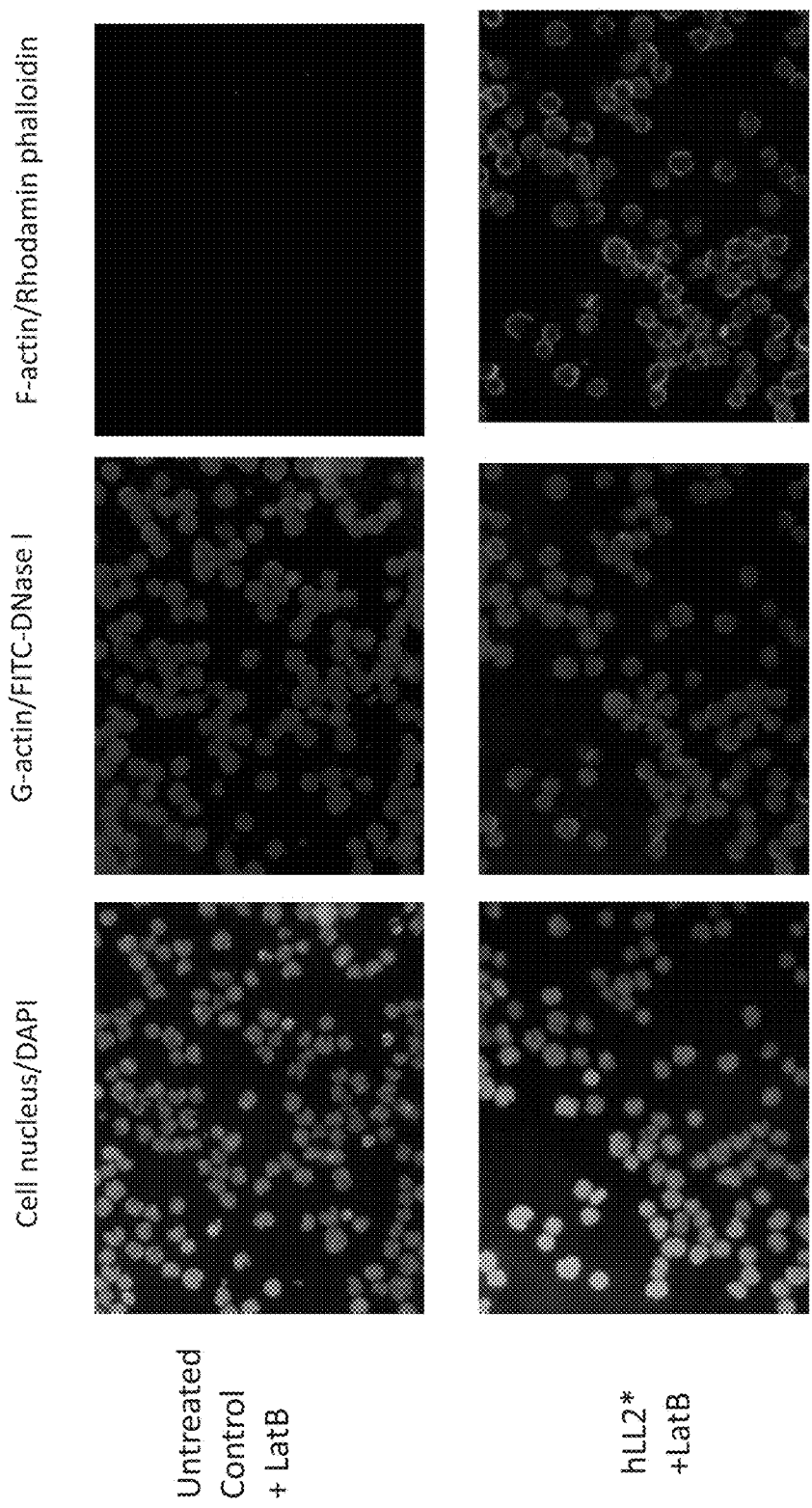
FIG. 6B. Decrease in intracellular calcium release and perturbation of actin dynamics. The ligation of CD22 by plate-immobilized epratuzumab stabilized the F-actin from depolymerization by LatB.
Figure 6C:
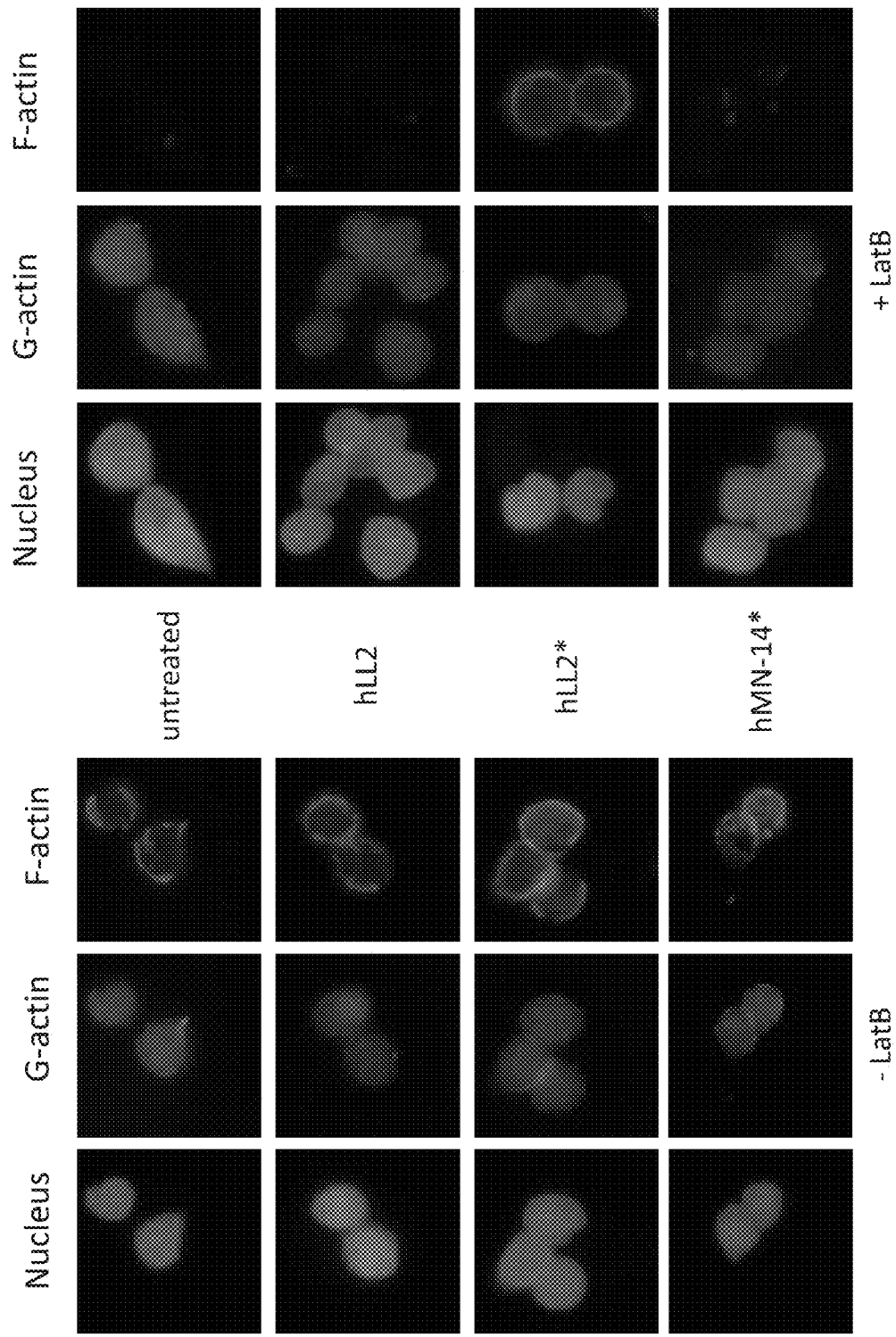
FIG. 6C. Decrease in intracellular calcium release and perturbation of actin dynamics. Before the addition of LatB (left panel), F-actin was visualized by staining with rhodamin phalloidin in untreated Daudi cells, as well as in cells pretreated with the Dried-I format of epratuzumab (hLL2*), the isotype control of the Dried-I format (hMN-14*), or the Wet-I format of epratuzumab (hLL2). The addition of LatB (right panel) did not affect the staining of F-actin in cells pretreated with hLL2*, but demolished the staining of F-actin in the other three.

Effect on calcium mobilization and actin dynamics. In Daudi cells, pretreatment with either the Wet-I or the Dried-I format for 1 h notably reduced the amplitude of calcium ions released from intracellular stores following stimulation with anti-IgM, with a larger effect incurred by the plate-immobilized than the soluble epratuzumab; however, the subsequent entry of extracellular calcium was minimally affected (FIG. 6A). The ligation of CD22 by plate-immobilized epratuzumab appeared to stabilize F-actin from depolymerization by LatB, when analyzed at 5 min after the addition of LatB, as evidenced by the prominent staining of F-actin by rhodamin phalloidin, which was absent in the untreated Daudi cells, as shown in FIG. 6B. Additional results shown in FIG. 6C indicate that the addition of LatB did not affect the staining of F-actin in cells pretreated with hLL2*, but demolished the staining of F-actin in cells treated with soluble epratuzumab or the isotype control of the Dried-I format (hMN-14*).

Discussion

In the present study, we confirmed that ligation of mIgM by a sufficient amount of anti-IgM (10 µg/mL) induced the phosphorylation of CD22, CD79a and CD79b, and the localization of all three phosphorylated proteins in lipid rafts, leading to cell death in D1-1, a subline of Daudi selected for a higher expression of mIgM. We further show that ligation of CD22 with plate-immobilized epratuzumab (the Dried-I format) induced a similar change in CD22, CD79a and CD79b, including phosphorylation, translocation into lipid rafts, and subsequent cell death. Thus, it appears that for a CD22-binding agent such as epratuzumab to kill Daudi cells in particular, and perhaps other CD22-expressing B-cell lymphomas, two critical events must occur in concert, (i) phosphorylation of CD22, CD79a and CD79b above a threshold level, and (ii) their movement to lipid rafts. This conclusion is supported by the finding that little or no cell death was observed for D1-1 cells with the Wet-II format comprising a secondary crosslinking GAH antibody at 10 µg/mL and either soluble epratuzumab at 7.5 µg/mL or a suboptimal amount of anti-IgM (1 µg/mL). The former treatment efficiently induced phosphorylation of CD22 and its localization to lipid rafts (FIG. 3D, lane 5), but was unable to phosphorylate CD79a and CD79b (FIG. 3B, lane 4), whereas the latter treatment failed to phosphorylate CD22, CD79a and CD79b to a detectable level (FIG. 3B, lane 6). On the other hand, combining these two treatments in the Wet-III format could result in phosphorylation of CD22, CD79a and CD79b (FIG. 3B, lane 7), their localization into lipid rafts (FIG. 3D, lane 4), and consequently, cell death, as observed for anti-IgM at 10 µg/mL or the Dried-I format of epratuzumab.

Binding of CD22 to beads coated with B3 antibody (a murine anti-hCD22 mAb) was reported to lower the threshold concentration of anti-IgM required for stimulating DNA synthesis in tonsillar B cells by two orders of magnitude, presumably due to sequestration of CD22 from mIgM by restricting the lateral movement of CD22 in the plane of the cell membrane (Doody et al., 1995, Science 269:242-33). Our results show, however, that the ability of high-density, plate-immobilized or bead-conjugated epratuzumab to engage CD22 along with co-clustering, rather than sequestration, of mIgM, constitutes a sufficient condition for cell killing in the total absence of anti-IgM, which may be further strengthened by the co-localization of both mIgM and CD22 in lipid rafts. Moreover, the binding of immobilized epratuzumab to CD22 is distinctive from that of a synthetic α2,6-linked sialic acid, which efficiently prevented CD22 from co-capping and co-localization with BCR in the lipid rafts after BCR ligation (Yu et al., 2007, Biochem Biophys Res Commun 360:759-64).

Intriguingly, we did not observe any transient increase in intracellular calcium by immobilized epratuzumab in the Particulate-I format, but have noted a substantial decrease of anti-IgM-induced mobilization of intracellular calcium in Daudi cells pretreated with either the Dried-I or the Wet-I format of epratuzumab for 1 h. These results are consistent with two previous findings: one reporting that a copolymer comprising multiple copies of 2,4-dinitrophenyl (DNP) and a synthetic CD22 ligand (CD22L), which was capable of trans-binding to CD22 via colligation with BCR in a murine B cell line displaying a DNP-specific BCR, failed to induce any calcium flux (Courtney et al., 2009, Proc Natl Acad Sci USA 106:2500-05); the other reporting that preincubating B cells with the IgG or F(ab')$_2$ of epratuzumab reduced the amplitude of calcium mobilization stimulated by anti-IgM/IgG (Sieger et al., 2013, Arthritis Rheum 65:770-79). Thus, when both CD22 and BCR are co-clustered by immobilized epratuzumab or the DNP-CD22L copolymer, calcium signals resulting from BCR stimulation can be partially or completely suppressed, which is in contrast to the enhanced calcium flux found in B cells pretreated with certain anti-CD22 antibodies upon BCR activation, often attributed to sequestration of CD22 from BCR (Rudge et al., 2002, J Exp Med 195:1079-85; Chan et al., 1998, Curr Biol 8:545-53). Although certain intracellular events observed for the Dried-I format of epratuzumab and the DNP-CD22L copolymer were similar, such as a more sustained phosphorylation of CD22 and Lyn, differences in their opposing effect on pSyk and pPLCγ2 also should be noted.

Whereas the ability of an anti-mIg to induce calcium flux may or may not lead to cell death in B-cell lymphoma, as reported for B104 (Ishigami et al., 1992, J Immunol 148:360-68), a human B-cell lymphoma line expressing BCR of both mIgM and mIgD, we show with the Dried-I format of immobilized epratuzumab that potent inhibition of cell proliferation with apoptosis also can be independent of calcium mobilization. Thus, besides the routine measurement of intracellular calcium as a marker for B-cell activation and cell surface binding to assess the affinity for CD22, the biological significance of CD22-targeting agents, particularly those derived from synthetic sialosides (Yu et al., 2007, Biochem Biophys Res Commun 360:759-64; Courtney et al., 2009, Proc Natl Acad Sci USA 106:2500-05; O'Reilly et al., 2008, J Am Chem Soc 130:7736-46; Abdu-Allah et al., 2008, J Med Chem 51:6665-81; Abdu-Allah et al., 2011, Bioorg Med Chem 19:1966-71), should be substantiated with a suitable cytotoxicity assay, as exemplified by the capability of liposomal nanoparticles displaying both antigen and CD22L to induce antigen-specific B-cell apoptosis (Macauley et al., 2013, J Clin Invest 123:3074-83).

Figure 7A:
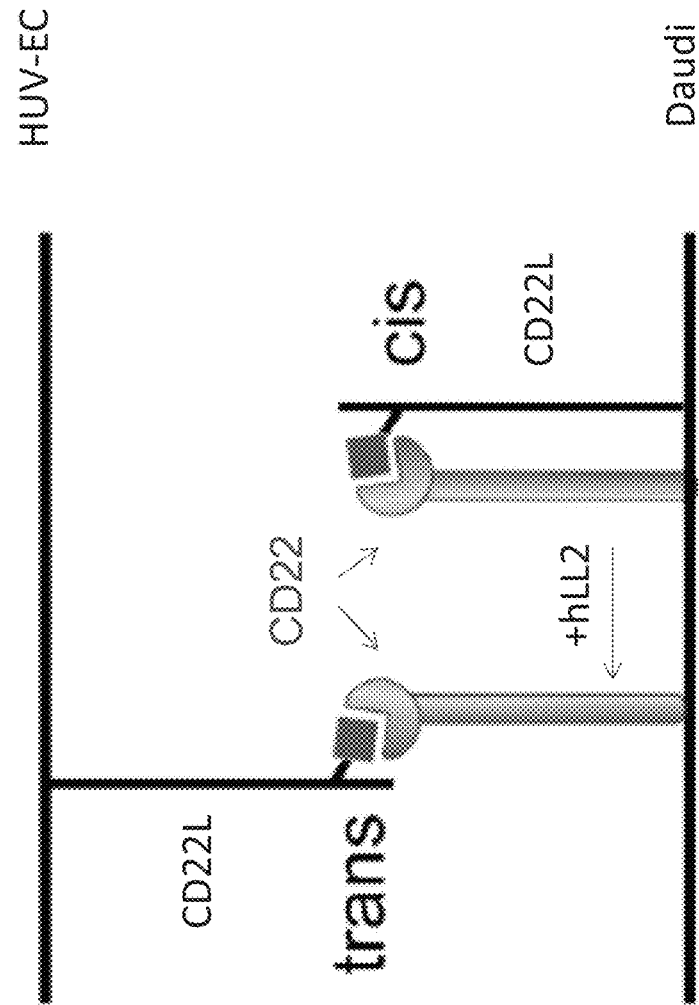
FIG. 7A. Schematics of proposed mechanism of epratuzumab-mediated interaction of endothelial cells with CD22-expressing B cells. CD22 can interact with CD22L (sialylated glycoproteins) on the same (cis) or different cells (trans). To induce the trans interaction, it is necessary to overcome the cis interaction, which may be provided by non-ligand-blocking epratuzumab. Because Daudi cells have a high levels of CD22L, the binding of CD22 to (activated) endothelial cells are inhibited by cis-binding. The ligation of hLL2 to CD22 is likely to break up the cis-interaction and because hLL2 is not a blocking antibody, hLL2 may not interfere with the further binding of CD22 to the CD22L expressed on activated endothelial cells. Thus hLL2 plays an indirect role to facilitate an efficient binding of B cells to endothelial cells, which mimics the direct binding of B cells to immobilized hLL2.
Figure 7B:
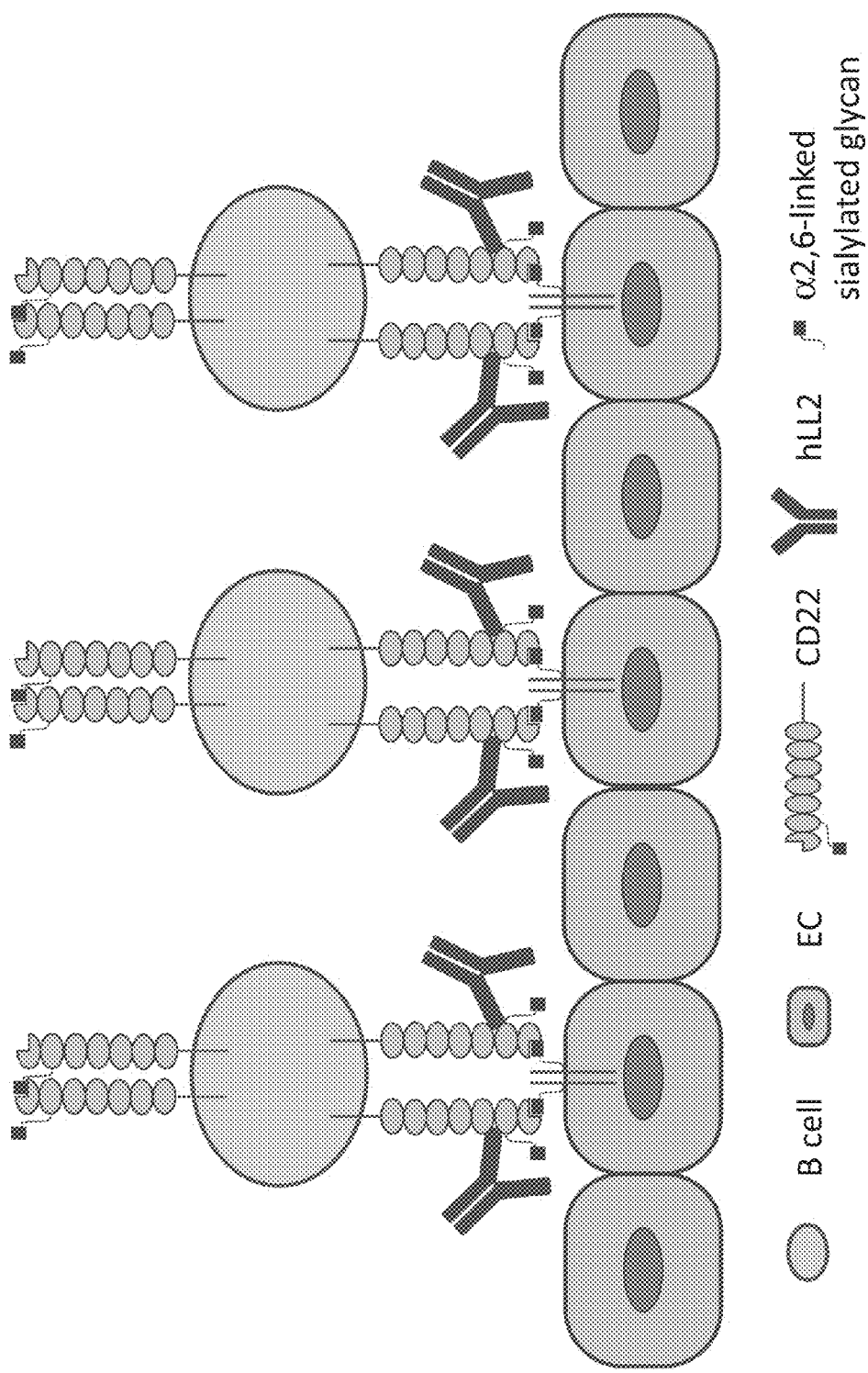
FIG. 7B. Schematics of proposed mechanism of epratuzumab-mediated interaction of endothelial cells with CD22-expressing B cells. Epratuzumab enables the attachment of CD22-expressing B cells to EC in the endothelium via the trans-interaction of CD22 with CD22L.
Figure 7C:
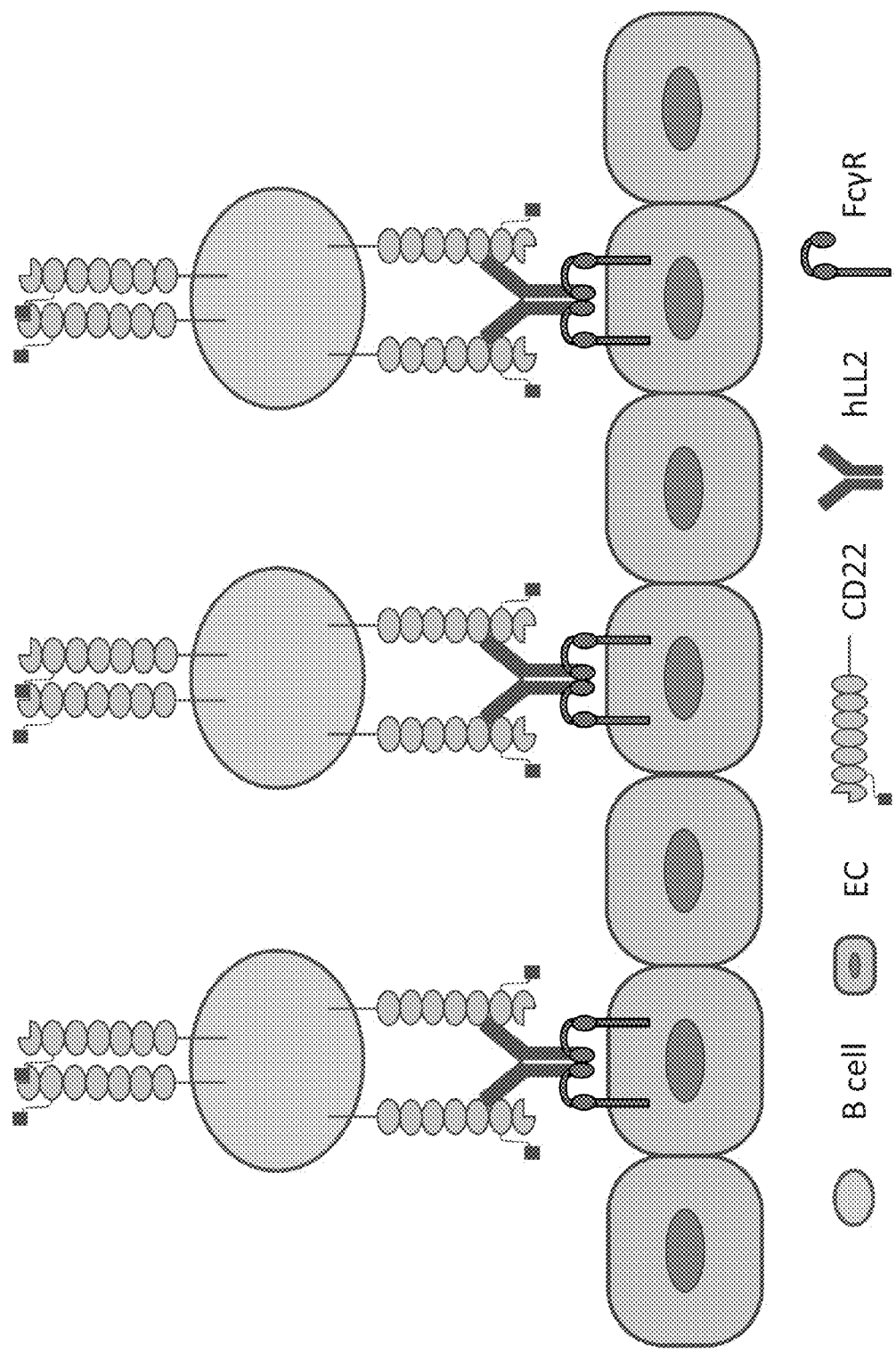
FIG. 7C. Schematics of proposed mechanism of epratuzumab-mediated interaction of endothelial cells with CD22-expressing B cells. Epratuzumab links CD22-expressing B cells to EC in the endothelium via the Fc-FcγR binding.

Despite their difference in calcium mobilization, resemblances of anti-IgM and immobilized epratuzumab were revealed in several intracellular events, including caspase-dependent apoptosis, reduced $\Delta\psi_m$, generation of ROS, and a similar profile of phosphorylated Lyn, Syk, PLCγ2, ERKs and JNKs. Moreover, the novel observation that some of the in vitro effects displayed by the Dried-I format of immobilized epratuzumab, including apoptosis, drop in $\Delta\psi_m$, and generation of ROS, could be induced by co-cultivation of Daudi cells with HUV-EC in the presence of soluble epratuzumab (the Dried-II format) implies a physiological relevance of immobilized epratuzumab. Collectively, the present data support the hypothesis that the non-ligand-blocking epratuzumab may act in vivo by unmasking CD22 to facilitate the trans-interaction of B cells with vascular endothelium (FIG. 7A), thereby inducing the various in vitro effects of immobilized epratuzumab. Noting that cytokine-activated human endothelial cells (EC) express enhanced levels of CD22L (Hanasaki et al., 1994, J Biol Chem 269:10637-43) and can adhere to B cells whose endogenous binding of CD22 to CD22L have been disrupted (Hanasaki et al., 1995, J Biol Chem 270:7533-42), one scenario, as depicted in FIG. 7B, would be the immobilization of the immune complexes comprising epratuzumab and B cells to the endothelium via the association of CD22 on B cells with the CD22L-containing glycoproteins on EC. Because human EC also express CD32A (FcγRIIA) (Groger et al., 1996, J Immunol 156:1549-56; Pan et al., 1998, Clin Exp Immunol 112:533-38), an alternative explanation (FIG. 7C) would be the immobilization of the epratuzumab-B cell complex to the endothelium via the association of the Fc domain on epratuzumab with CD32A on EC. These two possibilities are not mutually exclusive, with both likely occurring in vivo, and provide a plausible mechanism mediated by epratuzumab that enables the strong interaction between B cells and EC due to concurrent engagement of multiple cell surface molecules present on both types of cells.

Knowing that binding of CD22 by soluble epratuzumab leads to internalization raises the question whether internalization of CD22 plays a role in the mechanism of cell killing. Taking a cue from CD20, which also interacts with BCR and affects calcium mobilization and its own degradation (Walshe et al., 2008, J Biol Chem 83:16971-84), the expression levels of CD22 as well as BCR on the cell surface may be critical for the activity of anti-CD22 mAbs. On the other hand, we speculate that immobilized epratuzumab may delay or prevent the internalization of BCR or CD22, or both, by changing actin dynamics and stabilizing the co-localized CD22 and BCR in the lipid rafts, leading to functional inactivation of BCR.

In conclusion, we provide evidence for the mechanism of action by which immobilized epratuzumab induces cytotoxic and cytostatic effects in CD22-expressing B-lymphoma lines with BCR of the IgM isotype. Our findings add to the existing knowledge that immobilized antibodies, such as those directed at CD3 (Geppert & Lipsky, 1987, J Biol Chem 138:1660-66), CD47 (Mateo et al., 1999, Nat Med 5:1277-84), or CD40 (Watanabe et al., 2003, J Immunol 171:5828-36), display different biological ability on target cells from their soluble counterparts, and establish that ligation of CD22 by immobilized epratuzumab perturbs BCR-mediated signals in malignant B cells without the involvement of anti-BCR antibodies. We also uncover, for the first time, a role of immobilized epratuzumab to stabilize F-actin and the potential of soluble epratuzumab to promote the adhesion of B cells to endothelial cells, which may occur in vivo to manifest the various biological activities observed for the immobilized epratuzumab in vitro. Since plate- or bead-immobilized epratuzumab may represent a surrogate in-vitro mechanism of antibody crosslinking in vivo, the current study suggests that other agents comprising multiple epratuzumab molecules are worth investigating, such as CD22-targeting immunoliposomes. These can be generated to provide a high number of epratuzumab molecules on the surface of each liposome, as has been shown for immunoliposomes comprising the anti-HER2 trastuzumab (Chiu et al., 2007, Mol Cancer Ther 6:844-55), anti-CD74 milatuzumab (Hertlein et al., 2010, Blood 116:2554-58), or an anti-transferrin receptor antibody (Wang et al., 2010, J Am Chem Soc 132:11306-13).

TABLE 2

In vitro conditions to evaluate the cytotoxicity of epratuzumab on CD22-expressing B cells.

| Conditions | Format |
|---|---|
| Target cells + epratuzumab IgG immobilized onto microtiter wells overnight | Dried-I |
| Target cells + labetuzumab IgG immobilized onto microtiter wells overnight | Isotype control for Dried-I |

TABLE 2-continued

In vitro conditions to evaluate the cytotoxicity
of epratuzumab on CD22-expressing B cells.

| Conditions | Format |
|---|---|
| Target cells + epratuzumab IgG over a monolayer of HUV-EC | Dried-II |
| Target cells + labetuzumab IgG over a monolayer of HUV-EC | Isotype control for Dried-II |
| Target cells + epratuzumab IgG or F(ab')$_2$ in solution | Wet-I |
| Target cells + epratuzumab IgG + GAH in solution | Wet-IIA |
| Target cells + epratuzumab IgG + anti-IgM (1 µg/mL) in solution | Wet-IIB |
| Target cells + epratuzumab IgG + GAH + anti-IgM (1 µg/mL) in solution | Wet-III |
| Target cells + epratuzumab IgG conjugated to polystyrene beads | Particulate-I |
| Target cells + epratuzumab IgG bound to Protein A-Sepharose | Particulate-II |
| Target cells + anti-IgM (10 µg/mL) in solution | Positive control |

Example 2

Epratuzumab-Induced Trogocytosis of
BCR-Response Modulating Proteins Ex Vivo

The humanized anti-CD22 antibody, epratuzumab, has demonstrated therapeutic activity in clinical trials of patients with non-Hodgkin lymphoma (NHL), acute lymphoblastic leukemia, primary Sjögren's syndrome, and systemic lupus erythematosus (SLE). Thus, epratuzumab offers a promising option for CD22-targeted immunotherapy of B-cell lymphomas and autoimmune diseases. However, its mechanism of action (MOA) remains incompletely understood to-date. Because epratuzumab has modest, but significant, antibody-dependent cell-mediated cytotoxicity and negligible complement-dependent cytotoxicity when evaluated in vitro, and its moderate depletion of circulating B cells in patients (35% on average) may be overestimated due to use of CD19$^+$ cells to measure B cells by flow cytometry (discussed below), the therapeutic action of epratuzumab in vivo may not result from B-cell depletion. We investigated whether ligation of epratuzumab to CD22 could modulate other surface molecules on B cells. In particular, we focused on those surface molecules involved in regulating antigen-specific B-cell receptor (BCR) signaling, since modulation of such molecules may lead to altered B-cell functions that ultimately mitigate symptoms of autoimmune or other diseases. With regard to its function of killing malignant B cells expressing CD22, our studies have shown that these effects are more related to the BCR signaling pathway than effector-cell function.

Here we report for the first time that epratuzumab induces a substantial reduction of CD22, along with CD19, CD21, CD20, and CD79b, on the surface of B cells in peripheral blood mononuclear cells (PBMCs) obtained from normal donors or lupus patients, and three NHL Burkitt cell lines (Daudi, Raji, and Ramos) spiked into normal PBMCs. The intriguing observation that only CD22, but not other surface markers, was appreciably decreased by epratuzumab in isolated NHL cells prompted us to assess the role of FcγR-bearing effector cells, with the finding that epratuzumab effectively mediates trogocytosis [a process whereby cells binding to antigen-presenting cells extract surface molecules from these cells and express them on their own surface] of multiple surface proteins from B cells to monocytes, NK cells, and neutrophils. This mechanism of action may explain the limited effectiveness of high doses of epratuzumab compared to lower doses in patients with SLE.

Peripheral blood mononuclear cells (PBMCs) obtained from healthy donors were incubated overnight (16-24 h) with 10 µg/mL of either epratuzumab or an isotype control mAb (hMN-14) and the relative levels of various antigens on the surface of the B cells were analyzed by flow cytometry. PBMCs from heparinized whole blood of normal donors were isolated by density gradient centrifugation on UNI-SEP tubes (Novamed Ltd, Israel). PBMCs were reconstituted in RPMI media supplemented with 10% heat inactivated fetal bovine serum and plated at a cell density of 1.5×10$^6$/mL in non-tissue culture treated 48-well plates. Epratuzumab or hMN-14 were added to triplicate wells at a final concentration of 10 µg/mL and incubated overnight (16-20 h) before staining with fluorescent-labeled primary antibodies (Biolegend) following the manufacturers suggested protocols. Stained cells were analyzed by flow cytometry on a FACSCALIBUR® (BD Biosciences) using Flowjo (V7.6.5) software. Initially, the lymphocyte population was gated by side vs. forward scattering, and B cells were further gated from this population with the CD19 signal. The mean fluorescence intensity (MFI), obtained with fluorochrome-conjugated antibodies to various cell surface antigens, on the gated B cells was calculated following treatment with epratuzumab, hMN-14 or without antibody. PBMCs from 16 healthy donors were assessed in various experiments.

Treatment with the control mAb (hMN-14) did not affect the levels of any of the tested proteins and resulted in MFI measurements that were very similar to untreated samples. Alternatively, epratuzumab significantly reduced the levels of key BCR-regulating proteins, including CD22, CD19, CD21 and CD79b, which were reduced to 10, 50, 52 and 70%, respectively, of the level of untreated or control mAb (not shown). CD20 (82%) and CD62L (73%) also were reduced, but to a lesser extent. Other surface proteins including CD27 (on CD27$^+$ B cells), CD40, CD44, CD45, β7 integrin and LFA-1 (CD11a and CD18) were affected minimally (<10% change) by epratuzumab. CD27$^-$ naive B cells were more responsive to epratuzumab compared to CD27$^+$ memory B cells, as shown with PBMCs as shown for CD19 from 3 different healthy donors (not shown). CD22, CD21 and CD79b were also reduced to a greater extent on CD27$^-$ cells (not shown). The effect was essentially complete within a few hours. The reductions in surface CD19 and CD21 were not significantly different following 2-h or overnight treatment (not shown).

Example 3

Dose-Dependent Trogocytosis with Epratuzumab

The effect of epratuzumab on the cell surface levels of CD19, CD21, CD22 and CD79b was compared using the standard (10 µg/mL) concentration with a 100-fold higher concentration (1 mg/mL). An additional treatment included 10 µg/mL epratuzumab combined with 1 mg/mL hMN-14. Compared to the lower concentration of epratuzumab (10 µg/mL), the higher concentration (1 mg/mL) resulted in significantly (P<0.02) less reduction in CD22, CD19, CD21 and CD79b (not shown). Competition with high concentration (1 mg/mL) hMN-14 significantly (P<0.003) reduced the effect of epratuzumab (10 µg/mL) on CD22 and CD19, but to a lesser extent than high-dose epratuzumab. A titration experiment, where normal PBMCs were incubated overnight with epratuzumab at concentrations ranging from 0.1-1000 µg/mL, confirmed that doses approaching 1 mg/mL dampened the effect (not shown). A second titration covering 8 logs (1 ng/mL-10 mg/mL) produced a classic U-shaped curve with substantial dampening at concentrations lower than 10 ng/mL or greater than 1 mg/mL (not shown). The reduction of both CD22 and CD19 on B cells within PBMCs was similar over a wide concentration range (10 ng/mL-100 µg/mL) of epratuzumab.

Example 4

Effector Cells are Required for Epratuzumab-Induced Trogocytosis

B cell lymphoma cell lines were used as "isolated B cells" that were evaluated for epratuzumab induced trogocytosis. In vitro, epratuzumab induced an intermediate reduction (33% control) of CD22 on the surface of isolated Daudi Burkitt lymphoma cells, and did not affect the levels of other markers (not shown). In an ex vivo setting, where Daudi were spiked into PBMCs from a healthy donor, epratuzumab minimized CD22 (<5% control) and significantly (P<0.0001) reduced CD19 (28% control), CD21 (40% control), CD79b (72% control) and surface IgM (73% control). Similar results were obtained with Raji lymphoma cells, where CD19, CD21 and CD79b were diminished by epratuzumab only in the presence of PBMCs (not shown). The addition of a crosslinking second antibody resulted in only a modest reduction of CD19, CD21 and CD79b. That the effect only was observed in the presence of PBMCs, and it was not accomplished in the presence of PBMCs with a F(ab')$_2$ fragment or with a crosslinking second antibody in place of PBMCs, indicates that effector cells bearing Fc receptors are involved in the epratuzumab-induced trogocytosis process.

Example 5

Monocytes, but not T Cells can Modulate Epratuzumab-Induced Trogocytosis

Combined, T cells and monocytes comprise approximately 70-80% of the total PBMCs. The ability of PBMC fractions, which were depleted of either T cells or monocytes using MACS separation technology (Miltenyi Biotec) with magnetically labeled microbeads in an LS or MS column, were evaluated for epratuzumab-induced reduction of CD22 and CD19 on Daudi and normal B cells. For this experiment the ratio of total effector cells to Daudi was held constant. Therefore, removal of a specific cell type resulted in increased numbers of the remaining cell types (not shown). Depletion of T cells was only 50% efficient; however, this resulted in a 10% increase in monocytes and other cell types. The T-cell-depleted PBMCs were significantly more active than total PBMCs, indicating that T cells are not involved (not shown). Indeed, purified T cells were not capable of affecting the epratuzumab-induced reduction of CD19 or CD21 on Daudi (not shown). Conversely, depletion of monocytes, which was 99% efficient (not shown), significantly dampened the reduction of both CD19 and CD22 on either Daudi or B cells (not shown), implicating the involvement of monocytes. That there was appreciable reduction of CD19 with the monocyte-depleted PBMCs, suggests the participation of additional cell types. In a subsequent experiment, purified monocytes (94%) induced a similar decrease in CD19 as the whole PBMCs, whereas the remaining monocyte-depleted PBMCs had minimal effect, comparable to the levels measured without effector cells (not shown). A similar pattern was observed for CD22. This particular donor gave relatively weak activity (25% reduction in CD19) compared to most others, where we have typically observed a 40-60% reduction in CD19. Nonetheless, the results support the key role of monocytes among PBMCs.

Example 6

Ex Vivo Trogocytosis with SLE Patient PBMCs

PBMCs were isolated from blood specimens of systemic lupus erythematosus (SLE, lupus) patients, who had yet to receive any therapy for their disease (naïve), and treated ex vivo with epratuzumab, using the same method that was applied to PBMCs from healthy donors. PBMCs of naive SLE patients responded similarly to healthy PBMCs (as in Example 2), where CD22, CD19, CD21 and CD79b on the surface of B cells were reduced to 11±4, 53±8, 45±4 and 75±1% control, respectively (not shown). Also similar to the results from normal donor PBMCs, CD27$^-$ naive B cells were more responsive than CD27$^+$ memory B cells (not shown), and, a F(ab')$_2$ fragment of epratuzumab did not induce the reduction of CD19, CD21 or CD79b (not shown). PBMCs isolated from blood specimens of SLE patients who currently were on epratuzumab immunotherapy had minimal response to the ex vivo treatment with epratuzumab (not shown), presumably due to low levels of CD22 on their B cells, resulting from therapy.

Example 7

Surface Levels of CD19, CD21, CD22 and CD79b on SLE Patient B Cells on Epratuzumab Immunotherapy The relative levels of CD22, CD19, CD21 and CD79b on B cells from five SLE patients who were receiving epratuzumab immunotherapy, were compared the results obtained from four naive lupus patients and two receiving BENLYSTA®, using identical conditions (Table 3).

TABLE 3

Comparison of B cells from lupus patients

| Patient | Treatment | % B cell in lymphgate | CD19 (PE-Cy7) | CD21 (FITC) | CD22 (FITC) | CD79b (APC) |
|---|---|---|---|---|---|---|
| S7 | E, P, M | 0.5 | 99 | 9 | 16 | 186$^{PE}$ |
| S8 | P, I | 5.0 | 145 | nd | 84 | nd |
| S9 | B | 0.5 | 218 | 21 | 48 | 470$^{PE}$ |
| S10 | B | 0.9 | 204 | 20 | 133 | 425$^{PE}$ |
| S11 | None | 18.0 | 195 | 51 | 106 | 608 |
| S12 | None | 13.1 | 160 | 44 | 114 | 428 |
| S13 | None | 13.3 | 206 | 43 | 117 | 510 |
| S14 | None | 11.1 | 169 | 32 | 146 | 604 |
| S16 | E, P | 8.9 | 128 | 24 | 27 | 452 |
| S17 | E, P | 4.5 | 93 | 16 | 25 | 340 |
| S18 | E, P | 17.6 | 159 | 32 | 18 | 413 |
| S19 | E, P | 20.3 | 155 | 19 | 38 | 349 |

E, epratuzumab;
P, prednisone;
M, methotrexate;
I, Imuran;
B, BENLYSTA ®;
$^{PE}$used instead of APC;
nd, not determined Only one of the epratuzumab group (S7) had a markedly reduced B cell count; however, this patient was also taking prednisone and methotrexate. Each of the four patients on epratuzumab without methotrexate had B cell counts in the same range as the naive patients. Both BENLYSTA® patients had low B cell counts. As expected, CD22 was significantly (P<0.0001) lower (>80%) on the B cells of epratuzumab-treated patients (not shown). Notably, CD19, CD21 and CD79b were each significantly (P<0.02) lower for the epratuzumab group (not shown). We also compared the results for the epratuzumab patient specimens with those of two patients who were receiving immunotherapy with BENLYSTA®. Although the sample size is small, both CD19 and CD22 levels were significantly (P<0.05) lower on the B cells of patients on epratuzumab compared to BENLYSTA®. The level of CD21 was similarly low for the epratuzumab and BENLYSTA® patient B cells. Because anti-CD79b-PE (instead of APC) was used to measure CD79b on B cells from BENLYSTA® patients, we could only compare these results with one epratuzumab patient specimen, which was measured similarly. The CD79-PE MFI was greater for each of the BENLYSTA® specimens (MFI=425 and 470) compared to that of the epratuzumab sample (MFI=186).

The present studies disclose important mechanisms of action of epratuzumab in normal and lupus B cells, as well as B-cell lymphomas, which may be more pertinent to the therapeutic effects of epratuzumab in autoimmune patients. The prominent loss of CD19, CD21, CD20, and CD79b induced by epratuzumab is not only Fc-dependent, but also requires further engagement with FcγR-expressing effector cells present in PBMCs. The findings of reduced levels of CD19 are of particular relevance for the efficacy of epratuzumab in autoimmune diseases, because elevated CD19 has been correlated with susceptibility to SLE in animal models as well as in patients, and loss of CD19 would attenuate activation of B cells by raising the BCR signaling threshold. Based on these findings, the activity of epratuzumab on B cells is via binding to CD22, which also occurs with F(ab')$_2$, and via engagement of FcγR-bearing effector cells. Whereas the former leads to internalization of CD22, as well as its phosphorylation with concurrent relocation to lipid rafts (resulting in the activation of tyrosine phosphatase to inhibit the activity of Syk and PLCr2), the latter results in the trogocytosis (shaving) of CD19, among others.

We propose that the consequences of losing CD19 from B cells are as follows. BCR activation upon encountering membrane-bound antigen involves the initial spreading and the subsequent formation of microclusters. Because CD19 is critical for mediating B-cell spreading, CD19-deficient B cells are unable to gather sufficient antigen to trigger B-cell activation. In addition, loss of CD19 on B cells may severely affect the ability of B cells to become activated in response to T cell-dependent antigens. Thus, the epratuzumab-mediated loss of CD19 (and possibly other BCR markers and cell-adhesion molecules) on target B cells may incapacitate such B cells and render them unresponsive to activation by T cell-dependent antigen. In summary, epratuzumab inactivates B cells via the loss of CD19, other BCR constituents, and cell-adhesion molecules that are involved in sustaining B-cell survival, leading to therapeutic control in B-cell-mediated autoimmune diseases. Although targeting B cells with either epratuzumab to CD22 or rituximab to CD20 appears to share a common effect of reducing CD19 by trogocytosis, we are currently investigating whether rituximab has a scope of trogocytosis as broad as epratuzumab. The results also caution that using CD19 as a marker for quantifying B cells by flow cytometry from patients treated with agents that induce CD19 trogocytosis may result in an over-estimation of B-cell depletion.

It has been shown with rituximab administered to chronic lymphocytic leukemia cells that too much antibody results in removal of complexes of rituximab-CD20 from the leukemia cells by trogocytosis to monocytes, and can enable these malignant cells to escape the effects of the antibody by antigenic modulation. It was then found that reducing the dose of therapeutic antibody could limit the extent of trogocytosis and improve the therapeutic effects (Herrera et al., 2006). Based on our present findings, a similar process of antigen shaving (trogocytosis) by anti-CD22 or anti-CD20 antibodies that extends beyond the respective targeted antigens can be implicated in the therapy with epratuzumab or rituximab (or the humanized anti-CD20 mAb, veltuzumab). This could explain the clinical observations that higher doses of epratuzumab administered to SLE or lymphoma patients did not show an improvement in efficacy over the mid-range dose used, because the concentrations of epratuzumab in serum would be in the μM range (150 μg/mL or higher) and could mask the low-affinity FcγRs on effector cells, thus reducing the likely events of trogocytosis.

Example 8

Administration of Epratuzumab in Systemic Lupus Erythematosus (SLE)

An open-label, single-center study of patients with moderately active SLE (total British Isles Lupus Assessment Group (BILAG) score 6 to 12) is conducted. Patients receive dosages of epratuzumab of 100, 200, 400 and 600 mg subcutaneously (SC) every week for 6 weeks. Evaluations include safety, SLE activity (BILAG), blood levels of B and T cells, human anti-epratuzumab antibody (HAHA) titers, and levels of cell surface CD19, CD20, CD21, CD22 and CD79b on B cells. It is determined that a dosage of 400-600 mg per SC injection results in optimal depletion of B cell CD19, while producing less than 50% depletion of normal B cells. Subsequently, a subcutaneous dose of 400 mg epratuzumab is administered to a new group of patients with moderately active SLE.

Total BILAG scores decrease by at least 50% in all patients, with 92% having decreases continuing to at least 18 weeks. Almost all patients (93%) experience improvement in at least one BILAG B- or C-level disease activity at 6, 10 and 18 weeks. Additionally, 3 patients with multiple BILAG B involvement at baseline have completely resolved all B-level disease activities by 18 weeks. Epratuzumab is well tolerated, with no evidence of immunogenicity or significant changes in T cells, immunoglobulins or autoantibody levels. B-cell levels decrease by an average of 35% at 18 weeks and remain depressed for 6 months post-treatment.

\* \* \*

All patents and other references cited in the specification are indicative of the level of skill of those skilled in the art to which the invention pertains, and are incorporated herein by reference, including any Tables and Figures, to the same extent as if each reference had been incorporated by reference individually. One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

What is claimed is:

1. A method of inducing caspase-dependent apoptosis of CD22$^+$ hematopoietic cancer cells comprising:
    a) exposing CD22$^+$ hematopoietic cancer cells to an anti-CD22 antibody, wherein the antibody is attached to a polystyrene bead, and wherein the antibody binds to the same epitope as epratuzumab;
    b) inhibiting cis-interaction between CD22 and CD22 ligands on the CD22$^+$ hematopoietic cancer cells;
    c) promoting trans-interaction between CD22 and CD22 ligands on other cells; and
    d) inducing caspase-dependent apoptosis of CD22$^+$ hematopoietic cancer cells.

2. The method of claim 1, further comprising exposing the CD22$^+$ cells to at least one therapeutic agent that activates caspase-dependent apoptosis.

3. The method of claim 2, wherein the therapeutic agent is selected from the group consisting of troglitazone, etoposide, paclitaxel, TRAIL, furanonaphthoquinones, and bortezomib.

4. The method of claim 1, wherein the anti-CD22 antibody is a non-blocking antibody.

5. The method of claim 1, wherein exposing CD22$^+$ hematopoietic cancer cells to an anti-CD22 antibody unmasks CD22 on the surface of the CD22$^+$ cells.

6. The method of claim 1, wherein the anti-CD22 antibody is epratuzumab.

7. The method of claim 1, wherein the anti-CD22 antibody is a humanized antibody comprising the light chain CDR sequences CDR1 (KSSQSVLYSANHKYLA, SEQ ID NO:1), CDR2 (WASTRES, SEQ ID NO:2), and CDR3 (HQYLSSWTF, SEQ ID NO:3) and the heavy chain CDR sequences CDR1 (SYWLH, SEQ ID NO:4), CDR2 (YINPRNDYTEYNQNFKD, SEQ ID NO:5), and CDR3 (RDITTFY, SEQ ID NO:6).

8. The method of claim 1, wherein the CD22$^+$ cells are human lymphoma cells or hematopoietic cancer B cells.

9. The method of claim 1, wherein the other cells are selected from the group consisting of lymphocytes, monocytes, platelets, and endothelial cells.

10. The method of claim 8, further comprising inducing phosphorylation of CD22, CD79a and CD79b and translocation of CD22, CD79a and CD79b to lipid rafts on the hematopoietic cancer B cells.

11. The method of claim 1, further comprising inducing stabilization of F-actin in the CD22$^+$ hematopoietic cancer cells.

12. The method of claim 1, further comprising inducing phosphorylation of Lyn, ERKs and JNKs, generation of reactive oxygen species (ROS), decrease in mitochondria membrane potential ($\Delta\psi_m$), upregulation of pro-apoptotic Bax, and downregulation of anti-apoptotic Bcl-xl and Mcl-1 in the CD22$^+$ hematopoietic cancer cells.

13. The method of claim 5, wherein unmasking of CD22 promotes trans-interaction of CD22$^+$ hematopoietic cancer cells with vascular endothelial cells.

14. The method of claim 8, further comprising inducing trogocytosis of CD19, CD21, CD20, CD22 and CD79b from the cell membrane of the hematopoietic cancer B cells.

15. A method of treating a hematopoietic cancer comprising:
    a) administering an anti-CD22 antibody to a subject with CD22$^+$ hematopoietic cancer, wherein the antibody is attached to a polystyrene bead, and wherein the antibody binds to the same epitope as epratuzumab;
    b) unmasking CD22 on circulating CD22$^+$ hematopoietic cancer cells in the subject; and
    c) inducing caspase-dependent apoptosis of CD22$^+$ hematopoietic cancer;
wherein inducing apoptosis of CD22$^+$ hematopoietic cancer is effective to treat the cancer or immune disease.

16. The method of claim 15, further comprising administering at least one therapeutic agent that activates caspase-dependent apoptosis.

17. The method of claim 16, wherein the therapeutic agent is selected from the group consisting of troglitazone, etoposide, paclitaxel, TRAIL, furanonaphthoquinones, and bortezomib.

18. The method of claim 15, wherein the CD22$^+$ cells are hematopoietic cancer B cells.

19. The method of claim 15, further comprising inhibiting cis-interaction between CD22 and CD22 ligands on the circulating CD22$^+$ hematopoietic cancer cells.

20. The method of claim 15, further comprising promoting trans-interaction between CD22 on CD22$^+$ hematopoietic cancer cells and CD22 ligands on other cells.

21. The method of claim 15, wherein the anti-CD22 antibody is a non-blocking antibody.

22. The method of claim 15, wherein the anti-CD22 antibody is epratuzumab.

23. The method of claim 15, wherein the anti-CD22 antibody is a humanized antibody comprising the light chain CDR sequences CDR1 (KSSQSVLYSANHKYLA, SEQ ID NO:1), CDR2 (WASTRES, SEQ ID NO:2), and CDR3 (HQYLSSWTF, SEQ ID NO:3) and the heavy chain CDR sequences CDR1 (SYWLH, SEQ ID NO:4), CDR2 (YINPRNDYTEYNQNFKD, SEQ ID NO:5), and CDR3 (RDITTFY, SEQ ID NO:6).

24. The method of claim 18, further comprising inducing phosphorylation of CD22, CD79a and CD79b and translocation of CD22, CD79a and CD79b to lipid rafts on the hematopoietic cancer B cells.

25. The method of claim 15, further comprising inducing stabilization of F-actin in the CD22$^+$ hematopoietic cancer cells.

26. The method of claim 15, further comprising inducing phosphorylation of Lyn, ERKs and JNKs, generation of reactive oxygen species (ROS), decrease in mitochondria membrane potential ($\Delta\psi_m$), upregulation of pro-apoptotic Bax, and downregulation of anti-apoptotic Bcl-xl and Mcl-1 in the CD22$^+$ hematopoietic cancer cells.

27. The method of claim 15, wherein unmasking of CD22 promotes trans-interaction of CD22$^+$ hematopoietic cancer cells with vascular endothelial cells.

28. The method of claim 18, further comprising inducing trogocytosis of CD19, CD21, CD20, CD22 and CD79b from the cell membrane of the hematopoietic cancer B cells.

29. The method of claim 18, wherein the CD22$^+$ hematopoietic cancer is selected from the group consisting of indolent forms of B-cell lymphoma, aggressive forms of B-cell lymphoma, chronic lymphocytic leukemia, acute lymphocytic leukemia, hairy cell leukemia, non-Hodgkin's lymphoma, Hodgkin's lymphoma, Burkitt lymphoma, follicular lymphoma, diffuse B-cell lymphoma, mantle cell lymphoma and multiple myeloma.

30. The method of claim 18, wherein the CD22$^+$ hematopoietic cancer is non-Hodgkin's lymphoma or acute lymphoblastic leukemia.

31. The method of claim 15, further comprising administering a drug selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), a prodrug form of 2-pyrrolinodoxorubicine (P2PDox), cyanomorpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

32. The method of claim 15, further comprising administering an immunomodulator selected is selected from the group consisting of a cytokine, a stem cell growth factor, a lymphotoxin, a hematopoietic factor, a colony stimulating factor (CSF), an interferon (IFN), erythropoietin, and thrombopoietin.

33. The method of claim 32, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factors, interferon-α, interferon-β, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

* * * * *

SEQUENCE LISTING

<160> NUMBER OF SEQ ID NOS: 20

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ser Ser Gln Ser Val Leu Tyr Ser Ala Asn His Lys Tyr Leu Ala
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ala Ser Thr Arg Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Gln Tyr Leu Ser Ser Trp Thr Phe
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Trp Leu His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Asn Pro Arg Asn Asp Tyr Thr Glu Tyr Asn Gln Asn Phe Lys
1               5                   10                  15

Asp

<210> SEQ ID NO 6
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Arg Asp Ile Thr Thr Phe Tyr
1               5

<210> SEQ ID NO 7
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

```
<210> SEQ ID NO 9
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ile Glu Tyr Leu Ala Lys Gln Ile Val Asp Asn Ala Ile Gln Gln
1               5                   10                  15

Ala

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 13

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 14
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 16
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 17
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Gly Phe Ala Leu
            20                  25                  30

Gln His Phe Thr Arg Leu Gln Gln Glu Asn Glu Arg
        35                  40

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES

```
<222> LOCATION: (4)..(4)
<223> OTHER INFORMATION: Lys(HSG)
<220> FEATURE:
<223> OTHER INFORMATION: C-term NH2

<400> SEQUENCE: 20

Phe Lys Tyr Lys
1
```